(12) United States Patent
Hartman et al.

(10) Patent No.: US 6,294,549 B1
(45) Date of Patent: Sep. 25, 2001

(54) METHOD FOR ELICITING AN $\alpha_V\beta_5$ OR DUAL $\alpha_V\beta_3/\alpha_V\beta_5$ ANTAGONIZING EFFECT

(75) Inventors: George D. Hartman, Lansdale; Mark E. Duggan, Schwenksville, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/120,997

(22) Filed: Jul. 23, 1998

Related U.S. Application Data

(60) Provisional application No. 60/053,644, filed on Jul. 24, 1997, and provisional application No. 60/053,537, filed on Jul. 23, 1997.

(51) Int. Cl.⁷ .............. A61K 31/505; A61K 31/44; C07D 239/02; C07D 211/72; C07D 233/38
(52) U.S. Cl. .............. 514/300; 514/242; 514/255; 514/212; 514/274; 514/340; 514/18; 514/19; 540/524; 544/182; 544/316; 544/360; 544/393; 544/405; 546/122; 546/194; 546/273.4; 546/277.4; 546/300; 546/309; 546/331
(58) Field of Search ............... 514/300, 212, 514/242, 255, 274, 18, 19, 340; 540/524; 544/182, 316, 360, 393, 405; 546/122, 194, 273.4, 277.4, 300, 309, 331

(56) References Cited

U.S. PATENT DOCUMENTS

| | | | |
|---|---|---|---|
| 3,553,227 | 1/1971 | Westland | 260/306.8 |
| 4,122,255 | 10/1978 | Krapcho | 542/421 |
| 4,250,183 | 2/1981 | Krastinat | 424/263 |
| 4,684,772 | 8/1987 | Sundeen | 540/203 |
| 5,227,490 | 7/1993 | Hartman et al. | 514/317 |
| 5,264,420 | 11/1993 | Duggan et al. | 514/19 |
| 5,281,585 | 1/1994 | Duggan et al. | 514/79 |
| 5,292,756 | 3/1994 | Duggan et al. | 514/331 |
| 5,294,616 | 3/1994 | Duggan et al. | 514/255 |
| 5,321,034 | 6/1994 | Duggan et al. | 514/323 |
| 5,358,956 | 10/1994 | Hartman et al. | 514/331 |
| 5,919,792 * | 7/1999 | Duggan et al. | 514/300 |

FOREIGN PATENT DOCUMENTS

| | | |
|---|---|---|
| 0 372 486 | 6/1990 | (EP) . |
| 0 381 033 | 8/1990 | (EP) . |
| 0 384 362 | 8/1990 | (EP) . |
| WO 95/09634 | 4/1995 | (WO) . |
| WO 97/26250 | 7/1997 | (WO) . |

* cited by examiner

Primary Examiner—James O. Wilson
Assistant Examiner—Howard Owens
(74) Attorney, Agent, or Firm—Richard S. Parr; Melvin Winokur

(57) ABSTRACT

A method for eliciting an $\alpha_V\beta_5$ or dual $\alpha_V\beta_3/\alpha_V\beta_5$ antagonizing effect in a mammal which comprises administering to the mammal a therapeutically effective amount of a compound of the formula

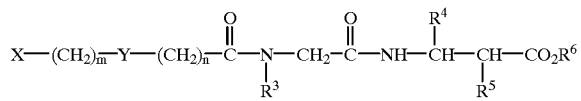

for example

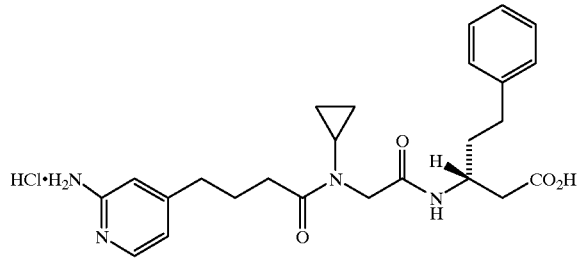

which are useful for inhibiting restenosis, angiogenesis, atherosclerosis, diabetic retinopathy, macular degeneration, inflammation or tumor growth.

10 Claims, No Drawings

METHOD FOR ELICITING AN $\alpha_v\beta_5$ OR DUAL $\alpha_v\beta_3/\alpha_v\beta_5$ ANTAGONIZING EFFECT This appln claims benefit of Provisional Nos. 60/053,644 filed Jul. 24, 1997 and 60/053,537 filed Jul. 23, 1997.

BACKGROUND OF THE INVENTION

The invention relates generally to αvβ5 antagonists useful for inhibiting vascular restenosis, diabetic retinopathy, macular degeneration, angiogenesis, atherosclerosis, inflammation and tumor growth.

The method of the invention can inhibit neovascularization by acting as antagonists of the integrin receptor αvβ5. A monoclonal antibody for αvβ5 has been shown to inhibit VEGF-induced angiogenesis in rabbit cornea and the chick chorioallantoic membrane model; M. C. Friedlander, et al., *Science* 270, 1500–1502, 1995. Thus, compounds that antagonize αvβ5 are useful for treating and preventing macular degeneration, diabetic retinopathy, tumor growth and for inhibiting vascular restenosis, angiogenesis, and inflammation.

SUMMARY OF THE INVENTION

The invention is a method for eliciting an $\alpha_v\beta_5$ or dual $\alpha_v\beta_3/\alpha_v\beta_5$ antagonizing effect in a mammal which comprises administering to the mammal a therapeutically effective amount of a compound of the formula:

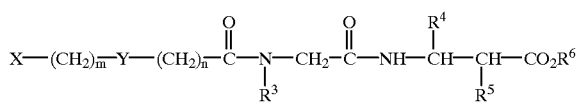

and pharmaceutically acceptable salts thereof, wherein

X is
  a 5- or 6-membered monocyclic aromatic ring system containing 0, 1, 2, 3 or 4 heteroatoms selected from N, O and S and either unsubstituted or substituted with $R^1$ or $R^2$, or
  a 9- to 10-membered polycyclic ring system, wherein one or more of the rings is aromatic, containing 0, 1, 2, 3 or 4 heteroatoms selected from N, O and S and either unsubstituted or substituted with $R^1$ or $R^2$,
  wherein $R^1$ and $R^2$ are independently selected from the group consisting of
    hydrogen, F, Cl, Br, I,
    $C_{1-10}$ alkyl,
    $C_{3-8}$ cycloalkyl,
    aryl,
    aryl $C_{1-8}$ alkyl,
    amino,
    amino $C_{1-8}$ alkyl,
    $C_{1-3}$ acylamino,
    $C_{1-3}$ acylamino $C_{1-8}$ alkyl,
    $C_{1-6}$ alkylamino,
    $C_{1-6}$ alkylamino $C_{1-8}$ alkyl,
    $C_{1-6}$ dialkylamino,
    $C_{1-6}$ dialkylamino $C_{1-8}$ alkyl,
    $C_{1-4}$ alkoxy,
    $C_{1-4}$ alkoxy $C_{1-6}$ alkyl,
    carboxy,
    carboxy $C_{1-6}$ alkyl,
    $C_{1-3}$ alkoxycarbonyl,
    $C_{1-3}$ alkoxycarbonyl $C_{1-6}$ alkyl,
    carboxy $C_{1-6}$ alkyloxy,
    hydroxy, and
    hydroxy $C_{1-6}$ alkyl;

Y is

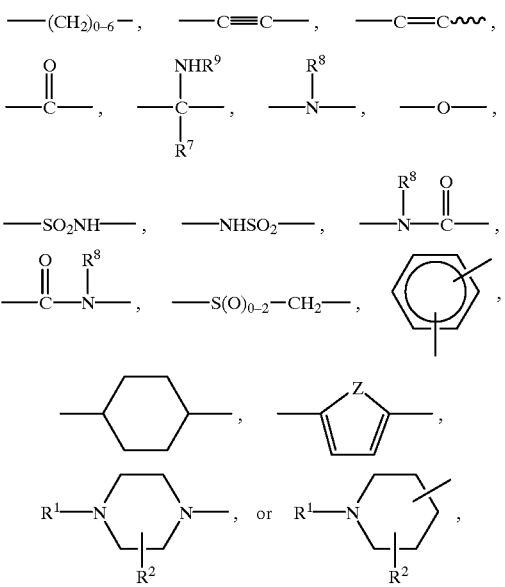

where Z is O, $NR^8$, or S; and $R^8$ is defined as $R^1$ above;

$R^3$ and $R^4$ are independently
  hydrogen,
  a five or six membered mono or nine or ten membered polycyclic unsaturated, partially or fully saturated ring system containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy,
  —$(CH_2)_n$-aryl, wherein n=1–4 and aryl is defined as a five or six membered unsaturated or partially saturated monocyclic ring system, or nine or ten membered polycyclic ring system wherein at least one of the rings is unsaturated or partially saturated and each of the other rings may be unsaturated, partially saturated or fully saturated, said aryl group containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy,
  halogen,
  hydroxyl,
  $C_{1-5}$alkylcarbonylamino,
  aryl$C_{1-5}$ alkoxy,
  $C_{1-5}$ alkoxycarbonyl,
  aminocarbonyl,
  $C_{1-5}$ alkylaminocarbonyl,
  $C_{1-5}$ alkylcarbonyloxy,
  $C_{3-8}$ cycloalkyl,
  oxo,
  amino, C$_{1-3}$ alkylamino,
aminoC$_{1-3}$ alkyl,
arylaminocarbonyl,
arylC$_{1-5}$alkylaminocarbonyl,
aminocarbonyl,
aminocarbonyl-C$_{1-4}$ alkyl,
hydroxycarbonyl,
hydroxycarbonyl C$_{1-5}$ alkyl,
C$_{1-6}$alkyl, either unsubstituted or substituted, with one or more groups selected from halogen, hydroxyl, C$_{1-5}$alkylcarbonylamino, arylC$_{1-5}$ alkoxy, C$_{1-5}$ alkoxycarbonyl, aminocarbonyl, C$_{1-5}$ alkylaminocarbonyl, C$_{1-5}$ alkylcarbonyloxy, C$_{3-8}$ cycloalkyl, oxo, amino, C$_{1-3}$ alkylamino, aminoC$_{1-3}$ alkyl, arylaminocarbonyl, arylC$_{1-5}$alkylaminocarbonyl, aminocarbonyl, aminocarbonyl-C$_{1-4}$ alkyl, hydroxycarbonyl, or hydroxycarbonyl C$_{1-5}$ alkyl, provided that the carbon atom to which R$^3$ and R$^4$ are attached bears only one heteroatom,
—(CH$_2$)$_m$C≡CH,
—(CH$_2$)$_m$C≡C—C$_{1-6}$ alkyl,
—(CH$_2$)$_m$C≡C—C$_{3-7}$cycloalkyl,
—(CH$_2$)$_m$C—C≡ aryl,
—(CH$_2$)$_m$C≡C—C$_{1-6}$ alkyl aryl,
—(CH$_2$)$_m$CH═CH$_2$,
—(CH$_2$)$_m$CH═CH≡C$_{1-6}$ alkyl,
—(CH$_2$)$_m$CH═CH—C$_{3-7}$cycloalkyl,
—(CH$_2$)$_m$CH═CH aryl,
—(CH$_2$)$_m$CH═CH C$_{1-6}$ alkyl aryl,
—(CH$_2$)$_m$SO$_2$C$_{1-6}$ alkyl, or
—(CH$_2$)$_m$SO$_2$C$_{1-6}$ alkylaryl;
R$^5$ is
hydrogen,
fluorine,
C$_{1-8}$ alkyl,
hydroxyl,
hydroxy C$_{1-6}$ alkyl,
carboxy,
carboxy C$_{1-6}$ alkyl,
C$_{1-6}$ alkyloxy.
C$_{3-8}$ cycloalkyl,
aryl C$_{1-6}$ alkyloxy,
aryl,
aryl C$_{1-6}$ alkyl,
C$_{1-6}$ alkylcarbonyloxy,
amino,
C$_{1-6}$ alkylamino,
amino C$_{1-6}$ alkyl,
C$_{1-6}$ alkylamino C$_{1-6}$ alkyl,
aryl amino,
aryl amino C$_{1-6}$ alkyl,
aryl C$_{1-6}$ alkylamino,
aryl C$_{1-6}$ alkylamino C$_{1-6}$ alkyl,
aryl carbonyloxy,
aryl C$_{1-6}$ alkylcarbonyloxy,
C$_{1-6}$ dialkylamino,
C$_{1-6}$ dialkylamino C$_{1-6}$ alkyl,
C$_{1-6}$ alkylaminocarbonyloxy,
C$_{1-8}$ alkylsulfonylamino,
C$_{1-8}$ alkylsulfonylamino C$_{1-6}$ alkyl,
aryl sulfonylamino C$_{1-6}$ alkyl,
aryl sulfonylamino,
aryl C$_{1-6}$ alkylsulfonylamino,
aryl C$_{1-6}$ alkylsulfonylamino C$_{1-6}$ alkyl,
C$_{1-8}$ alkyloxycarbonylamino,
C$_{1-8}$ alkyloxycarbonylamino C$_{1-8}$ alkyl,
aryl C$_{1-8}$ alkyloxycarbonylamino,
aryl oxycarbonylamino,
aryl oxycarbonylamino C$_{1-8}$ alkyl,
aryl C$_{1-8}$ alkyloxycarbonylamino C$_{1-8}$ alkyl,
C$_{1-8}$ alkylcarbonylamino,
C$_{1-8}$ alkylcarbonylamino C$_{1-6}$ alkyl,
aryl carbonylamino C$_{1-6}$ alkyl,
aryl carbonylamino,
aryl C$_{1-6}$ alkylcarbonylamino,
aryl C$_{1-6}$ alkylcarbonylamino C$_{1-6}$ alkyl,
C$_{1-8}$ alkylaminocarbonylamino,
aminocarbonylamino,
aminocarbonylamino C$_{1-6}$ alkyl,
C$_{1-8}$ alkylaminocarbonylamino C$_{1-6}$ alkyl,
aryl aminocarbonylamino C$_{1-6}$ alkyl,
aryl aminocarbonylamino,
aryl C$_{1-8}$ alkylaminocarbonylamino,
aryl C$_{1-8}$ alkylaminocarbonylamino C$_{1-6}$ alkyl,
aminosulfonylamino C$_{1-6}$ alkyl,
aminosulfonylamino,
C$_{1-8}$ alkylaminosulfonylamino,
C$_{1-8}$ alkylaminosulfonylamino C$_{1-6}$ alkyl,
aryl aminosulfonylamino C$_{1-6}$ alkyl,
aryl aminosulfonylamino,
aryl C$_{1-8}$ alkylaminosulfonylamino,
aryl C$_{1-8}$ alkylaminosulfonylamino C$_{1-6}$ alkyl,
C$_{1-6}$ alkylsulfonyl,
C$_{1-6}$ alkylsulfonyl C$_{1-6}$alkyl,
aryl sulfonyl,
aryl sulfonyl C$_{1-6}$alkyl,
aryl alkylsulfonyl,
aryl C$_{1-6}$ alkylsulfonyl,
aryl C$_{1-6}$ alkylsulfonyl C$_{1-6}$alkyl,
C$_{1-6}$ alkylcarbonyl,
C$_{1-6}$ alkylcarbonyl C$_{1-6}$ alkyl,
aryl carbonyl C$_{1-6}$alkyl,
aryl carbonyl,
aryl C$_{1-6}$ alkylcarbonyl,
aryl C$_{1-6}$ alkylcarbonyl C$_{1-6}$alkyl,
C$_{1-6}$ alkylthiocarbonylamino,
C$_{1-6}$ alkylthiocarbonylamino C$_{1-6}$ alkyl,
aryl thiocarbonylamino C$_{1-6}$ alkyl,
aryl thiocarbonylamino,
aryl C$_{1-6}$ alkylthiocarbonylamino,
aryl C$_{1-6}$ alkylthiocarbonylamino C$_{1-6}$ alkyl,
aminocarbonyl C$_{1-6}$ alkyl,
aminocarbonyl,
C$_{1-8}$ alkylaminocarbonyl,
C$_{1-8}$ alkylaminocarbonyl C$_{1-6}$ alkyl,
aryl aminocarbonyl C$_{1-6}$ alkyl,
aryl aminocarbonyl,
aryl C$_{1-8}$ alkylaminocarbonyl,
aryl C$_{1-8}$ alkylaminocarbonyl C$_{1-6}$ alkyl,
wherein alkyl groups and aryl groups may be unsubstituted or substituted with one or more substituents selected from R$^1$ and R$^2$; and
R$^6$, R$^7$, and R$^9$ are independently
hydrogen,
C$_{1-8}$ alkyl,
aryl,
aryl C$_{1-8}$ alkyl,
hydroxy,
C$_{1-8}$ alkyloxy,
aryloxy,
aryl C$_{1-6}$ alkyloxy,
C$_{1-8}$ alkylcarbonyloxy C$_{1-4}$ alkyloxy,
aryl C$_{1-8}$ alkylcarbonyloxy C$_{1-4}$ alkyloxy, $C_{1-8}$ alkylaminocarbonylmethyleneoxy, or
$C_{1-8}$ dialkylaminocarbonylmethyleneoxy,
and wherein m and n are integers 0–6.

The invention is also a method for inhibiting a condition selected from the group conistsing of restenosis, angiogenesis, diabetic retinopathy, macular degeneration, inflammation, and tumor growth in a mammal which comprises administering to the mammal a therapeutically effective amount of a compound defined above.

In a class of methods of the invention, the compounds of the formula are

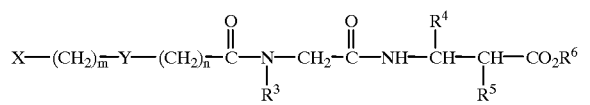

and pharmaceutically acceptable salts thereof, wherein
X is

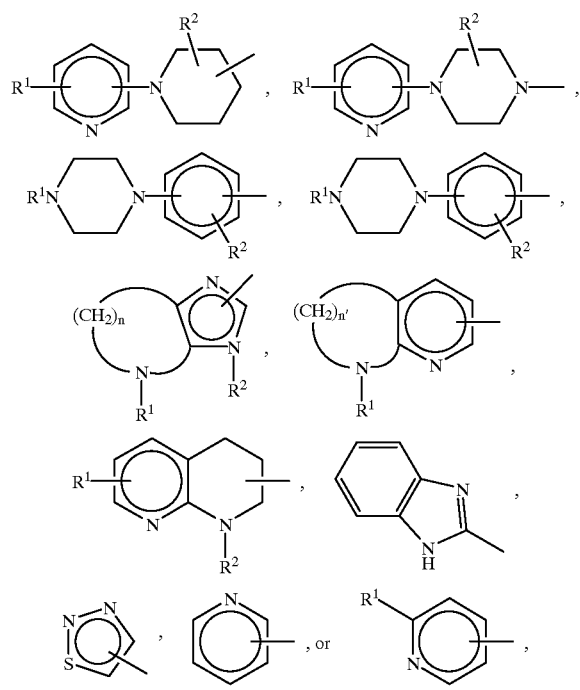

wherein n is 2–4, and n' is 2 or 3, and
wherein $R^1$ and $R^2$ are independently selected from the group consisting of
hydrogen, F, Cl, Br, I,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-4}$ alkoxy,
$C_{1-4}$ alkoxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl.

The invention is also a method for inhibiting a condition selected from the group conistsing of restenosis, angiogenesis, diabetic retinopathy, macular degeneration, inflammation, and tumor growth in a mammal which comprises administering to the mammal a therapeutically effective amount of a compound defined above.

In a subclass of the class of methods described above, the compounds of the formula

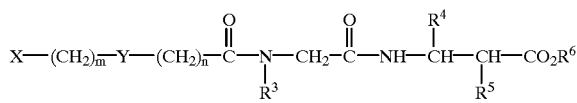

and pharmaceutically acceptable salts thereof, wherein
X is

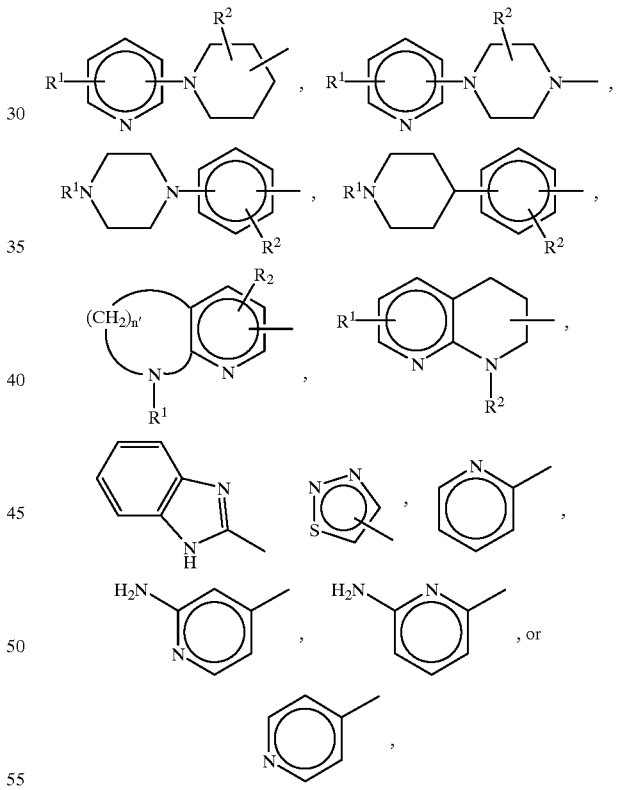

wherein n' is 2 or 3, and
Y is

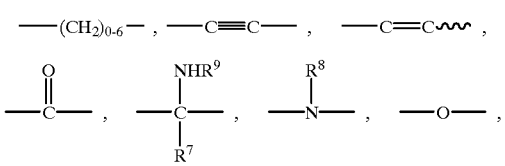

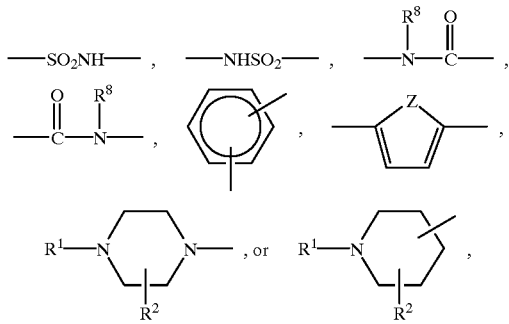

where Z is O, NR⁸, or S; and R⁸ is defined as R¹.

The invention is also a method for inhibiting a condition selected from the group conistsing of restenosis, angiogenesis, diabetic retinopathy, macular degeneration, inflammation, and tumor growth in a mammal which comprises administering to the mammal a therapeutically effective amount of a compound defined above.

In a group of the subclass are methods wherein the compounds have the formula

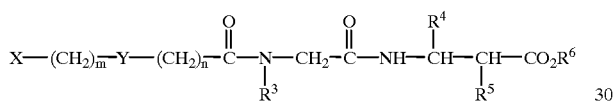

and pharmaceutically acceptable salts thereof, wherein

X is

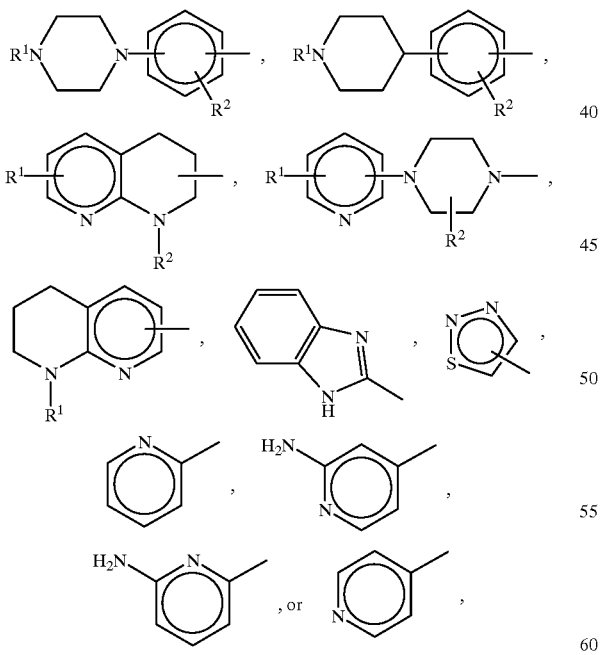

wherein $R^1$ and $R^2$ are independently selected from the group consisting of
  hydrogen or
  amino,
  amino $C_{1-8}$ alkyl;

Y is

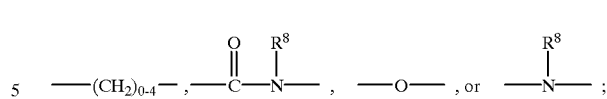

$R^8$ is hydrogen or aryl $C_{0-8}$ alkyl;

$R^3$ is
  hydrogen,
  a six membered monocyclic unsaturated, partially or fully saturated ring system, either unsubstituted or substituted, with one or mores groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy,
  —$(CH_2)_n$-aryl, wherein n=1–4 and aryl is defined as a six membered monocyclic unsaturated or partially saturated ring system, either unsubstituted or substituted, with one or more groups selected from hydroxyl, halogen, cyano, trifluoromethyl, $C_{1-3}$ alkoxy, $C_{1-5}$ alkylcarbonyloxy; $C_{1-5}$ alkoxycarbonyl, $C_{1-5}$ alkyl, aminoCi-5 alkyl, hydroxycarbonyl, hydroxycarbonyl$C_{1-5}$ alkyl, or hydroxycarbonyl$C_{1-5}$ alkoxy,
  $C_{3-8}$ cycloalkyl, or
  $C_{1-6}$alkyl, either unsubstituted or substituted, with $C_{3-8}$ cycloalkyl;

$R^4$ is
  hydrogen,
  —$(CH_2)_n$-aryl, wherein n=0–4 and aryl is defined as a six membered monocyclic unsaturated or partially saturated ring or a nine or ten membered polycyclic ring system wherein at least one of the rings is unsaturated or partially saturated and each of the other rings may be unsaturated, partially saturated or fully saturated, said aryl group either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl$C_{0-5}$ alkyl, or hydroxycarbonyl$C_{1-5}$ alkoxy,
  $C_{1-6}$alkyl, or
  —$(CH_2)_{0-4}C\equiv CH$;

$R^5$ is
  hydrogen,
  aryl sulfonylamino $C_{1-6}$ alkyl,
  aryl sulfonylamino,
  aryl $C_{1-6}$ alkylsulfonylamino,
  aryl $C_{1-6}$ alkylsulfonylamino $C_{1-6}$ alkyl,
  $C_{1-8}$ alkylsulfonylamino,
  $C_{1-8}$ alkylsulfonylamino $C_{1-6}$ alkyl,
  aryl sulfonylamino $C_{1-6}$ alkyl,
  aryl sulfonylamino,
  aryl $C_{1-6}$ alkylsulfonylamino,
  aryl $C_{1-6}$ alkylsulfonylamino $C_{1-6}$ alkyl,
  aminosulfonylamino $C_{1-6}$ alkyl,
  aminosulfonylamino,
  $C_{1-8}$ alkylaminosulfonylamino,
  $C_{1-8}$ alkylaminosulfonylamino $C_{1-6}$ alkyl,
  aryl aminosulfonylamino $C_{1-6}$ alkyl,
  aryl aminosulfonylamino,
  aryl $C_{1-8}$ alkylaminosulfonylamino,
  aryl $C_{1-8}$ alkylaminosulfonylamino $C_{1-6}$ alkyl,
  $C_{1-6}$ alkylsulfonyl, $C_{1-6}$ alkylsulfonyl $C_{1-6}$alkyl,
aryl sulfonyl $C_{1-6}$alkyl,
aryl sulfonyl,
aryl $C_{1-6}$ alkylsulfonyl,
aryl $C_{1-6}$ alkylsulfonyl $C_{1-6}$alkyl, wherein alkyl groups and aryl groups may be unsubstituted or substituted with one or more substituents selected from $R^1$ and $R^2$; and $R^6$ is
hydrogen,
$C_{1-8}$ alkyl, or
aryl,
aryl $C_{1-8}$ alkyl.

The invention is also a method for inhibiting a condition selected from the group conistsing of restenosis, angiogenesis, diabetic retinopathy, macular degeneration, inflammation, and tumor growth in a mammal which comprises administering to the mammal a therapeutically effective amount of a compound defined above.

In a subgroup of the group are methods wherein the compounds have the formula

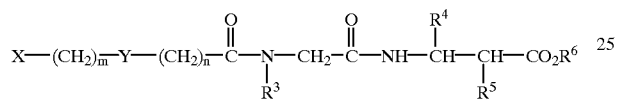

and pharmaceutically acceptable salts thereof, wherein
X is

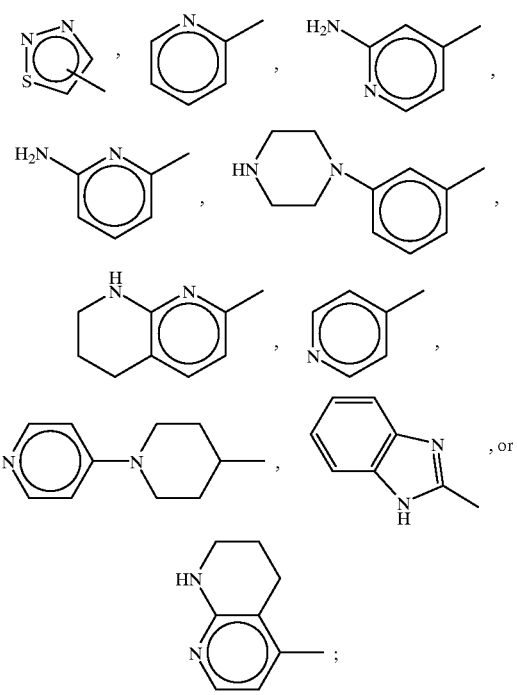

Y is

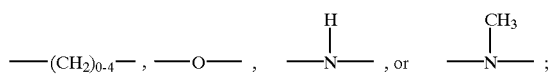

$R^3$ is
hydrogen,
methyl,

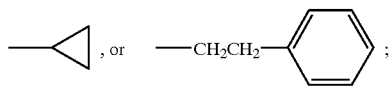

$R^4$ is
hydrogen,
methyl,

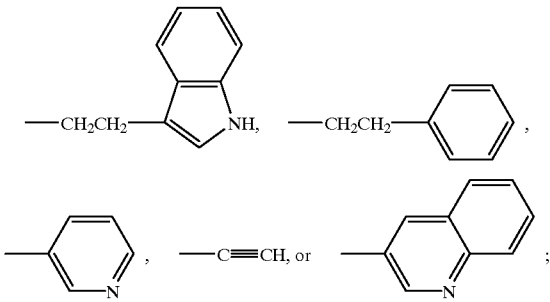

$R^5$ is
hydrogen, or

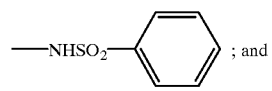
; and $R^6$ is
hydrogen,
methyl,
ethyl, or
t-butyl.

The invention is also a method for inhibiting a condition selected from the group conistsing of restenosis, angiogenesis, diabetic retinopathy, macular degeneration, inflammation, and tumor growth in a mammal which comprises administering to the mammal a therapeutically effective amount of a compound defined above.

Specific examples of this subgroup include methods wherein the compounds are
4-(2-Aminothiazol-4-yl)butanoyl-glycyl-2(S)-phenylsulfonamido-β-alanine t-butyl ester,
4-(2-Aminothiazol-4-yl)butanoyl-glycyl-2(S)-phenylsulfonamido-β-alanine,
4-(2-Aminothiazol-4-yl)butanoyl-glycyl-3(R)-(2-phenethyl)-β-alanine methyl ester,
4-(2-Aminothiazol-4-yl)butanoyl-glycyl-3(R)-(2-phenethyl)-β-alanine,
5-(2-Pyridylamino)pentanoylglycyl-2(S)-phenylsulfonamido-β-alanine ethyl ester,
5-(2-Pyridylamino)pentanoylglycyl-2(S)-phenylsulfonamido-β-alanine,
4-(2-Amino-pyridin-6-yl)butanoyl-sarcosine-3(R)-[(2-indol-3-yl)ethyl]-β-alanine ethyl ester,
4-(2-Aminopyridin-6-yl)butanoyl-sarcosine-3(R)-[(2-indol-3-yl)ethyl]-β-alanine,
4-(2-Aminopyridin-6-yl)butanoyl-glycyl-2(S)-phenylsulfonamido-β-alanine t-butyl ester,
4-(2-Aminopyridin-6-yl)butanoyl-glycyl-2(S)-phenylsulfonamido-β-alanine,
4-(Pyridin-4-yl)butanoyl-sarcosine-3(R)-[2-(indol-3-yl)ethyl]-β-alanine ethyl ester, 4-(Pyridin-4-yl)butanoyl sarcosine-3(R)-[2-(indol-3-yl)ethyl]-β-alanine,
4-(2-Bocamino-pyridin-6-yl)butanoyl-N-cyclopropylglycyl-3(R)-(2-phenethyl)-β-alanine ethyl ester,
4-(2-Amino-pyzidin-6-yl)butanoyl-N-cyclopropylglycyl-3(R)-(2-phenethyl)-β-alanine ethyl ester,
4-(2-Amino-pyridin-6-yl)butanoyl-N-cyclopropylglycyl-3(R)-(2-phenethyl)-β-alanine,
4-(2-Boc-amino-pyridin-6-yl)butanoyl-N-cyclopropylglycyl-3(R)-[(2-indol-3-yl)ethyl]-β-alanine,
4-(2-Amino-pyridin-6-yl)butanoyl-N-cyclopropylglycyl-3(R)-[(2-indol-3-yl)ethyl]-β-alanine,
4-(2-Bocamino-pyridin-6-yl)butanoyl-N-cyclopropylglycyl-3(R)-methyl-β-alanine ethyl ester,
4-(2-Amino-pyridin-6-yl)butanoyl-N-cyclopropylglycyl-3(R)-methyl-β-alanine ethyl ester,
4-(2-Amino-pyridin-6-yl)butanoyl-N-cyclopropylglycyl-3(R)-methyl-β-alanine,
4-(Pyridin-4-yl)butanoyl-N-(2-phenylethyl)glycyl-3(R)-(2-phenethyl)-β-alanine ethyl ester,
4-(Pyridin-4-yl)butanoyl-N-(2-phenyl)glycyl-3(R)-(2-phenethyl)-β-alanine,
4-(2-BOC-Aminopyridin-4-yl)butanoyl-N-(2-phenethyl)glycyl-3(R)-methyl-β-alanine,
4-(2-Aminopyridin-4-yl)butanoyl-N-(2-phenethyl)glycyl-3(R)-methyl-β-alanine,
4-(Pyridyloxy)butyrate-N-(2-phenethyl)glycyl-3(R)-2-phenethyl-β-alanine ethyl ester,
4-(Pyridyloxy)butyrate-N-(2-phenethyl)glycyl-3(R)-2-phenethyl-β-alanine,
3-[(N-Methyl)-N-(4-pyridyl)]aminopropionyl-sarcosine-3(R)-(2-phenethyl)-β-alanine ethyl ester,
3-[(N-Methyl)-N-(4-pyridyl)]aminopropionyl-sarcosine-3(R)-(2-phenethyl)-β-alanine,
N-{N'-3-(4-t-Butoxycarbonyl-1-piperizinyl)benzoyl)glycyl}-3(R)-methyl-β-alanine benzyl ester,
N-[N'-[3-(1-Piperazinyl)benzoyl]glycyl]-3(R)-methyl-β-alanine,
N-[N'-[3-(4-t-Butoxycarbonyl-1-piperazinyl)benzoyl]glycyl]-3(R)-(2-phenethyl)-β-alanine methyl ester,
N-[N'-[3-(1-Piperazinyl)benzoyl]glycyl]-3(R)-(2-phenethyl)-β-alanine,
N-[N'-[3-(4-t-Butoxycarbonyl-1-piperazinyl)benzoyl]-N'-(2-phenethyl)glycyl]-3(R)-(2-phenethyl)-β-alanine methyl ester,
N-[N'-[3-(1-Piperazinyl)benzoyl]-N'-(2-phenethyl)glycyl]-3(R)-(2-phenethyl)-β-alanine,
4-(1,2,3,4-Tetrahydro-1,8-naphthyridin-7-yl)butanol-glycyl-β-alanine t-butyl ester,
4-(1,2,3,4-Tetrahydro-1,8-naphthyridin-7-yl)butanoyl-glycyl-β-alanine,
4-(1,2,3,4-Tetrahydro-1,8-naphthyridin-7-yl)butanoyl-glycyl-3(S)-pyridin-3-yl-β-alanine ethyl ester,
4-(1,2,3,4-Tetrahydro-1,8-naphthyridin-7-yl)butanoyl-glycyl-3(S)pyridin-3-yl-β-alanine,
Ethyl N-pyridin-4-ylisonipecotyl-N-cyclopropylglycine-3(S)-ethynyl-β-alanine,
N-Pyridin-ylisonipecotyl-N-cyclopropylglycine-3(S)-ethynyl-β-alanine,
Ethyl N-pyridin-4-ylnipecotyl-N-cyclopropylglycine-3(S)-ethynyl-β-alanine,
N-Pyridin-4-ylnipecotyl-N-cyclopropylglycine-3(S)-ethynyl-β-alanine,
4-(1,2,3,4-Tetrahydro-1,8-naphthyridin-5-yl)butanoyl-N-(cyclo-propyl)gly-3(S)ethynyl-β-alanine ethyl ester,
4-(1,2,3,4-Tetrahydro-1,8-naphthyridin-5-yl)butanoyl-N-(cyclo-propyl)glycyl-3(S)-ethynyl-β-alanine, or
3-{2-[5-(1H-Benzoimidazol-2-yl-amino)-pentanoylamino]-acetylamino}-3(S)-pyridin-3-yl-propionic acid,
or a pharmaceutically acceptable salt, such as a trifluoroacetate salt (e.g. 4-(2-Aminothiazol-4-yl)butanoyl-glycyl-3(R)-(2-phenethyl)-β-alanine trifluoroacetate salt, 5-(2-Pyridylamino)pentanoylglycyl-2(S)-phenylsulfonamido-β-alanine trifluoroacetate salt, N-[N'-[3-(1-Piperazinyl)benzoyl]glycyl]-3(R)-methyl-β-alanine trifluoroacetic acid salt, N-[N'-[3-(1-Piperazinyl)benzoyl]glycyl]-3(R)-(2-phenethyl)-β-alanine trifluoroacetic acid salt, N-[N'-[3-(1-Piperazinyl)benzoyl]-N'-(2-phenethyl)glycyl]-3(R)-(2-phenethyl)-β-alanine trifluoroacetic acid salt) or a hydrochloric acid salt (e.g. 4-(2-Amino-pyridin-6-yl)butanoyl-N-cyclopropylglycyl-3(R)-(2-phenethyl)-β-alanine ethyl ester hydrochloride).

The invention is also a method for inhibiting a condition selected from the group conistsing of restenosis, angiogenesis, diabetic retinopathy, macular degeneration, inflammation, and tumor growth in a mammal which comprises administering to the mammal a therapeutically effective amount of a compound defined above.

An example of the invention is the method wherein the antagonizing effect is an αvβ5 antagonizing effect illustrated by the effects of inhibiting restenosis, atherosclerosis, angiogenesis, diabetic retinopathy, macular degeneration, inflammation or tumor growth.

The methods of the invention are particularly useful for inhibiting tumor growth in mammals. Pharmacologically effective amounts of the compounds, including pharmaceutically acceptable salts thereof, are administered to the mammal, to inhibit tumor growth. The growth of tumors depends on an adequate blood supply, which in turn depends on growth of new vessels into the tumor. New vessels are stimulated by factors secreted by the tumor. Inhibition of angiogenesis can cause tumor regression in animals.

The methods of the invention are also particularly useful for treating and preventing diabetic retinopathy in mammals. Pharmacologically effective amounts of the compounds, including pharamaceutically acceptable salts thereof, are administered to the mammal, to inhibit diabetic retinopathy.

More particularly illustrating the invention is a method for eliciting an $α_vβ_5$ or dual $α_vβ_3/α_vβ_5$ antagonizing effect in a mammal in need thereof, comprising administering to the mammal a pharmaceutical composition comprising any of the compounds described above and a pharmaceutically acceptable carrier.

Further illustrating the invention is a method of treating and/or preventing a condition mediated by antagonism of a vitronectin receptor in a mammal in need thereof, comprising administering to the mammal a therapeutically effective amount of any of the compounds described above. Preferably, the condition is selected from restenosis, atherosclerosis, diabetic retinopathy, macular degeneration, angiogenesis, inflammation, and tumor growth.

More specifically exemplifying the invention is a method of eliciting an antagonizing effect in a mammal in need thereof, comprising administering to the mammal a therapeutically effective amount of any of the compounds or any of the pharmaceutical compositions described above, wherein the antagonizing effect is an αvβ5 antagonizing effect (e.g. inhibition of restenosis, atherosclerosis, aniogenesis, diabetic retinopathy, macular degeneration, inflammation or tumor growth).

More particularly illustrating the invention is any of the methods of treating and/or preventing osteoporosis and/or of inhibiting bone resorption described above, wherein the compound is administered in combination with a second bone resorption inhibitor; preferably, the second bone resorption inhibitor is alendronate.

More particularly exemplifying the invention is the use of any of the compounds described above in the preparation of a medicament for the treatment and/or prevention of tumor growth, restenosis, atherosclerosis, diabetic retinopathy, macular degeneration, inflammation and/or angiogenesis.

DETAILED DESCRIPTION OF THE INVENTION

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, trifluoroacetate, and valerate.

Compounds of the present invention are chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention.

Prodrugs, such as ester derivatives of described compounds, are compound derivatives which, when absorbed into the bloodstream of a warm-blooded animal, cleave in such a manner as to release the drug form and permit the drug to afford improved therapeutic efficacy. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The term "pharmaceutically effective amount" shall mean that amount of a drug or pharmaceutical agent that will elicit the biological or medical response of a tissue, system or animal that is being sought by a researcher or clinician.

The term "anti-coagulant" shall include heparin, and warfarin.

The term "thrombolytic agent" shall include agents such as streptokinase and tissue plasminogen activator.

The term "platelet anti-aggregation agent" shall include agents such as aspirin and dipyridamole.

The term "antagonist," as used herein, refers to a compound which binds to and antagonizes either the αvβ3 receptor or the αvβ5 receptor, or a compound which binds to and antagonizes both the αvβ3 and αvβ5 receptors (i.e., a dual αvβ3/αvβ5 receptor antagonist).

The term "bone resorption" means the process by which osteoclasts solubilize bone minerals and increase the activity of enzymes that degrade bone matrix.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like.

The term "alkenyl" shall mean straight or branched chain alkenes of two to ten total carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like.

The term "alkynyl" shall mean straight or branched chain alkynes of two to ten total carbon atoms containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O or S. Examples of cycloheteroalkyl groups include, but are not limited to piperidinyl, pyrrolidinyl, azetidinyl, morpholinyl, piperazinyl.

The term "aromatic ring" refers, but is not limited, to unsaturated ring systems such as phenyl and naphthyl rings and unsaturated heterocyclic ring systems such as

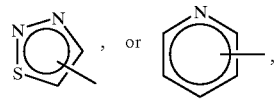

The term "9- to 10-membered polycyclic ring system, wherein one or more of the rings is aromatic" refers, but is not limited, to ring systems such as

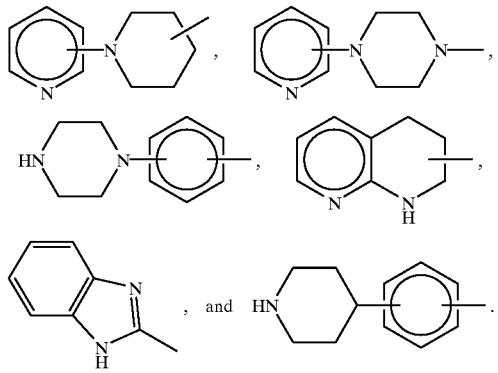

Unless otherwise specifically defined, the term "aryl" means a 5- or 6-membered unsaturated or partially saturated ring or a 9- or 10-membered polycyclic ring system wherein at least one of the rings is unsaturated or partially saturated and each of the other rings may be unsaturated, partially saturated or fully saturated, said aryl group containing 0, 1, or 2 heteroatoms selected from O, N, and S and either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include phenyl, pyridine, pyrimidine, imidazole, thiophene, oxazole, isoxazole, thiazole, and amino- and halogen-substituted derivatives thereof.

The terms "alkyloxy" or "alkoxy" include an alkyl portion where alkyl is as defined above. Examples of alkoxy include methyloxy, propyloxy, and butyloxy.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit. Examples of arylalkyl include benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include toluene, ethylbenzene, propylbenzene, methylpyridine, ethylpyridine, propylpyridine, butylpyridine, butenylpyridine, and pentenylpyridine.

The term "halogen" includes fluorine, chlorine, iodine and bromine.

The term "oxy" means an oxygen (O) atom. The term "thio" means a sulfur (S) atom. The term "oxo" means =O.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nomenclature used throughout this disclosure, the terminal portion of the designated side chain is described first followed by the adjacent functionality toward the point of attachment. For example, a $C_{1-6}$ alkyl substituted with $C_{1-5}$ alkyl-carbonylamino is equivalent to

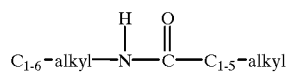

When a substituent includes the definition $C_0$ (e.g., aryl $C_{0-8}$ alkyl), the group modified by $C_0$ is not present in the substituent. Similarly, when any of the variables such as m or n is zero, the group modified by the variable is not present.

Compounds of the invention where X is a 5-membered monocyclic partially or fuilly saturated ring system, e.g., a thiazole system, can be prepared by forming an alkyl ester substituted derivative of the ring, e.g., methyl 4-(2-aminothiazol-4-yl)butanoate, forming the corresponding acid with HCl, and reacting with an amine to form the final product.

Compounds of the invention where X is a 6-membered monocyclic partially or fully saturated ring system, e.g., a pyridine system, can be prepared using 2-aminopyridine, 2-aminopicoline, 4-vinyl pyridine, etc., as described in Schemes 3, 4, and 10.

Compounds of the invention where X is a 9-membered polycyclic partially or fully saturated fused ring system can be prepared by reacting a substituted 5-membered ring starting material such as 2-amino-3-bromo thiophene, 2-nitro-3-bromo thiophene, 2-amino-3-bromo pyrrole, and 2-amino-3-bromo furan, with an appropriate compound under suitable ring closure conditions to effect formation of the 9-membered fused ring system.

Compounds of the invention where X is a 10-membered polycyclic partially or fully saturated ring system can be prepared using a starting material such as naphthyridin (Hamada, Y. et al., *Chem. harm. Bull. Soc.*, 1971, 19(9), 1857–1862), or by reacting an minoaldehyde pyridine with a suitable ketone under suitable ring closure conditions to effect formation of the 10-membered fused ring system.

The examples illustrate procedures for preparing compounds of the invention where Y is —(CH$_2$)$_{0-4}$, —O—, and —N(R$^8$)—. To make compounds where Y is —N(R$^8$)C(O)—, an acid such as compound 1-4 can be subjected to a Curtius reaction to form the amine, and subsequent condensation to give the final product.

In the schemes and examples below, various reagent symbols have the following meanings:
BOC or Boc: t-butyloxycarbonyl
Pd-C: Palladium on activated carbon catalyst
DMF: Dimethylformamide
DMSO: Dimethylsulfoxide
CH$_2$Cl$_2$: Methylene chloride
EtOH: ethanol
MeOH: methanol
EtOAc: ethyl acetate
HOAc: acetic acid
BOP: Benzotriazol-1-yloxytris(dimethylamino) phosphonium, hexafluorophosphate
EDC: 1-(3-Dimethylaminopropyl)-3-ethylcarbodiimide hydrochloride
LDA: Lithium diisopropylamide
PYCLU: Chloro-N,N,N',N'-bis(pentamethylene) formamidinium hexafluorophosphate
NMM: N-methylmorpholine
HOBT: 1-hydroxybenzotriazole hydrate
TFA: trifluoroacetic acid
NaOH: sodium hydroxide
SOCl$_2$: thionyl chloride
H$_2$SO$_4$: sulfuric acid
NaH: sodium hydride
LiOH: lithium hydroxide
THF: tetrahydrofuran
CH$_3$CN: acetonitrile
KHSO$_4$: potassium hydrogen sulfate
MgSO$_4$: magnesium sulfate
Boc$_2$O: di-t-butyl dicarbonate
ClCH$_2$CH$_2$Cl: dichloroethane
9-BBN: (9-borabicyclo[3.3.1]nonane)
TEA or NEt$_3$: triethylamine
Cs$_2$CO$_3$: cesium carbonate
CH$_3$NH$_2$: methylamine
NMP: N-methylpyrrolidinone
BrCH$_2$CO$_2$tBu: tertbutylbromoacetate
iPr$_2$NEt: diisopropylethylamine
NaN(TMS)$_2$: sodium hexamethyldisilazide
BocNHCH$_2$COOH:N-tert-butyloxycarbonylglycine In the methods of the present invention, the compounds described above can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, ocular or intramuscular form, all using forms well known to those of ordinary skill in the pharmaceutical arts. An effective but non-toxic amount of the compound desired can be employed as an $\alpha v\beta 5$ antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–50 mg/kg/day and more preferably 0.01–20 mg/kg/day, e.g. 0.1 mg/kg/day, 1.0 mg/kg/day, 5.0 mg/kg/day, or 10 mg/kg/day. A once-a-day oral dosage is, for example, 10 mg, 100 mg or 500 mg.

Intravenously, the most preferred doses will range from about 1 to about 10 mg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In ocular formulations such as eyedrops (e.g. aqueous solutions), from about 0.01–5.0% (w/v) of active ingredient can be employed, e.g., from about 0.01–2.0% (w/v) of active ingredient. Suitable eyedrop volume is, for example, 20, 30, 35, 50 or 100 $\mu$l. The objective is to administer a dose of between about 0.005–0.5 mg/kg per day to each eye, for a total dosage of between about 0.01–1.0 mg/kg/day, e.g. a dose of about 0.05 mg/kg per day to each eye, for a total dosage of about 0.1 mg/kg/day. For example, the eyedrops can be used to provide doses of 1 mg, 10 mg, or 50 mg. These dosage values are based on known and presently understood pharmacology of compounds of the invention. Dosage requirements are variable and must be individualized on the basis of the disease and the response of the patient.

Suitable eyedrop formulations are those which are isotonic and maintain sufficient contact with the eye surface to systemically deliver the active agent to the patient. Such formulations advantageously have a pH approximating neutrality and are non-irritating to the eye, e.g. they do not induce tearing and consequential flow of active agent out of the eye. Pharmaceutically acceptable carriers are, for example, water, mixtures of water and water-miscible solvents such as lower alkanols or arylalkanols, vegetable oils, polyalkylene glycols, petroleum based jelly, ethyl cellulose, hydroxy ethyl cellulose, ethyl oleate, carboxymethylcellulose, polyvinylpyrrolidone, isopropyl myristate and other conventionally-employed non-toxic, pharmaceutically acceptable organic and inorganic carriers.

The pharmaceutical preparation may also contain non-toxic auxiliary substances such as emulsifying, preserving, wetting agents, bodying agents and the like, as for example, polyethylene glycols 200, 300, 400 and 600, carbowaxes 1000, 1500, 4000, 6000 and 10000, antibacterial compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

In the procedure for making eyedrops, formulations are rendered sterile by appropriate means, such as starting the preparation procedure with sterile components and proceeding under sterile conditions, irradiating or autoclaving the finished formulation, and the like. Suitable anti microbial agents are also useful for maintaining sterility of the eyedrop.

The ocular preparation may also be a solid insert such as one which, after dispensing the compound, remains essentially intact, or a bioerodible insert that is soluble in lacrimal fluids, or otherwise disintegrates. For example, one may use a solid water soluble polymer as the carrier for the compound. The polymer used to form the insert may be any water soluble non-toxic polymer, for example, cellulose derivatives such as methylcellulose, sodium carboxymethyl cellulose, hydroxyethylcellulose, hydroxypropylcellulose, hydroxypropylmethyl cellulose, acrylates such as polyacrylic acid salts, ethylacrylates, polyacrylamides, natural products such as gelatin, alginates, pectins, tragacanth, karaya, chondrus, agar, acacia, starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol, gellan gum and xanthan gum, and mixtures of said polymers.

The ocular preparation may also be an ointment which is compounded, for example, by mixing finely milled powdered ingredients with a small amount of white petrolatum and levigating or otherwise mixing until a uniform distribution is achieved. The balance of white petrolatum is added by geometric addition until the desired dosage form is made.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

In the methods of the present invention, the compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

In the methods of the present invention, the compounds may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The present invention is also directed to the use of the compounds defined above with one or more agents useful in the prevention or treatment of osteoporosis. For example, the compounds of the instant invention may be effectively administered in combination with effective amounts of other agents used in the treatment of osteoporosis such as bisphosphonate bone resorption inhibitors; preferably, the bone resorption inhibitor is the bisphosphonate alendronate, now sold as FOSAMAX®. Preferred combinations are simultaneous or alternating treatments of an αvβ3 receptor antagonist of the present invention and FOSAMAX®.

In addition, the compounds may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of the compounds with a growth hormone secretagogue, optionally including a third component comprising FOSAMAX®.

In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

The compounds described above were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

SCHEME 1

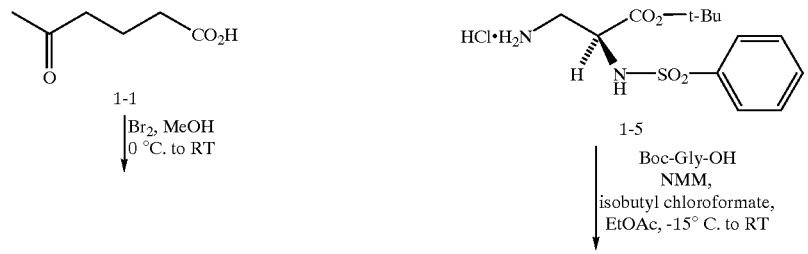

-continued

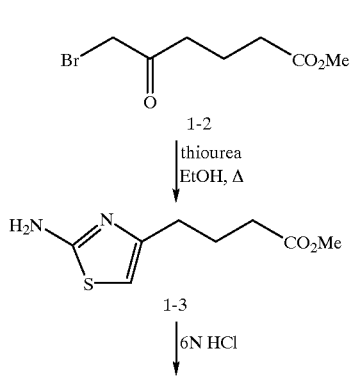

1-2

| thiourea
| EtOH, Δ

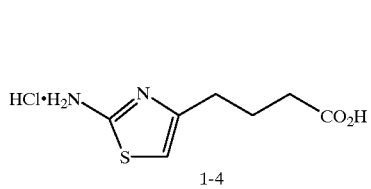

1-3

| 6N HCl

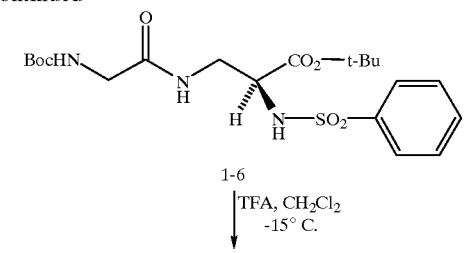

1-6

| TFA, CH$_2$Cl$_2$
| -15° C.

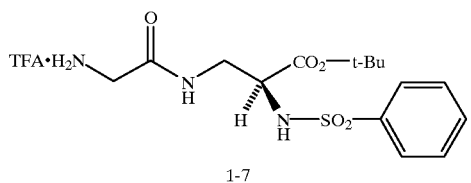

1-7

EDC, HOBT, NMM
DMF, -15° C. to RT

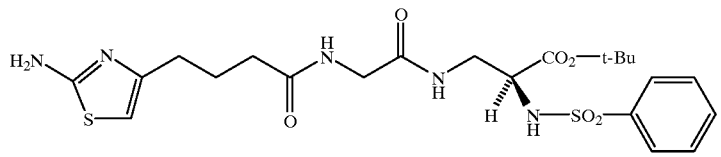

1-8

| TFA, CH$_2$Cl$_2$

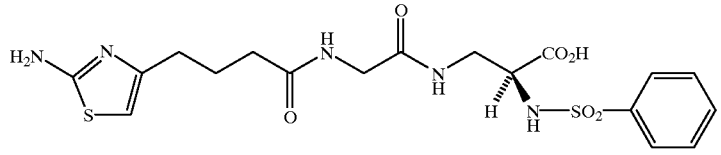

1-9

Br—CH$_2$—C(=O)—CH$_2$CH$_2$CH$_2$—CO$_2$CH$_3$ 1-2

Methyl 6-bromo-5-oxohexanoate (1-2)

5-Oxohexanoic acid (1-1, 5 mL, 42 mmol) was dissolved in 84 mL MeOH and cooled to 0° C. Br$_2$ (2.2 mL, 43 mmol) was added dropwise, and the reaction was stirred at RT overnight. After removing the MeOH by rotary evaporation, the residue was dissolved in ether, washed with water, sat. NaHCO$_3$ and brine, dried (Na$_2$SO$_4$), filtered and concentrated. Flash chromatography (silica, 10% EtOAc/hexane) provided the bromide-ester 1-2 as a yellow oil.

TLC R$_f$ 0.09 (silica, 15% EtOAc/hexane)

$^1$H-NMR (300 MHz, CDCl$_3$): δ3.88 (s, 2H), 3.67 (s, 3H), 2.75 (t, J=7 Hz, 2H), 2.37 (t, J=7 Hz, 2H), 1.94 (qn, J=7 Hz, 2H).

1-3

H$_2$N—[thiazole]—CH$_2$CH$_2$CH$_2$—CO$_2$CH$_3$

Methyl 4-(2-aminothiazol-4-yl)butanoate (1-3)

Bromide 1-2 (3.45 g, 15.5 mmol) and thiourea (1.4 g, 18 mmol) were combined in 77 mL EtOH and heated to reflux. After disappearance of 1-2 the EtOH was removed by rotary evaporation and the residue was diluted with EtOAc, washed with water and brine, then dried (MgSO$_4$), filtered and concentrated. The pH of the aqueous phase was adjusted to 7, and the solution was re-extracted with EtOAc (2×). These organic extracts were washed with brine, dried (MgSO$_4$), filtered and concentrated, combined with the first organic residues, then purified by flash chromatography (silica, EtOAc) providing aminothiazole 1-3 as a white solid.

TLC $R_f$ 0.5 (silica, EtOAc)

$^1$H-NMR (400 MHz, CDCl$_3$): δ6.09 (s, 1H), 5.19 (br s, 2H), 3.66 (s, 3H), 2.55 (t, J=7 Hz, 2H), 2.34 (t, J=7 Hz, 2H), 1.96 (qn, J=7 Hz, 2H).

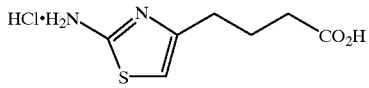

1-4

4-(2-Aminothiazol-4-yl)butanoic acid hydrochloride (1-4)

Ester 1-3 (1.3 g, 6.5 mmol) was dissolved in 32 mL 6 N HCl. After stirring overnight, the resulting suspension was concentrated, providing acid 1-4 as a white solid.

$^1$H-NMR (400 MHz, d$_6$-DMSO): δ9.12 (br s, 1H), 6.51 (s, 1H), 3.50 (br s), 2.51 (t, J=7 Hz, 2H), 2.24 (t, J=7 Hz, 2H), 1.77 (qn, J=7 Hz, 2H).

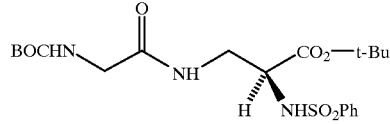

1-6

N-Boc-glycyl-2(S)-ohenylsulfonamido-β-alanine t-butyl ester (1-6)

N-Boc-glycine (255 mg, 1.5 mmol) was dissolved in 7.4 mL EtOAc, cooled to −15° C., then NMM (179 μL, 1.6 mmol) and isobutyl chloroformate (211 μL, 1.6 mmol) were added. After 20 min, amine 1-5 (500 mg, 1.5 mmol) and additional NMM (422 μL, 3.2 mmol) were added and the reaction was warmed to RT overnight. Following dilution with EtOAc, the mixture was washed with water, sat. NaHCO$_3$, 10% KHSO$_4$, and brine, dried (MgSO$_4$), filtered and concentrated, providing amide 1-6 as a white solid.

TLC $R_f$ 0.73 (silica, EtOAc)

$^1$H-NMR (300 MHz, CDCl$_3$): δ7.84 (d, J=7 Hz, 2H), 7.59 (ABX t, J=7 Hz, 1H), 7.51 (ABX t, J=7 Hz, 2H), 6.58 (br m, 1H), 5.58 (d, J=8 Hz, 1H), 5.11 (br s, 1H), 3.90–3.78 (m, 3H), 3.72 (m, 1H), 3.40 (m, 1H), 1.48 (s, 9H), 1.28 (s, 9H).

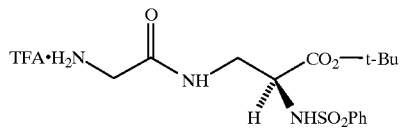

1-7

Glycyl-2(S)-phenylsulfonamido-β-alanine t-butyl ester trifluoroacetate salt (1-7)

Protected amide 1-6 (576 mg, 1.26 mmol) was dissolved in 6.3 mL CH$_2$Cl$_2$, cooled to −15° C., and TFA (6.3 mL) was added. After 25 min the reaction was concentrated, providing amine 1-7.

TLC $R_f$ 0.36 (silica, 9:1:1 CH$_2$Cl$_2$/MeOH/HOAc).

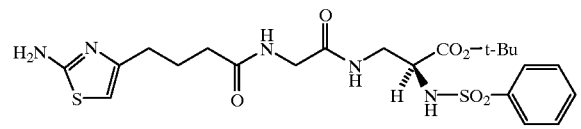

1-8

4-(2-Aminothiazol-4-yl)butanoyl-glycyl-2(S)-phenylsulfonamido-β-alanine t-butyl ester (1-8)

Acid 1-4 (300 mg, 1.35 mmol), amine 1-7 (600 mg, 1.37 mmol), HOBT (219 mg, 1.14 mmol) and NMM (445 μL, 4.04 mmol) were combined in 13 mL DMF, cooled to −15° C., and EDC (310 mg, 1.61 mmol) was added. The reaction was warmed to RT, stirred overnight, then diluted with EtOAc, washed with water, sat. NaHCO$_3$, and brine, dried (MgSO$_4$), filtered and concentrated. Flash chromatography (silica, 20% MeOH/EtOAc) provided 1-8 as yellow solid.

TLC $R_f$ 0.55 (silica, 20% MeOH/EtOAc)

$^1$H-NMR (400 MHz, CDCl$_3$): δ7.80 (d, J=7 Hz, 2H), 7.55 (ABX t, J=7 Hz, 1H), 7.47 (ABX t, J=8 Hz, 2H), 7.35 (br s, 1H), 7.04 (br m, 1H), 6.12 (s, 1H), 5.41 (br s, 2H), 4.05–3.95 (m, 3H), 3.69 (m, 1H), 3.39 (ddd, 1H), 2.70–2.55 (m, 2H), 2.33 (m, 2H), 2.01 (qn, J=7 Hz, 2H), 1.27 (s, 9H).

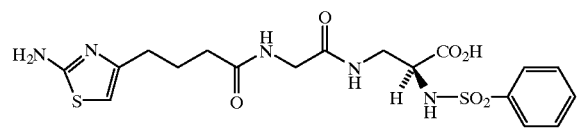

1-9

4-(2-Aminothiazol-4-yl)butanoyl-glycyl-2(S)-phenylsulfonamido-β-alanine (1-9)

Ester 1-8 (365 mg, 0.69 mmol) was dissolved in CH$_2$Cl$_2$ (3.5 mL), then TFA (3.5 mL) was added. After 5 h the reaction mixture was concentrated, azeotroped with toluene, then purified by sequential flash chromatography (silica, 22:20:1:1 EtOAc/EtOH/H$_2$O/NH$_4$OH, then silica, 4:1:1 CH$_2$Cl$_2$/MeOH/HOAc, then 7:1:1 CH$_2$Cl$_2$/MeOH/HOAc), providing 1-9 as a white solid.

TLC $R_f$ 0.33 (silica, 7:1:1 CH$_2$Cl$_2$/MeOH/HOAc)

$^1$H-NMR (400 MHz, CD$_3$OD): δ7.86 (d, J=7 Hz, 2H), 7.58 (ABX t, J=7 Hz, 1H), 7.52 (ABX t, J=8 Hz, 2H), 6.27 (s, 1H), 3.89 (AB d, J=17 Hz, 1H), 3.77 (AB d, J=17 Hz, 1H), 3.64 (t, J=6 Hz, 1H), 3.53 (AB dd, 1H), 3.41 (AB dd, 1H), 2.57 (t, J=7 Hz, 2H), 2.35–2.25 (m, 2H), 1.95 (m, 2H).

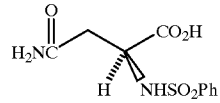

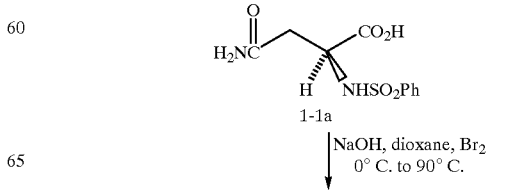

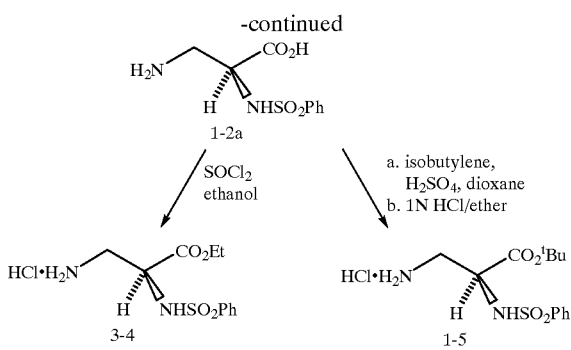

N-Phenlsulfonyl-L-aslparane (1-1a)

To a stirred solution of L-asparagine (Aldrich) (10 g, 76 mmol), NaOH (3.4 g, 85 mmol), H$_2$O (50 mL), and dioxane (50 mL) at 0° C. was added PhSO$_2$Cl (10.6 mL, 84 mmol). After 1 min, NaOH (3.4 g) in H$_2$O (50 mL) was added and the reaction mixture stirred for 30 min. The reaction mixture was then concentrated to remove the dioxane then washed with EtOAc. The aqueous phase was then cooled to 0° C. and acidified to pH 5.0 with conc. HCl to effect product precipitation. The resulting solid was collected by filtration, washed with H$_2$O (20 mL) and dried at 50° C. under vacuum to give N-phenylsulfonyl-L-asparagine (1-1a) as a white solid.

R$_f$ 0.40 (silica, 10:1:1 ethanol/H$_2$O/NH$_4$OH). $^1$H NMR (300 MHz, D$_2$O) δ7.59 (m, 2H), 7.26 (m, 3H), 3.92 (m, 1H), 3.02 (m, 1H), 2.35 (m, 1H).

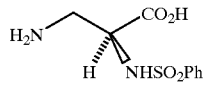

3-Amino-2(S)-phenylsulfonylaminopropionic acid (1-2b)

To stirred solution of NaOH (15.6 g, 0.4 mol) in H$_2$O (70 mL), cooled with an icebath, was added bromine (3.6 mL, 0.07 mol) dropwise. After 5 min, a cold solution of N-phenylsulfonyl-L-asparagine, 1-1a (14.6 g, 54 mmol) and NaOH (4.3 g, 0.1 mol) in H$_2$O (50 mL) was added in one portion. The solution was stirred for 20 min at 0° C. then 30 min at 90° C. The reaction mixture was recooled to 0° C., and the pH adjusted to 7 through dropwise addition of conc. HCl. The white precipitate formed was collected by filtration and then dried to give (1-2b) as a white solid.

$^1$H NMR (300 MHz, D$_2$O) δ8.00, 7.50 (m, 5H), 3.88 (m, 1H), 3.37 (m, 1H), 3.12 (m, 1H).

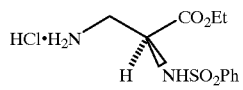

Ethyl 3-Amino-2(S)-phenylsulfonylaminopropionate hydrochloride (3-4)

Amino acid 1-2a (1.0 g, 4.1 mmol) was suspended in 20 mL EtOH, cooled to 0° C., and SOCl$_2$ (1.5 mL, 21 mmol) was added dropwise. After stirring at RT overnight the mixture was concentrated, triturated with Et$_2$O (2×), and dried, providing 3-4 (1.26 g) as a hygroscopic yellow solid.

$^1$H-NMR (300 MHz, d$_6$-DMSO): δ8.30 (br s), 7.79 (d, J=8 Hz, 2H), 7.70–7.60 (m, 3H), 4.21 (t, J Hz, 1H), 3.90–3.80 (m, 2H), 3.09 (ABX dd, J=13, 6 Hz, 1H), 2.90 (ABX dd, J=13, 8 Hz, 2H), 0.97 (t, J=7 Hz, 3H).

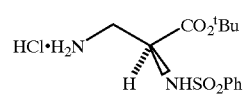

tert-Butyl 3-Amino-2(S)-phenylsulfonylaminopropionate hydro-chloride (1-5)

In a Fischer-Porter tube, a mixture of 1-2a (10.2 g, 42 mmol) and DME (150 mL) was sequentially treated with H$_2$SO$_4$ (6.4 mL, 0.12 mol), cooled to –78° C., and then condensed isobutylene (75 mL). The cooling bath was removed. After 24 h, ice/water (250 mL) was added followed by washing with ether (2×). The aqueous phase was basified with aq 6N NaOH, then saturated with NaCl, followed by extraction with EtOAc (3×). The combined extracts were washed with brine, dried (MgSO$_4$), and concentrated to give a white solid. This was dissolved in CH$_2$Cl$_2$ and treated with 1N HCl/ether (22 mL), and then concentrated to give 1-5 as a glassy yellow solid.

$^1$H NMR (400 MHz, DMSO) δ8.25–8.00 (m, 4H), 7.85–7.58 (m, 5H), 4.08 (m, 1H), 3.10 (m, 1H), 2.73 (m, 1H), 1.17 (s, 9H).

SCHEME 2

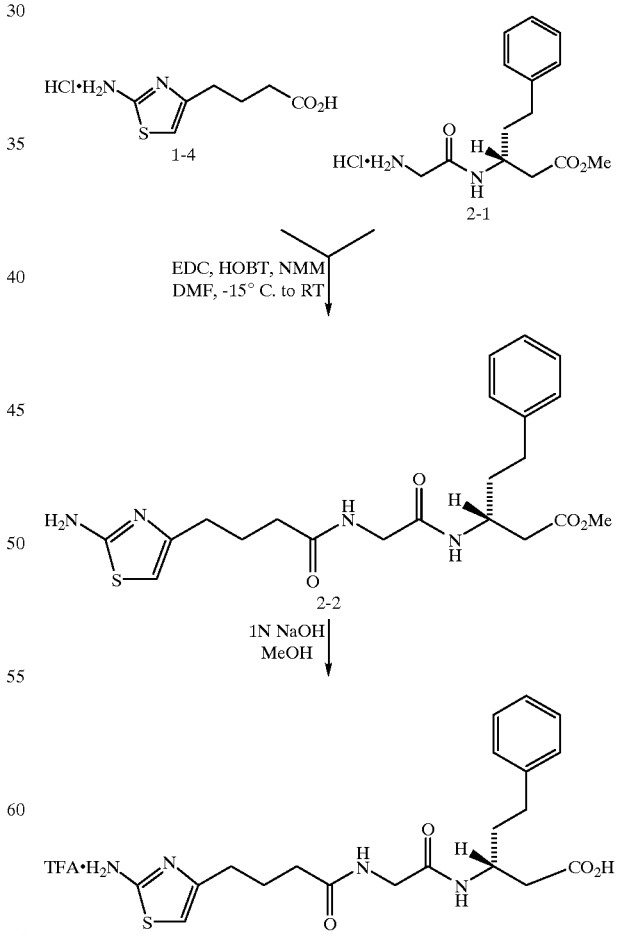

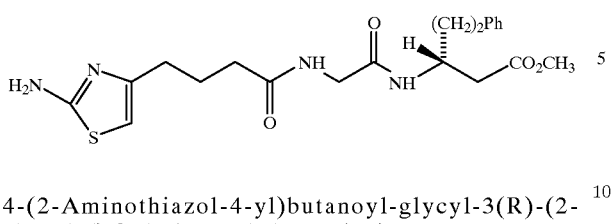

2-2

4-(2-Aminothiazol-4-yl)butanoyl-glycyl-3(R)-(2-phenethyl)-β-alanine methyl ester (2-2)

Acid 1-4 (300 mg, 1.35 mmol), amine 2-1 (405 mg, 1.35 mmol) (prepared as described in Duggan et al., U.S. Pat. No. 5,264,420) HOBT (219 mg, 1.62 mmol) and NMM (445 μL, 4.04 mmol) were combined in 7 mL DMF, cooled to −15° C., and EDC (310 mg, 1.61 mmol) was added. The reaction was warmed to RT, stirred overnight, then diluted with EtOAc, washed with water, sat. NaHCO$_3$, and brine, dried (MgSO$_4$), filtered and concentrated. Flash chromatography (silica, 10% MeOH/EtOAc) provided 2-2 as a yellow oil.

TLC R$_f$ 0.32 (silica, 10% MeOH/EtOAc)

$^1$H-NMR (400 MHz, CDCl$_3$): δ7.82 (d, J=7 Hz, 1H), 7.65 (d, J=8 Hz, 1H), 7.40–7.10 (m, 5H), 6.93 (d, J=8 Hz, 1H), 6.10 (s, 1H), 4.31 (m, 1H), 3.96 (ABX dd, J=17, 6 Hz, 1H), 3.89 (ABX dd, J=17, 5 Hz, 1H), 3.64 (s, 3H), 2.68–2.54 (m), 2.32–2.17 (m, 2H), 2.25–1.80 (m).

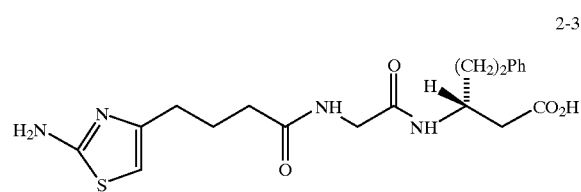

2-3

4-(2-Aminothiazol-4-yl)butanoyl-glycyl-3(R)-(2-phenethyl)-β-alanine trifluoroacetate salt (2-3)

Ester 2-2 (220 mg, 0.51 mmol) and 1 N NaOH (1.3 mL, 1.3 mmol) were combined in 5 mL MeOH. Mter 3 d the reaction mixture was concentrated, purified by flash chromatography (silica, 9:1:1 CH$_2$Cl$_2$/MeOH/HOAc), then preparative HPLC (C$_{18}$, 0.1% TFA in CH$_3$CN/H$_2$O), providing, after lyophilization, acid 2-3 as a white solid.

TLC R$_f$ 0.54 (silica, 4:1:1 CH$_2$Cl$_2$/MeOH/HOAc)

$^1$H-NMR (400 MHz, CD$_3$OD): δ7.26–7.10 (m, 5H), 6.52 (s, 1H), 4.23 (m, 1H), 3.88 (AB d, J=17 Hz, 1H), 3.79 (AB d, J=17 Hz, 1H), 2.72–2.55 (m, 4H), 2.51 (d, J=7 Hz, 2H), 2.34 (t, J=7 Hz, 2H), 1.99–1.75 (m, 4H).

SCHEME 3

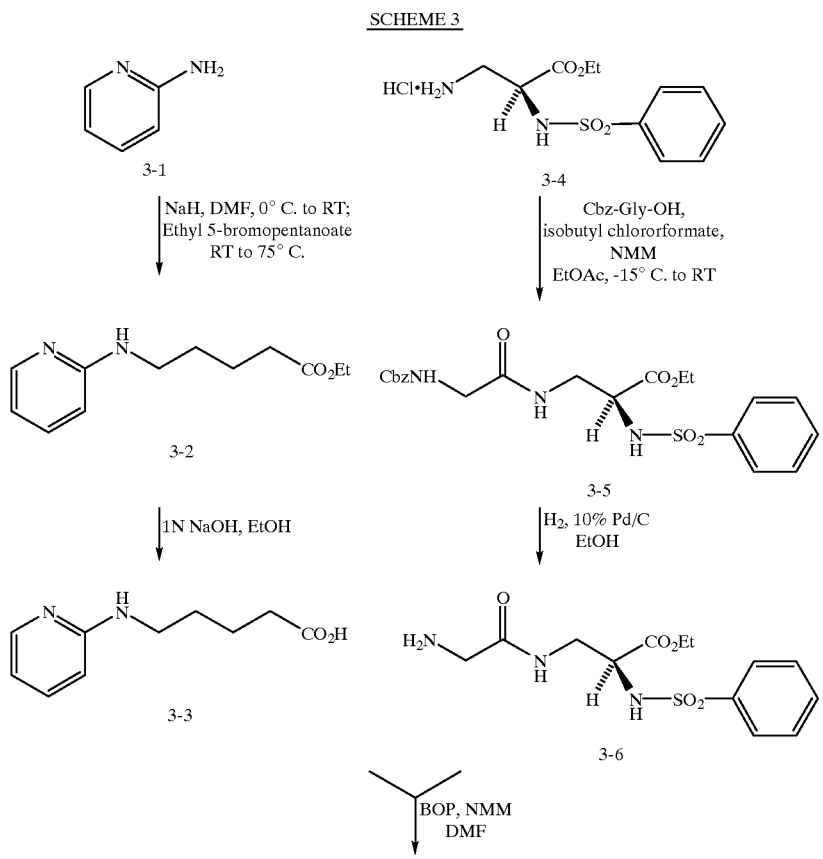

-continued

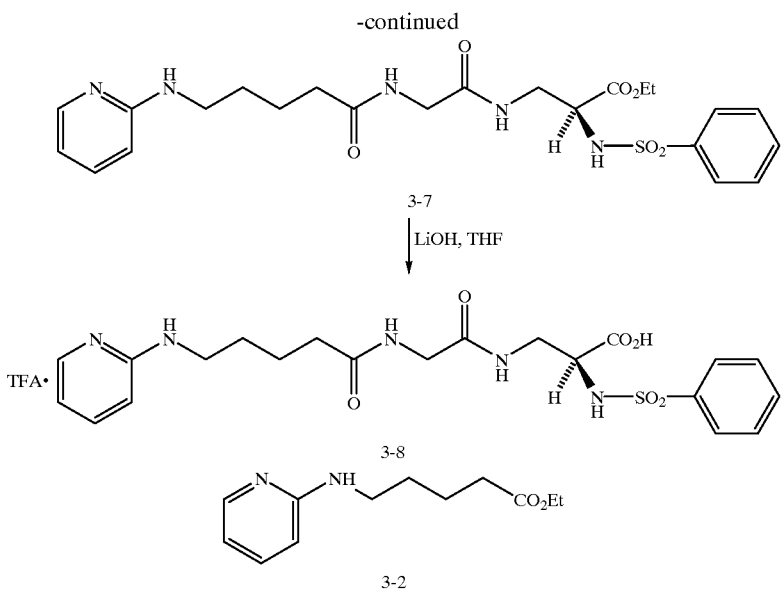

Ethyl 5-(2-pyridylamino)pentanoate (3-2)

2-Aminopyridine (3-1, 1.97 g, 20.9 mmol) in 10 mL DMF was added to a suspension of NaH (60% in oil, 1.00 g, 25 mmol) in 80 mL DMF cooled to 0° C. After warming to RT for 45 min, ethyl 5-bromopentanoate (4.2 mL, 25 mmol) was added dropwise. This mixture was heated at 75° C. overnight, then cooled to RT, diluted with EtOAc, washed with water (2×), sat. NaHCO$_3$, and brine, dried (MgSO$_4$), filtered and concentrated. Flash chromatography (silica, 50% then 70% EtOAc/hexane) provided 3-2 as a yellow oil.

TLC R$_f$ 0.55 (silica, 70% EtOAc/hexane)

$^1$H-NMR (400 MHz, CDCl$_3$): δ8.07 (dd, J=5, 1 Hz, 1H), 7.40 (m, 1H), 6.55 (m, 1H), 6.37 (d, J=8 Hz, 1H), 4.48 (br s, 1H), 4.13 (q, J=7 Hz, 2H), 3.29 (q, J=7 Hz, 2H), 2.35 (t, J=7 Hz, 2H), 1.80–1.55 (m, 4H), 1.25 (t, J=7 Hz, 3H).

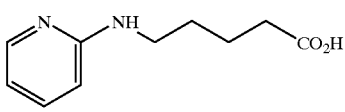

3-3

5-(2-Pyridylamino)p)entanoic acid (3-3)

Ester 3-2 (0.41 g, 1.84 mmol) was dissolved in 18 mL EtOH, 1 N NaOH (4.6 mL, 4.6 mmol) was added, and the reaction was stirred overnight. The pH of the solution was adjusted to 7 with 1 N HCl, and concentration provided a white solid containing acid 3-3 and NaCl.

TLC R$_f$ 0.06 (silica, 19:1:1 CH$_2$Cl$_2$/MeOH/HOAc)

$^1$H-NMR (400 MHz, D$_2$O): δ7.81 (m, 1H), 7.77 (d, J=6 Hz, 1H), 6.96 (d, J=9 Hz, 1H), 6.82 (t, J=7 Hz, 1H), 3.36 (t, J=7 Hz, 2H), 2.24 (m, 2H), 1.72–1.50(m, 4H).

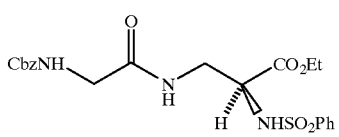

3-5

N—Cbz-glycyl-2(S)-phenylsulfonamido-β-alanine ethyl ester (3-5)

N—Cbz-glycine (339 mg, 1.62 mmol) was dissolved in 8 mL EtOAc, cooled to −15° C., then NMM (196 μL, 1.8 mmol) and isobutyl chloroformate (230 μL, 1.8 mmol) were added. After 20 min, the mixed anhydride solution was added to amine 3-4 (0.50 mg, 1.6 mmol) suspended in 5 mL EtOAc and the reaction was warmed to RT for 90 min. Following dilution with EtOAc, the mixture was washed with water, sat. NaHCO$_3$, 5% KHSO$_4$, and brine, dried (MgSO$_4$), filtered and concentrated. Flash chromatography (silica, 75% EtOAc/hexane) provided amide 3-5 as a colorless oil.

TLC R$_f$ 0.29 (silica, 75% EtOAc/hexane)

$^1$H-NMR (300 MHz, CDCl$_3$): δ7.65–7.45 (m, 3H), 7.40–7.25 (m, 5H), 6.68 (t, J=6 Hz, 1H), 5.83 (d, J=8 Hz, 1H), 5.49 (t, J=6 Hz, 1H), 5.15 (s, 2H), 4.04– 3.95 (m, 3H), 3.89–3.85 (m, 2H), 3.73 (m, 1H), 3.46 (m, 1H), 1.11 (t, J=7 Hz, 3H).

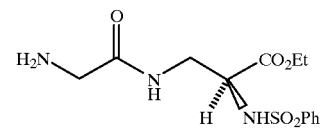

3-6

Glycyl-2(S)-phenylsulfonamido-β-alanine ethyl ester (3-6)

Protected amine 3-5 (0.47 g, 1.01 mmol) was dissolved in 10 mL EtOH, 10% Pd/C (94 mg) was added, and the reaction was stirred under an H$_2$ balloon. After 4 h, additional 10% Pd/C was added (94 mg), and the reaction was continued for 3 d. The mixture was filtered through Celite, concentrated, and azeotroped with CHCl$_3$, providing amine 3-6 as a gum.

$^1$H-NMR (300 MHz, CDCl$_3$): δ7.95 (m), 7.86 (d, J=7 Hz, 2H), 7.60–7.45 (m, 3H), 4.05 (dd, J=5, 6 Hz 1H), 3.96 (q, J=7 Hz, 2H), 3.80–3.55 (m), 1.07 (t, J=7 Hz, 3H).

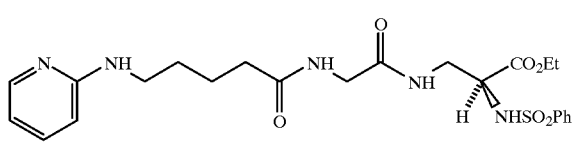

3-7

5-(2-Pyridylamino)pentanoylglycyl-2(S)-phenylsulfonamido-β-alanine ethyl ester (3-7)

Acid 3-3 (186 mg, 0.55 mmol), amine 3-6 (150 mg, 0.46 mmol), NMM (0.20 mL, 1.8 mmol) and BOP (302 mg, 0.68 mmol) were combined in 3 mL DMF. After 5 d the DMF was removed on a rotary evaporator, the residue was diluted with EtOAc, then washed with water, sat. NaHCO₃, and brine, dried (MgSO₄), filtered and concentrated. Flash chromatography (silica, 25% i-PrOH/EtOAc) provided 3-7 as a colorless oil.

TLC $R_f$ 0.30 (silica, 25% i-PrOH/EtOAc)

¹H-NMR (400 MHz, CDCl₃): δ8.05 (d, J=4 Hz, 1H), 7.85 (d, J=7 Hz, 2H), 7.57 (t, J=7 Hz, 1H), 7.55–7.45 (m, 2H), 7.42 (m, 1H), 6.80 (br t, 1H), 6.54 (dd, J=6, 4 Hz, 1H), 6.45 (m, 1H), 6.39 (d, J=8 Hz, 1H), 5.19 (m, 1H), 4.16 (ABX dd, J=17, 7 Hz, 1H), 4.08–3.95 (m), 3.85–3.75 (m, 2H), 3.29 (q, J=6 Hz, 2H), 2.40–2.32 (m, 2H), 1.85 (m, J=7 Hz, 2H), 1.75 (m, 2H), 1.10 (t, J=7 Hz, 3H).

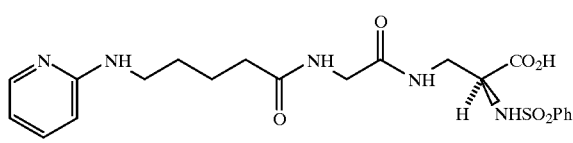

3-8

5-(2-Pyridylamino)pentanoylglycyl-2(S)-phenylsulfonamido-β-alanine trifluoroacetate salt (3-8)

Ester 3-7 (59 mg, 0.12 mmol) was dissolved in 1 mL THF, then 1 N LiOH (0.29 mL, 0.29 mmol) was added. After stirring overnight the reaction was concentrated, the mixture was concentrated. Flash chromatography (silica, 22:20:1:1 EtOAc/EtOH/H₂O/NH₄OH), followed by prep. HPLC (C-18, 0.1% TFA/CH₃CN/H₂O) and lyophilization provided 3-8 as a white solid.

TLC $R_f$ 0.26 (silica, 22:20:1:1 EtOAc/EtOH/H₂O/NH₄OH)

¹H-NMR (400 MHz, D₂O): δ7.83–7.75 (m, 3H), 7.70 (d, J=6 Hz, 1H), 7.67 (d, J=7 Hz, 1H), 7.58 (t, J=7 Hz, 2H), 6.96 (d, J=9 Hz, 1H), 6.80 (t, J=7 Hz, 1H), 3.86–3.80 (m, 3H), 3.55 (dd, J=14, 4 Hz, 1H), 3.36 (m, 2H), 3.29 (dd, J=14, 8 Hz, 1H), 2.39 (m, 2H), 1.72 (m, 4H).

SCHEME 4

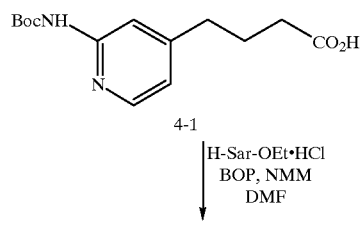

4-1

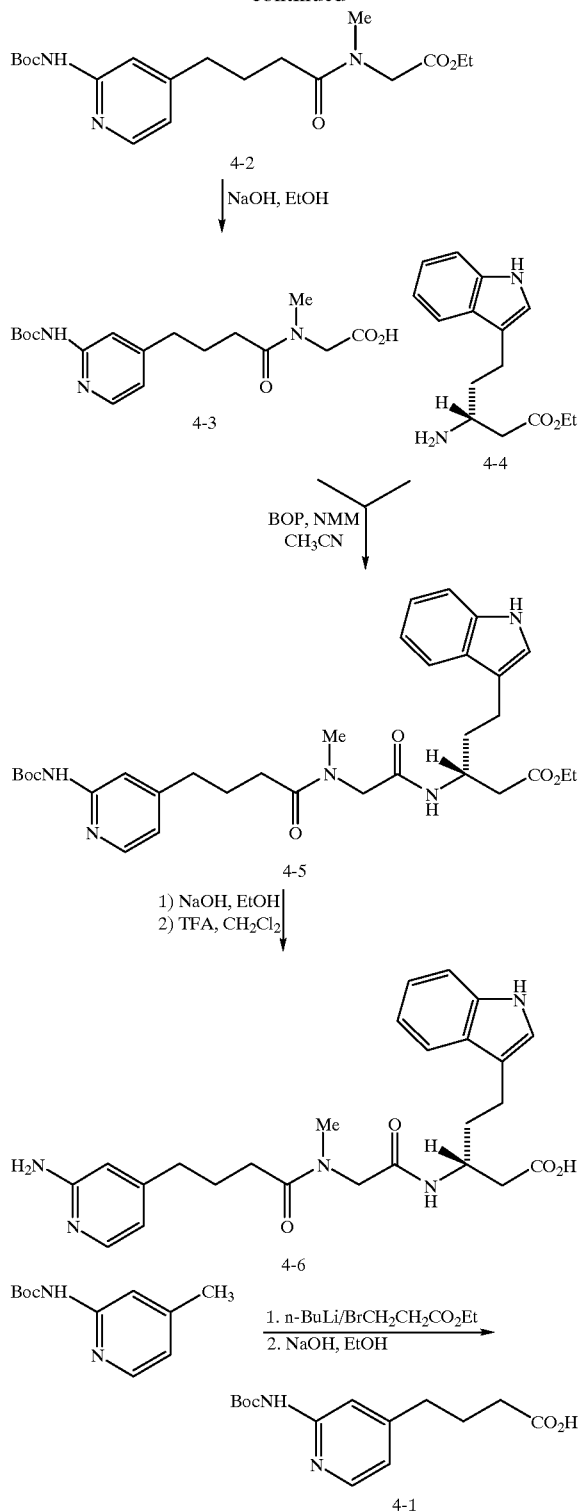

4-(2-N—Boc-aminopyridin-4-yl)butanoic acid (4-1)

The protected picoline (90 g, 0.43 mol) was dissolved in 3 L THF under N₂, cooled to −78° C., and n-BuLi (1.6 M, 675 mL, 1.08 mol) was added during 30 min. The mixture was allowed to warm to RT for 1 h, then the resulting orange suspension was cooled to −78° C. Methyl 3-bromopropionate (79 g, 0.47 mol) was added during 2 min. After 15 min the cooling bath was removed and the mixture was allowed to warm to −20° C. at which point it was quenched with 60 mL HOAc in 250 mL THF. The solution was diluted with 2L EtOAc, washed with water, sat. NaHCO$_3$, and brine, dried (MgSO$_4$). The aqueous layers were re-extracted with EtOAc (2×), and these organic layers were filtered, concentrated, and dissolved in 1.5 L EtOH and 1.5 L 1 N NaOH (1.5 mol). After 1 h the reaction was concentrated by 1/3, diluted with 4 L EtOAc, the aqueous layer was removed. The pH of the aqueous layer was adjusted to 4-5 with 10% KHSO$_4$, then extracted with EtOAc (2×3 L). The EtOAc layers were washed with brine, dried (MgSO$_4$), filtered and concentrated, providing 4-1 as a yellow oil.

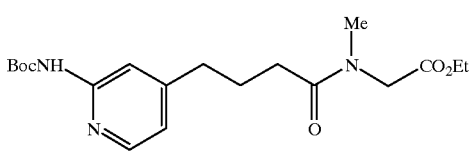

4-2

4-(2-Boc-amino-pyridin-6-yl)butanoyl-sarcosine ethyl ester (4-2)

Acid 4-1 (200 mg, 0.71 mmol), H—Sar—OEt. HCl (130 mg, 0.84 mmol), NMM (314 μL, 2.9 mmol) and BOP (378 mg, 0.86 mmol) were combined in 5 mL DMF. After stirring overnight the reaction mixture was diluted with EtOAc, washed with water (5×), sat. NaHCO$_3$, and brine, dried (MgSO$_4$), filtered and concentrated. Flash chromatography (silica, 50–70% EtOAc/hexane) provided 4-2 as a colorless oil.

TLC R$_f$ 0.54 (silica, 80% EtOAc/hexane)

$^1$H-NMR (400 MHz, CDCl$_3$): 4:1 mixture of amide rotomers, major rotomer δ8.12 (d, J=5 Hz, 1H), 7.79 (s, 1H), 7.48 (br s, 1H), 6.83 (d, J=6 Hz, 1H), 4.19 (q, J=7 Hz, 2H), 4.11 (s, 2H), 3.03 (s, 3H), 2.68 (t, J=7 Hz, 2H), 2.39 (t, J=7 Hz, 2H), 2.02 (qn, J=7 Hz, 2H), 1.53 (s, 9H) 1.26 (t, J=7 Hz, 3H).

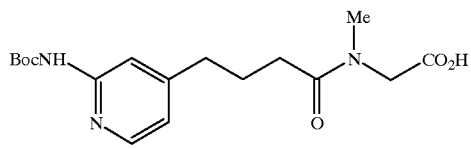

4-2

4-(2-Boc-amino-pyridin-4-yl)butanoyl-sarcosine (4-3)

Ester 4-2 (91 mg, 0.24 mmol) was dissolved in 2.4 mL EtOH, and 1 N NaOH (0.60 mL, 0.60 mmol) was added. After 45 min the mixture was concentrated, then diluted with EtOAc, washes with 10% KHSO$_4$ and brine, dried (MgSO$_4$) filtered and reconcentrated, providing acid 4-3 as a glass.

TLC R$_f$ 0.18 (silica, 18:1:1, CH$_2$Cl$_2$/MeOH/HOAc)

$^1$H-NMR (400 MHz, CDCl$_3$): 1:1 mixture of amide rotomers δ8.03–7.82 (m, 3H), 6.86 (br s, 1H), 4.15/3.96 (s, 2H), 3.06/3.02 (s, 3H), 2.75–2.65 (m, 2H), 2.40 (m, 2H), 2.22–2.00 (m, 2H), 1.53 (s, 9H).

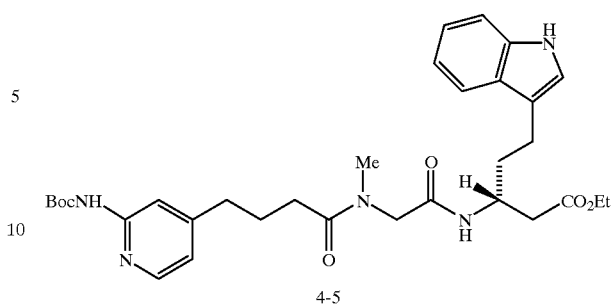

4-5

4-(2-Boc-amino-pyridin-4-yl)butanoyl-sarcosine-3(R)-[2-(indol-3-yl)ethyl]-alanine ethyl ester (4-5)

Acid 4-3 (84 mg, 0.24 mmol), amine 4-4 (see Duggan et al., U.S. Pat. No. 5,264,420) (68 mg, 0.26 mmol), NMM (104 μL, 0.95 mmol) and BOP (127 mg, 0.29 mmol) were combined in 2.4 mL CH$_3$CN. After stirring overnight the mixture was diluted with EtOAc, washed with water (4×), sat. NaHCO$_3$, and brine, dried (MgSO$_4$) and concentrated. Flash chromatography (silica, EtOAc) provided 4-5 as a colorless oil TLC R$_f$ 0.66 (silica, 20% MeOH/EtOAc)

$^1$H-NMR (400 MHz, CDCl$_3$): 4:1 mixture of amide rotomers, major rotomer δ8.12 (s, 1H), 8.09 (d, J=5 Hz, 1H), 7.78 (s, 1H), 7.55 (d, J=8 Hz, 1H), 7.39 (s, 1H), 7.34 (d, J=8 Hz, 1H), 7.17 (t, J=8 Hz, 1H), 7.08 (t, J=7 Hz, 1H), 7.03 (d, J=2 Hz, 1H), 6.79 (dd, J=5, 1 Hz, 1H), 6.71 (d, J=9 Hz, 1H), 4.32 (m, 1H), 4.16–4.05 (m, 3H), 4.00 (AB d, J=15 Hz, 1H), 3.94 (AB d, J=15 Hz, 1H), 3.04 (s, 3H), 2.77 (m, 2H), 2.63 (t, J=8 Hz, 2H), 2.53 (m, 2H), 2.36 (m, 2H), 2.02–1.90 (m, 4H), 1.53 (s, 9H), 1.22 (t, J=7 Hz, 3H).

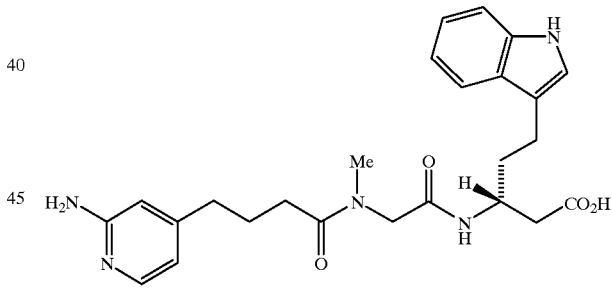

4-6

4-(2-Aminopyridin-4-yl)butanoyl-sarcosine-3(R)-[2-(indol-3-yl)ethyl]-β-alanine (4-6)

Ester 4-5 (20 mg, 34 μmol) was dissolved in 350 μL EtOH, then 1 N NaOH (85 μL, 85 μmol) was added. After 2 h the reaction was diluted with EtOAc, washed with 10% KHSO$_4$ and brine, dried (MgSO$_4$), filtered and concentrated. The residue was dissolved in 1 mL CH$_2$Cl$_2$, treated with 1 mL TFA for 1 h, then concentrated and azeotroped with toluene. Flash chromatography (silica, 50:1:1, EtOH/H$_2$O/NH$_4$OH) provided 4-6 as an off-white solid.

TLC R$_f$ 0.55 (silica, 20:1:1 EtOH/H$_2$O/NH$_4$OH)

$^1$H-NMR (400 MHz, CD$_3$OD): 2:1 mixture of amide rotomers δ7.72/7.67 (d, J=6 Hz, 1H), 7.52 (t, J=8 Hz, 1H), 7.30 (t, J=8 Hz, 1H), 7.07–6.90 (m, 4H), 6.55/6.54 (s, 1H), 6.49 (s, 1H), 4.36–4.25 (m, 1H), 4.14–3.93 (m, 2H), 3.06/2.93 (s, 3H), 2.60 (t, J=8 Hz, 2H), 2.55–2.45 (m, 4H), 2.34 (t, J=7 Hz, 1H), 2.05–1.84 (m).

SCHEME 5
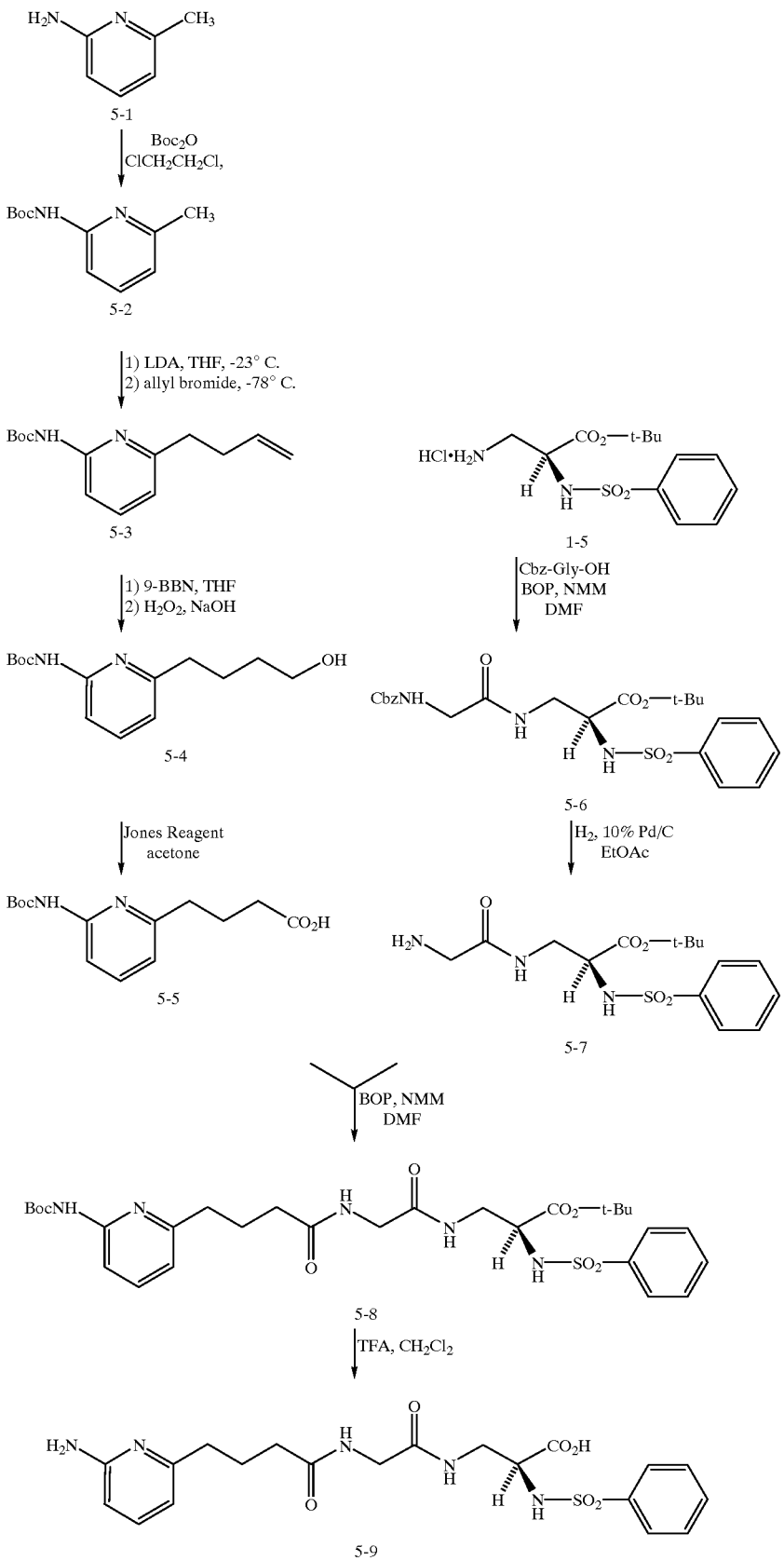

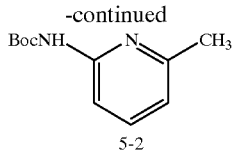

5-2

2-(Boc-amino)-6-methylpyridine (5-2)

2-Amino-6-picoline (5.0 g, 46.2 mmol) and Boc$_2$O (11.1 g, 50.8 mmol) were combined in 150 mL dichloroethane. After heating at reflux for 6 h, additional Boc$_2$O (2.0 g, 9.2 mmol) was added, and the reaction was heated overnight. After concentration, the reaction mixture was flash filtered (silica, CH$_2$Cl$_2$), providing 5-2 as a waxy solid.

TLC R$_f$ 0.21 (silica, CH$_2$Cl$_2$)

$^1$H-NMR (400 MHz, CDCl$_3$): δ7.70 (d, J=8 Hz, 1H), 7.54 (t, J=8 Hz, 1H), 7.19 (br s, 1H), 6.80 (d, J=7 Hz, 1H), 2.42 (s, 3H), 1.51 (s, 9H).

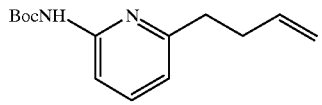

5-3

2-Boc-amino-6-(4-butenyl)pyripidine (5-3)

Methylpyridine 5-2 (4.0 g, 19.2 mmol) was dissolved in 40 mL THF, cooled to −23° C., and LDA (2 M, 24 mL, 48 mmol) was added dropwise. After 30 min the mixture was cooled to −78° C. and allyl bromide (2.49 mL, 2.88 mmol) was added dropwise. After 15 min more, the reaction was quenched with sat. NH$_4$Cl, warmed to RT, diluted with EtOAc, and the organic layer was washed with brine. After drying (MgSO$_4$), filtration and concentration, flash chromatography provided 5-3 as a yellow oil.

TLC R$_f$ 0.40 (silica, 75% CH$_2$Cl$_2$/hexane)

$^1$H-NMR (300 MHz, CDCl$_3$): δ7.72 (d, J=8 Hz, 1H), 7.56 (t, J=8 Hz, 1H), 7.16 (br s, 1H), 6.80 (d, J=7 Hz, 1H), 5.85 (m, 1H), 5.03 (dm, J=17 Hz, 1H), 4.97 (dm, J=10 Hz, 1H), 2.74 (t, J=7 Hz, 2H), 2.42 (qm, J=7 Hz, 2H), 1.52 (s, 9H).

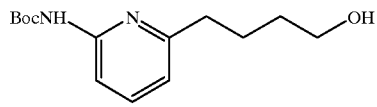

5-4

2-(Boc-amino)-6-(4-hydroxybutyl)pyridine (5-4)

A solution of alkene 5-3 (558 mg, 2.25 mmol) in 2 mL THF was added dropwise to a solution of 9-BBN (0.5 M in THF, 4.95 mL, 2.48 mmol). After stirring overnight, and additional portion of 9-BBN (0.5 M, 1.1 mL, 0.55 mmol) was added and the reaction was continued 1 h more. The reaction was quenched by the successive addition of EtOH (1.5 mL), 6 N NaOH (0.5 mL), and 30% H$_2$O$_2$ (1.0 mL, exothermic), and heating to 50° C. for 1 h. The cooled mixture was saturated with K$_2$CO$_3$, then partitioned between EtOAc and water. The aqueous phase was reextracted with EtOAc, the combined organic phases were washed with brine, dried (MgSO$_4$), filtered and concentrated. Flash chromatography (silica, 40% EtOAc/hexane) provided alcohol 5-4 as a colorless oil.

TLC R$_f$ 0.26 (silica, 40% EtOAc/hexane)

$^1$H-NMR (400 MHz, CDCl$_3$): δ7.73 (d, J=8 Hz, 1H), 7.56 (t, J=8 Hz, 1H), 7.20 (br s, 1H), 6.80 (d, J=7 Hz, 1H), 3.67 (t, J=7 Hz, 2H), 2.70 (t, J=7 Hz, 2H), 1.77 (qn, J=7 Hz, 2H), 1.61 (m, 2H), 1.51 (s, 9H).

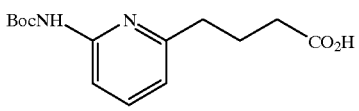

5-5

4-(2-Boc-aminopyridin-6-yl)butanoic acid (5-5)

A solution of alcohol 5-4 (247 mg, 0.93 mmol) in 5 mL acetone was cooled to 0° C. and a solution of Jones Reagent was added dropwise. As the color of the reaction changed from brown to green, additional Jones Reagent was added, until the alcohol was no longer detected by TLC (3.5 h). After quenching with i-PrOH the mixture was diluted with EtOAc, washed with 5% KHSO$_4$ and brine, dried (MgSO$_4$), filtered and concentrated, providing 5-5 as an off-white waxy solid.

$^1$H-NMR (400 MHz, CDCl$_3$): δ9.13 (br s, 1H), 7.90 (d, J=8 Hz, 1H), 7.64 (t, J=8 Hz, 1H), 6.85 (d, J=8 Hz, 1H), 2.80 (t, J=8 Hz, 2H), 2.46 (t, J=7 Hz, 2H), 2.01 (qn, J=7 Hz, 2H), 1.54 (s, 9H).

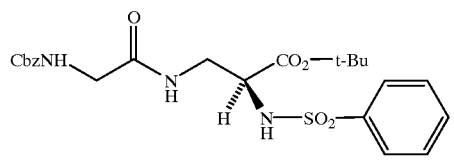

5-6

N—Cbz-glycyl-2(S)-phenylsulfonamido-β-alanine t-butyl ester (5-6)

Amine 1-5 (0.42 g, 1.25 mmol), Cbz—Gly—OH (288 mg, 1.38 mmol), NMM (0.55 mL, 5.0 mmol) and BOP (829 mg, 1.88 mmol) were combined in 6 mL DMF. After stirring overnight the solvent was evaporated, the residue was taken up in EtOAc, the organic solution was washed with water (2×), 5% KHSO$_4$, sat. NaHCO$_3$ and brine, dried (MgSO$_4$), filtered and concentrated. Flash chromatography (silica, 60% EtOAc/hexane) provided 5-6 as a white glass.

TLC R$_f$ 0.27 (silica, 60% EtOAc/hexane)

$^1$H-NMR (400 MHz, CDCl$_3$): δ7.83 (d, J=7 Hz, 2H), 7.58 (t, J=7 Hz, 1H), 7.50 (t, J=8 Hz, 2H), 7.42–7.30 (m, 5H), 6.55 (br s, 1H), 5.59 (d, J=7 Hz, 1H), 5.40 (br s, 1H), 5.16 (s, 2H), 3.95–3.70 (m, 4H), 3.34 (m, 1H), 1.27 (s, 9H).

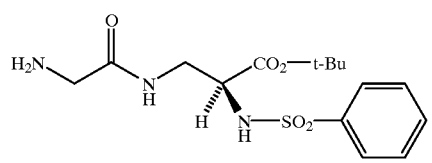

5-7

Glycyl-2(S)-phenylsulfonamido-β-alanine t-butyl ester (5-7)

A solution of 5-6 (0.54 g, 1.10 mmol) in 11 mL EtOAc was treated with 10% Pd/C (108 mg) and stirred under a $H_2$ balloon overnight. After addition of more 10% Pd/C (100 mg) and hydrogenation for 5 d the mixture was filtered through Celite and concentrated, providing 5-6 as a white glass.

$^1$H-NMR (400 MHz, $CD_3OD$): δ7.84 (dm, J=8 Hz, 2H), 7.61 (tm, J=8 Hz, 1H), 7.54 (tm, J=8 Hz, 2H), 4.00 (dd, J=8, 5 Hz, 1H), 3.59 (dd, J=14, 5 Hz, 1H), 3.37 (s, 2H), 1.25 (s, 9H).

5-8

4-(2-Boc-aminopyridin-6-yl)butanoyl-glycyl-2(S)-phenylsulfonamido-β-alanine t-butyl ester (5-8)

Acid 5-5 (144 mg, 0.51 mmol), amine 5-7 (202 mg, 0.56 mmol), NMM (226 μL, 2.1 mmol) and BOP (241 mg, 0.77 mmol) were combined in 2.6 mL DMF. Mter stirring overnight the solvent was evaporated, the residue was dissolved in EtOAc, washed with water, sat. $NaHCO_3$, 5% $KHSO_4$, and brine, dried ($MgSO_4$), filtered and concentrated. Flash chromatography (silica, 10% $CHCl_3$/EtOAc) provided 5-8 as an off-white glass.

TLC $R_f$ 0.22 (silica, 10% $CHCl_3$/EtOAc)

$^1$H-NMR (400 MHz, $d_6$-DMSO): δ9.53 (s, 1H), 8.23 (br d, J=7 Hz, 1H), 7.98 (t, J=6 Hz, 1H), 7.91 (t, J=6 Hz, 1H), 7.76 (d, J=7 Hz, 2H), 7.65–7.53 (m, 5H), 6.87 (d, J=7 Hz, 1H), 3.85 (br s, 1H), 3.60 (t, J=5 Hz, 2H), 3.20–3.10 (m, 2H), 2.60 (t, J=7 Hz, 2H), 2.15 (t, J=7 Hz, 2H), 1.85 (qn, J=7 Hz, 2H), 1.46 (s, 9H), 1.18 (s, 9H).

5-9

4-(2-Aminopyridin-6-yl)butanoyl-glycyl-2(S)-phenylsulfonamido-β-alanine (5-9)

A solution of 5-8 (138 mg, 0.22 mmol) in 1 mL $CH_2Cl_2$ was cooled to 0° C., treated with 1 mL TFA, and warmed to RT for 5 h. After concentration and azeotroping with toluene the residue was purified by flash chromatography (silica, 12:20:1:1, EtOAc/EtOH/$H_2O$/$NH_4OH$), providing 5-9 as a colorless glass.

TLC $R_f$ 0.34 (silica, 12:20:1:1, EtOAc/EtOH/$H_2O$/$NH_4OH$)

$^1$H-NMR (400 MHz, $D_2O$): δ7.76 (dm, J=7 Hz, 2H), 7.55–7.48 (m, 4H), 6.69 (d, J=7 Hz, 1H), 6.57 (d, J=8 Hz, 1H), 3.72–3.62 (m, 2H), 3.55 (dd, J=8, 5 Hz, 1H), 3.37 (dd, J=13, 8 Hz, 1H), 3.13 (dd, J=13, 8 Hz, 1H), 2.63 (t, J=7 Hz, 2H), 2.34 (t, J=7 Hz, 2H), 1.96 (qn, J=7 Hz, 2H).

SCHEME 6

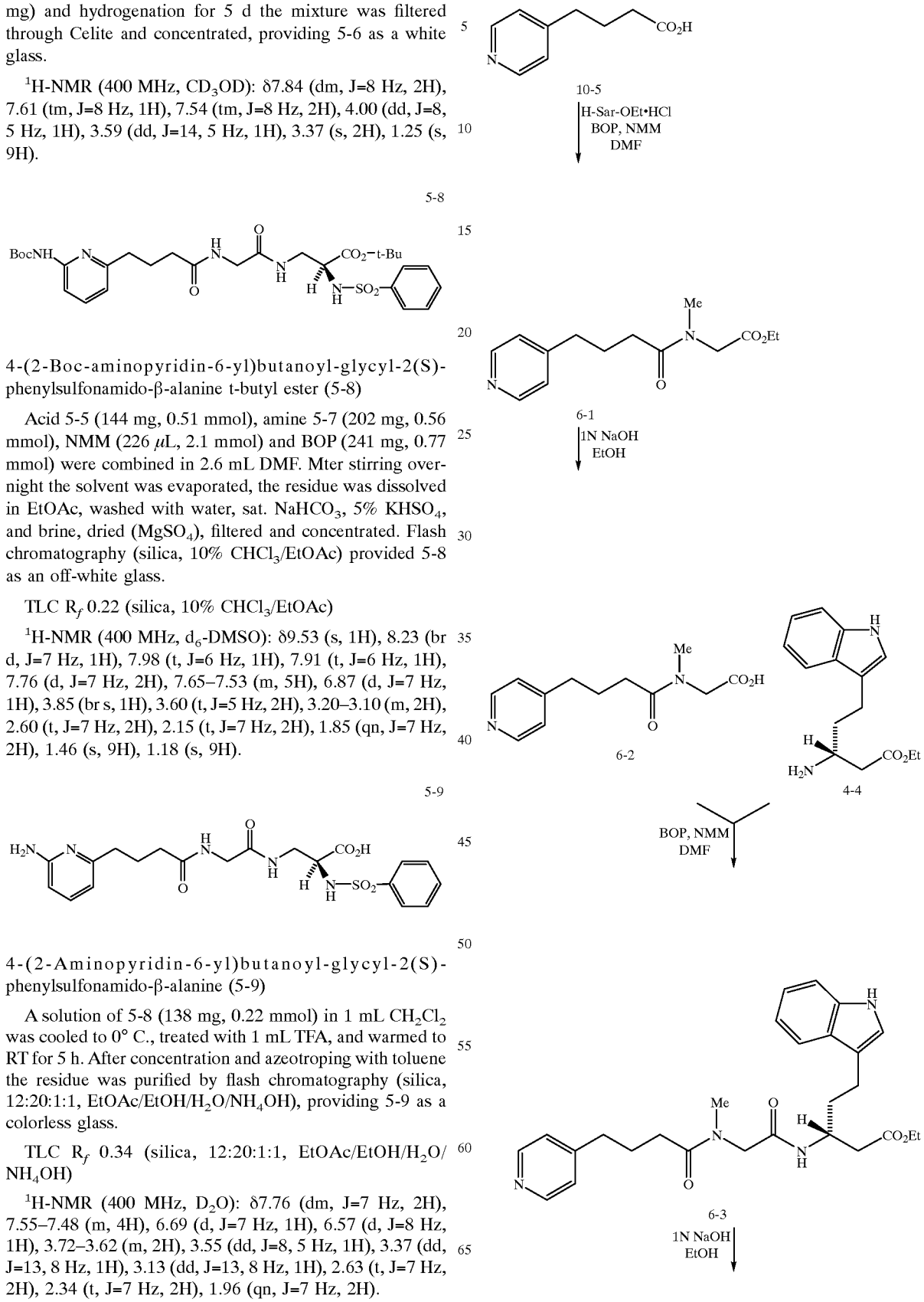

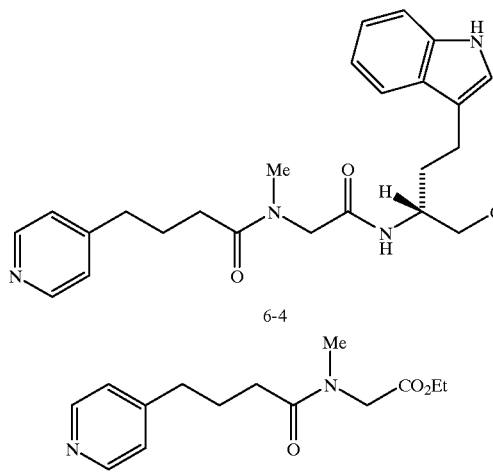

6-4

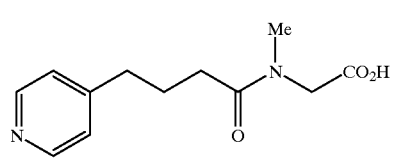

6-1

4-(Pyridin-4-yl)butanoyl-sarcosine ethyl ester (6-1)

4-(4-Pyridyl)butanoic acid 10-5 (100 mg, 1.8 mmol), H—Sar—OEt. HCl (300 mg, 2.0 mmol), BOP (965 mg, 2.2 mmol) and NMM (700 μL, 6.4 mmol) were combined in 9 mL DMF. After stirring overnight the mixture was diluted with EtOAc, washed with water (4×), sat. NaHCO$_3$, and brine, dried (MgSO$_4$), filtered and concentrated. Flash chromatography (silica, 80% to 100% EtOAc/hexane) provided 6-1 as a colorless oil.

TLC R$_f$ 0.44 (silica, 20% MeOH/EtOAc)

$^1$H-NMR (400 MHz, CDCl$_3$): 4:1 mixture of amide rotomers, major rotomer δ8.50 (d, J=5 Hz, 2H), 7.14 (d, J=5 Hz, 2H), 4.20 (q, J=7 Hz, 2H), 4.12 (s, 2H), 3.03 (s, 3H), 2.70 (t, J=8 Hz, 2H), 2.39 (t, J=7 Hz, 2H), 2.02 (qn, J=7 Hz, 2H), 1.23 (t, J=7 Hz, 3H).

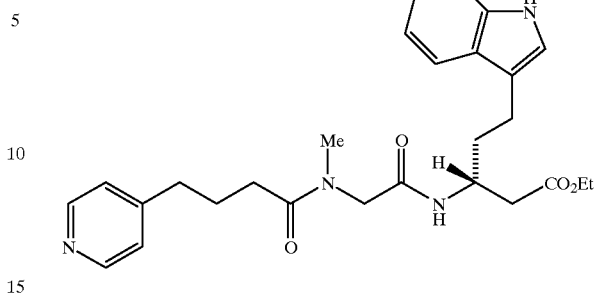

6-2

4-(Pyridin-4-yl)butanoyl-sarcosine (6-2)

Ester 6-1 (324 mg, 1.22 mmol) was dissolved in 6 mL EtOH, then 1 N NaOH (2.4 mL, 2.4 mmol) was added. After stirring overnight the mixture was concentrated, rediluted with EtOAc, extracted into 10% KHSO$_4$, then concentrated, providing acid 6-2, along with inorganic salts.

TLC R$_f$ 0.16 (silica, 4:1:1 CH$_2$Cl$_2$/MeOH/HOAc)

$^1$H-NMR (400 MHz, CD$_3$OD): 1:1 mixture of amide rotomers, δ8.41 (br s, 2H), 7.33 (m, 2H), 4.00/3.90 (s, 2H), 3.05/2.95 (s, 3H), 2.77–2.67 (m, 2H), 2.48/2.37 (t, J=7 Hz, 2H), 2.00–1.90 (m, 2H).

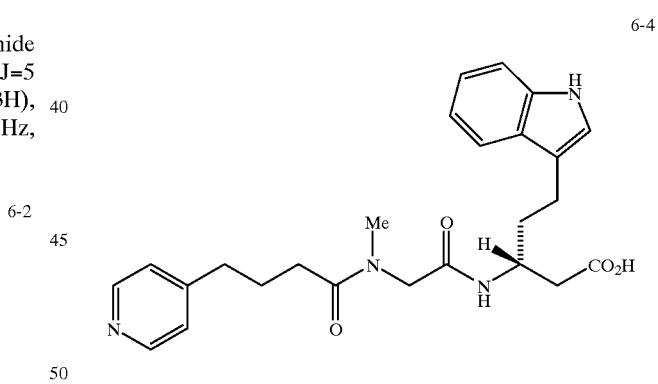

6-3

4-(Pyridin-4-yl)butanoyl-sarcosine-3(R)-[2-(indol-3-yl)ethyl]-β-alanine ethyl ester (6-3)

Acid 6-2 (288 mg, 1.22 mmol), amine 4-4 (318 mg, 1.22 inmol), BOP (647 mg, 1.5 mmol), and NMM (462 μL, 4.2 mmol) were combined in 6 mL DMF. Mter stirring overnight the mixture was diluted with EtOAc, washed with water (4×), sat. NaHCO$_3$, and brine, dried (MgSO$_4$), filtered and concentrated. Flash chromatography (silica, EtOAc then 5% MeOH/EtOAc) provided 6-3 as an orange oil.

TLC R$_f$ 0.4 (20% MeOH/EtOAc)

$^1$H-NMR (400 MHz, CDCl$_3$): 4:1 mixture of amide rotomers, major rotomer δ8.47 (br d, J=5 Hz, 2H), 8.02 (br d, J=6 Hz, 2H), 7.58 (dd, J=16, 8 Hz, 1H), 7.34 (dd, J=8, 4 Hz, 1H), 7.20–7.03 (m, 3H), 7.01 (s, 1H), 6.72 (d, J=9 Hz, 1H), 4.33 (m, 1H), 4.1 (t, J=7 Hz, 3H), 3.98 (s, 2H), 3.05 (s, 3H), 2.90–2.45 (m), 2.39 (t, J=7 Hz, 2H), 2.02–1.70 (m), 1.23 (t, J=7 Hz, 3H).

6-4

4-(Pyridin-4-yl)butanoyl-sarcosine-3(R)-[2-(indol-3-yl)ethyl]-β-alanine (6-4)

Ester 6-3 (400 mg, 0.84 mmol) was dissolved in 4 mL EtOH, then 1 N NaOH (1.7 mL, 1.7 mmol) was added. After 90 min the reaction was neutralized with 1 N HCl (1.7 mL, 1.7 mmol) and concentrated to an oil. Flash chromatography (silica, 50:1:1 EtOH/H$_2$O/NH$_4$OH, then again with 12:10:1:1 EtOAc/EtOH/H$_2$O/NH$_4$OH) provided 6-4.

TLC R$_f$ 0.17 (silica, 12:10:1:1 EtOAc/EtOH/H$_2$O/NH$_4$OH)

$^1$H-NMR (400 MHz, CD$_3$OD): 2:1 mixture of amide rotomers, δ8.38–8.28 (m, 2H), 7.54–7.48 (m, 1H), 7.30–7.25 (m, 2H), 7.21–7.19 (m, 1H), 7.07–6.92 (m, 3H), 4.36–4.27 (m, 1H), 4.03–3.98 (m, 2H), 3.06/2.93 (s, 3H), 2.86–2.60 (m, 4H), 2.52–2.32 (m), 2.05–1.85 (m).

SCHEME 7
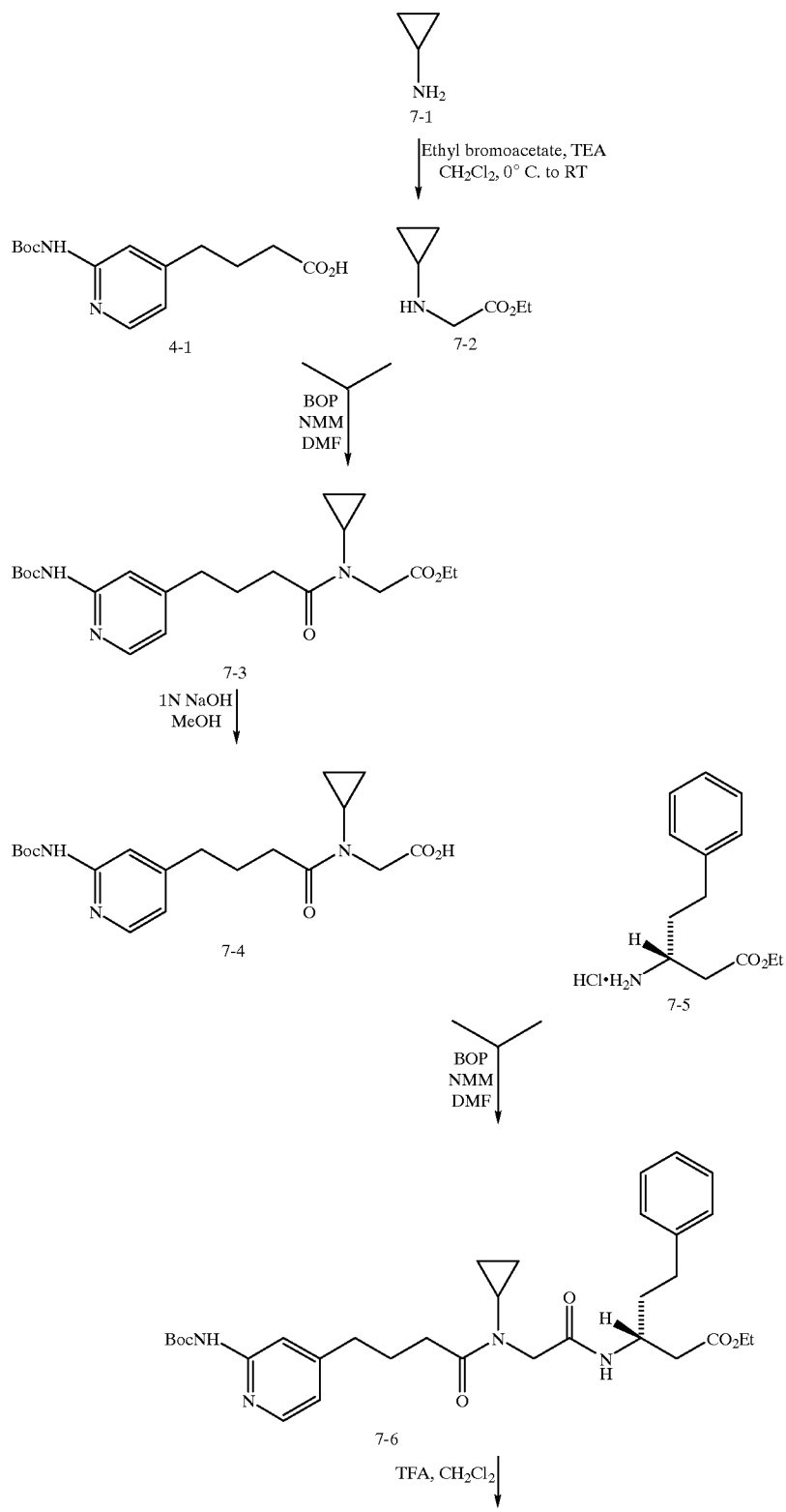

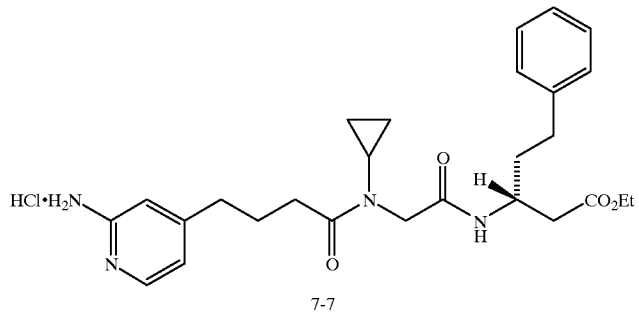

7-7

↓ LiOH, THF

[Structure 7-8]

7-8

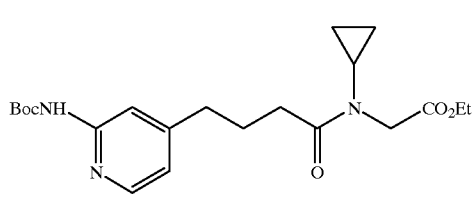

7-2

N-Cyclopropylglycine ethyl ester (7-2)

Cyclopropylamine (12.1 mL, 175 mmol) and TEA (42 mL, 385 mmol) were combined at 0° C. in 350 mL $CH_2Cl_2$, then ethyl bromoacetate (19.4 mL, 175 mmol) was added dropwise. The reaction was warmed to RT for 3 h, then diluted with additional $CH_2Cl_2$, washed with water, sat. $NaHCO_3$, and brine, dried ($Na_2SO_4$), filtered and concentrated. Flash filtration (silica, 30% EtOAc/hexane) provided 7-2 as a light yellow oil.

TLC $R_f$ 0.70 (silica, EtOAc)
$^1$H-NMR (400 MHz, $CDCl_3$): δ4.20 (q, J=7 Hz, 2H), 3.45 (s, 2H), 2.23 (tt, J=6, 3 Hz, 1H), 1.29 (t, J=7 Hz, 3H), 0.43 (m, 2H), 0.36 (m, 2H).

[Structure 7-3]

7-3

4-(2-Boc-amino-pyridin-4-yl)butanoyl-N-cyclopropylglycine ethyl ester (7-3)

Acid 4-1 (0.86 g, 3.1 mmol), amine 7-2 (0.48 g, 3.4 mmol), NMM (1.35 mL, 12.3 mmol) and BOP (2.04 g, 4.61 mmol) were combined in 15 mL DMF. After stirring overnight the mixture was concentrated, redissolved in EtOAc, washed with water, 5% $KHSO_4$, sat. $NaHCO_3$ and brine, dried over $MgSO_4$, filtered and concentrated. Flash chromatography (silica, 50% EtOAc/hexane) provided 7-3 as a colorless oil.

TLC $R_f$ 0.29 (silica, 50% EtOAc/hexane)
$^1$H-NMR (400 MHz, $CDCl_3$): δ8.14 (d, J=5 Hz, 1H), 7.81 (s, 1H), 7.77 (br s, 1H), 6.84 (dd, J=5, 1 Hz, 1H), 4.18 (q, J=7 Hz, 2H), 4.08 (s, 2H), 2.80 (tt, J=7, 4 Hz, 1H), 2.69 (t, J=7 Hz, 2H), 2.60 (t, J=7 Hz, 2H), 2.02 (qn, J=7 Hz, 2H), 1.53 (s, 9H), 1.27 (t, J=7 Hz, 3H), 0.83 (m, 2H), 0.72 (m, 2H).

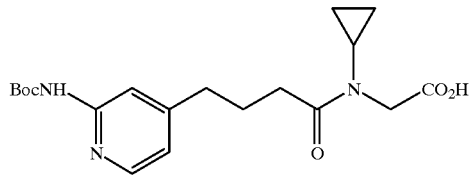

7-4

4-(2-Boc-amino-pyridin-4-yl)butanoyl-N-cyclopropyglycine (7-4)

Ester 7-3 (1.07 g, 2.64 mmol) was dissolved in 26 mL MeOH, then treated with 1 N NaOH (6.6 mL, 6.6 mmol). After stirring overnight the reaction was concentrated, redissolved in water, the pH was adjusted to 1 with 10% $KHSO_4$, then extracted with EtOAc (5×). The aqueous phase was adjusted to pH 3 with aq. NaOH, then reextracted with EtOAc (2×). The combined organic phases were washed with brine, dried ($MgSO_4$), filtered and concentrated, providing 7-4 as a white foam.

TLC $R_f$ 0.24 (silica, 19:1:1, $CH_2Cl_2$/MeOH/HOAc)
$^1$H-NMR (300 MHz, $CDCl_3$): δ9.15 (br s, 1H), 7.97 (d, J=5 Hz, 1H), 7.94 (s, 1H), 6.89 (dd, J=5, 1 Hz, 1H), 4.14 (s, 2H), 2.81 (tt, J=7, 3 Hz, 1H), 2.73 (t, J=7 Hz, 2H), 2.61 (t, J=7 Hz, 2H), 2.04 (qn, J=7 Hz, 2H), 1.51 (s, 9H), 0.85 (m, 2H), 0.76 (m, 2H).

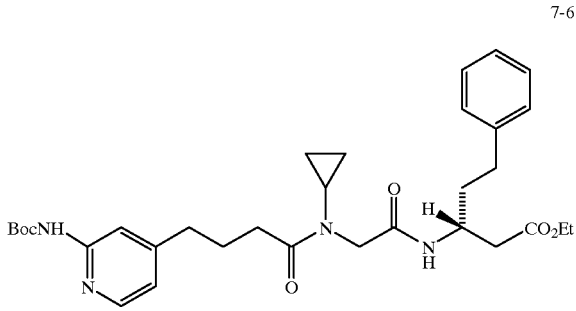

4-(2-Boc-amino-pyridin-4-yl)butanoyl-N-cyclopropylglycyl-3(R)-(2-phenethyl)-β-alanine ethyl ester (7-6)

Acid 7-4 (415 mg, 1.1 mmol), amine hydrochloride 7-5 (see procedure in EP 478 362 utilizing Boc—Gly(OEt) as starting material) (284 mg, 1.1 mmol), NMM (0.48 mL, 4.4 mmol) and BOP (729 mg, 1.65 mmol) were combined in 5 mL DMF. After stirring overnight the reaction was concentrated, redissolved in EtOAc, washed with water, 5% $KHSO_4$, sat. $NaHCO_3$, and brine, dried ($MgSO_4$), filtered and concentrated. Flash chromatography (silica, EtOAc) provided 7-6 as a colorless waxy solid.

TLC $R_f$ 0.39 (silica, EtOAc)

$^1$H-NMR (400 MHz, $d_6$-DMSO): δ9.66 (s, 1H), 8.11 (d, J=5 Hz, 1H), 7.76 (d, J=9 Hz, 1H), 7.68 (s, 1H), 7.25 (t, J=7 Hz, 2H), 7.20–7.12 (m, 3H), 6.88 (dd, J=5, 1 Hz, 1H), 4.01 (q, J=7 Hz, 2H), 3.91 (AB d, J=16 Hz, 1H), 3.83 (AB d, J=16 Hz, 1H), 3.32 (s, 2H), 2.78 (m, 1H), 2.65–2.40 (m), 1.86–1.77 (m), 1.46 (s, 9H), 1.14 (t, J=7 Hz, 3H), 0.77–0.70 (m, 4H).

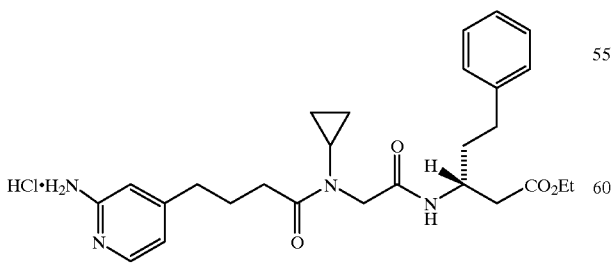

4-(2-Amino-pyridin-4-yl)butanoyl-N-cyclopropylglycyl-3(R)-(2-phenethyl)-β-alanine ethyl ester hydrochloride (7-7)

A solution of 7-6 (530 mg, 0.91 mmol) in 4.6 mL $CH_2Cl_2$ was cooled to 0° C., 4.6 mL TFA was added, and after 1 h the reaction was warmed to RT for 90 min. After concentration and azeotroping with toluene the residue was purified by flash chromatography (silica, 10:1, EtOAc:$NH_3$-saturated EtOH). The residue was dissolved in EtOAc, treated with 1 N HCl in ether, concentrated, then lyophilized from aq. acetonitrile, providing 7-7 as a glassy solid.

TLC $R_f$ 0.25 (10:1, EtOAc:$NH_3$-saturated EtOH)

$^1$H-NMR (400 MHz, $d_6$-DMSO): δ7.94 (br s, 1H), 7.86–7.82 (m, 2H), 7.25 (t, J=7 Hz, 2H), 7.20–7.13 (m, 3H), 6.80–6.75 (m, 2H), 4.05 (m), 4.02 (q, J=7 Hz, 2H), 3.93 (AB d, J=16 Hz, 1H), 3.85 (AB d, J=16 Hz, 1H), 2.78 (qn, 1H), 2.65 (t, J=7 Hz, 2H), 2.59 (t, J=7 Hz, 2H), 2.55–2.40 (m), 1.82 (qn, J=7 Hz, 2H), 1.80–1.70 (m, 2H), 1.15 (t, J=7 Hz, 3H), 0.80–0.70 (m, 4H).

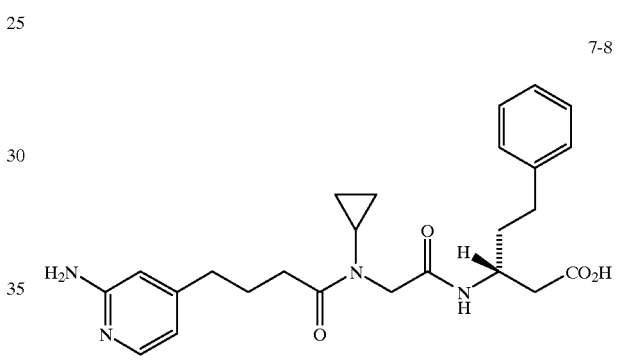

4-(2-Amino-pyridin-6-yl)butanoyl-N-cyclopropylglycyl-3(R)-(2-phenethyl)-β-alanine (7-8)

Ester 7-7 (100 mg, 0.18 mmol) was dissolved in 4 mL THF, then treated with 1 N LiOH (0.9 mL, 0.9 mmol). After stirring overnight the mixture was concentrated and purified by flash chromatography (silica, 15:20:1:1 EtOAc/EtOH/ $H_2O$/$NH_4OH$) to provide 7-8 as a white solid.

TLC $R_f$ 0.36 (silica, 15:20:1:1 EtOAc/EtOH/$H_2O$/$NH_4OH$)

$^1$H-NMR (400 MHz, $d_6$-DMSO): δ7.81 (d, J=9 Hz, 1H), 7.77 (d, J=5 Hz, 1H), 7.27 (t, J=7 Hz, 2H), 7.20–7.12 (m, 3H), 6.34 (dd, J=5, 1 Hz, 1H), 6.28 (s, 1H), 5.76 (br s, 2H), 4.03 (m, 1H), 3.91 (AB d, J=16 Hz, 1H), 3.85 (AB d, J=16 Hz, 1H), 2.76 (m, 1H), 2.65–2.50 (m), 2.45 (t, J=7 Hz, 2H), 2.37 (d, J=7 Hz, 2H), 1.82–1.60 (m), 0.77–0.68 (m, 4H).

SCHEME 8
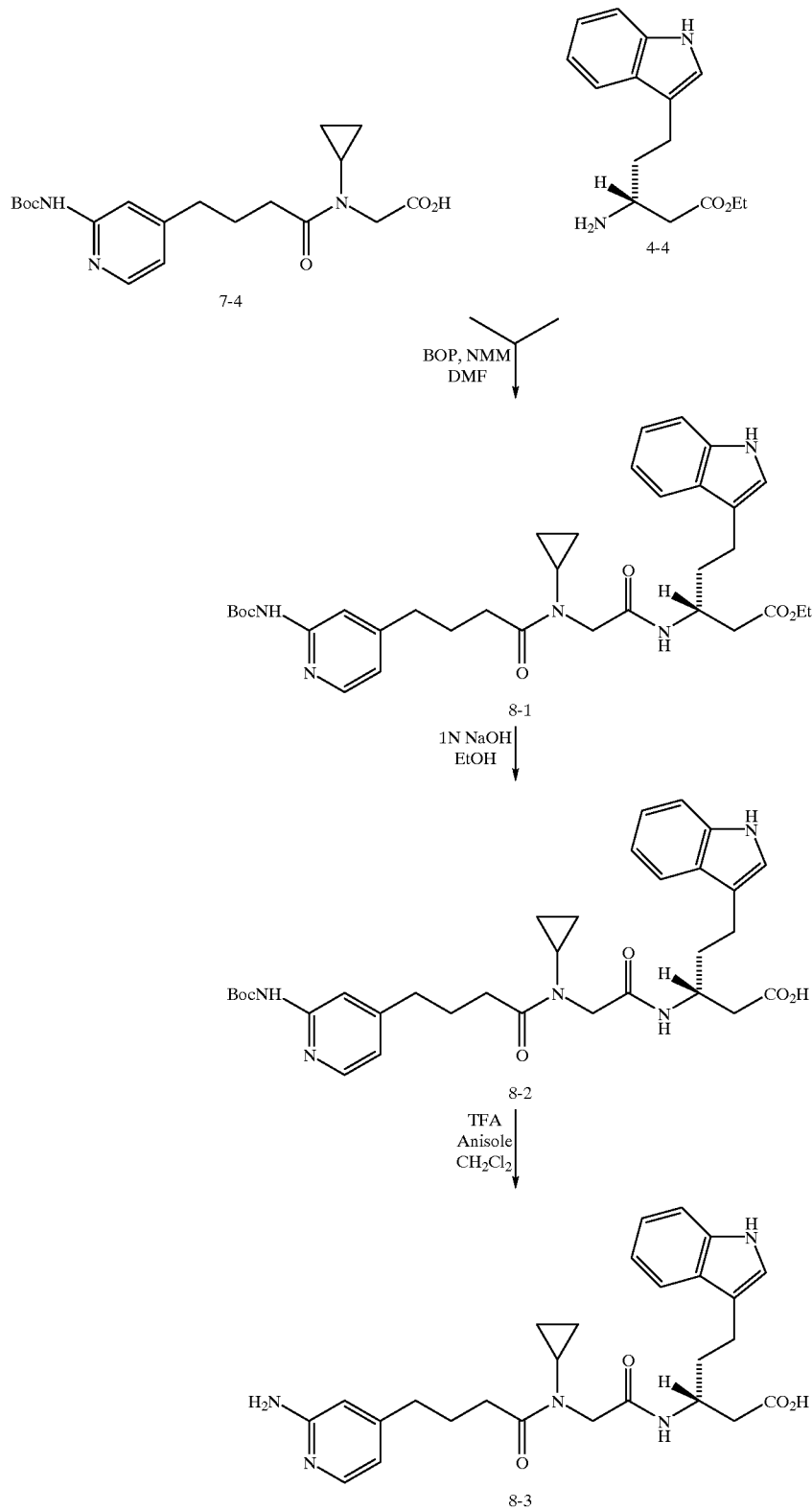

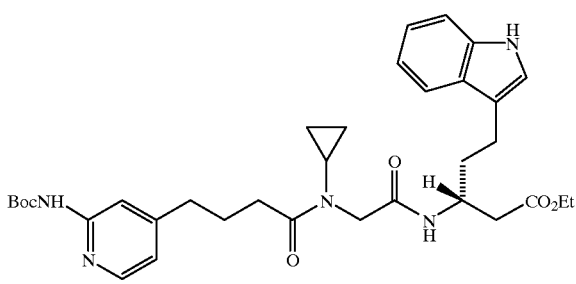

8-1

4-(2-Boc-amino-pyridin-4-yl)butanoyl-N-cyclopropylglycyl-3(R)-[2-(indol-3-yl)ethyl]-β-alanine ethyl ester (8-1)

Acid 7-4 (180 mg, 0.48 mmol), amine 4-4 (130 mg, 0.50 mmol), NMM (183 μL, 1.7 mmol) and BOP (253 mg, 0.57 mmol) were combined in 5 mL DMF. After stirring overnight the reaction was concentrated, redissolved in EtOAc, washed with water (3×), 10% KHSO$_4$, sat. NaHCO$_3$, and brine, dried (MgSO$_4$), filtered and concentrated. Flash chromatography (silica, 80% EtOAc/hexane) provided 8-1 as a glassy solid.

TLC R$_f$ 0.34 (silica, EtOAc)

$^1$H-NMR (400 MHz, CDCl$_3$): δ8.10–8.00 (m, 2H), 7.79 (s, 1H), 7.56 (d, J=8 Hz, 1H), 7.35–7.30 (m, 2H), 7.16 (t, J=8 Hz, 1H), 7.08 (t, J=8 Hz, 1H), 7.04 (s, 1H), 6.80 (d, J=5 Hz, 1H), 6.71 (d, J=9 Hz, 1H), 4.29 (m, 1H), 4.09 (q, J=7 Hz, 2H), 3.99 (s, 2H), 2.85–2.70 (m, 4H), 2.66 (t, J=7 Hz, 2H), 2.61 (t, J=7 Hz, 2H), 2.51 (m), 2.05–1.87 (m, 4H), 1.53 (s, 9H), 1.21 (t, J=7 Hz, 3H), 0.90–0.75 (m, 4H).

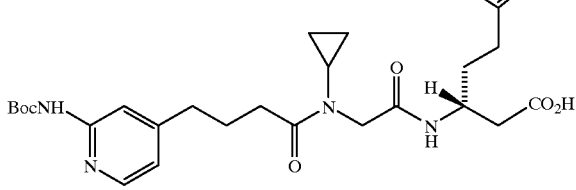

8-2

4-(2-Boc-amino-pyridin-4-yl)butanoyl-N-cyclopropylglycyl-3(R)-[2-(indol-3-yl)ethyl]-β-alanine (8-2)

Ester 8-1 (223 mg, 0.36 mmol) was dissolved in 4 mL EtOH, then 1 N NaOH (0.90 mL, 0.90 mmol) was added. After a few hours the reaction was diluted with EtOAc, extracted with water and the pH of the aq. phase was adjusted to 1 with 10% KHSO$_4$. The aqueous layer was extracted with EtOAc (2×), the combined organic layers were washed with brine, dried (MgSO$_4$), filtered and concentrated, providing 8-2 as an oil.

TLC R$_f$ 0.64 (silica, 9:1:1 CH$_2$Cl$_2$/MeOH/HOAc)

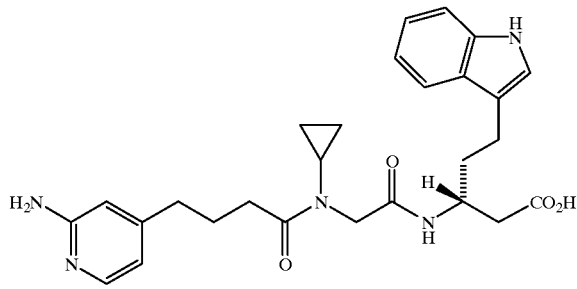

8-3

4-(2-Amino-pyridin-4-yl)butanoyl-N-cyclopropylglycyl-3(R)-[2-(indol-3-yl)ethyl]-β-alanine (8-3)

Acid 8-2 (144 mg, 0.24 mmol) was dissolved in 3 mL CH$_2$Cl$_2$, then anisole (120 μL, 0.96 mmol) and TFA (3 mL) were added. After ca 1 h the reaction was concentrated. Flash chromatography (silica, 18:10:1:1 EtOAc/EtOH/H$_2$O/NH$_4$OH, twice) provided 8-3 as a white solid.

TLC R$_f$ 0.29 (silica, 18:10:1:1 EtOAc/EtOH/H$_2$O/NH$_4$OH)

$^1$H-NMR (400 MHz, D$_2$O): δ7.88 (m, 1H), 7.70 (m, 1H), 7.53 (m, 1H), 7.30–7.10 (m, 3H), 6.69 (m, 1H), 6.58 (m, 1H), 4.23 (m, 1H), 3.99 (m, 2H), 2.84 (m, 3H), 2.70 (m, 2H), 2.62 (m, 2H), 2.44 (m), 2.10–1.82 (m), 0.88–0.72 (m, 4H).

SCHEME 9

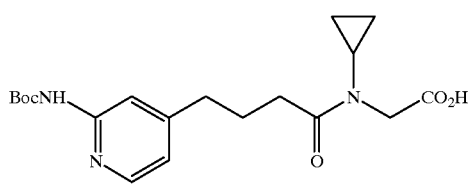

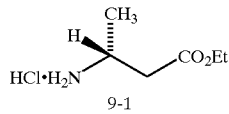

9-1

BOP, NMM
DMF

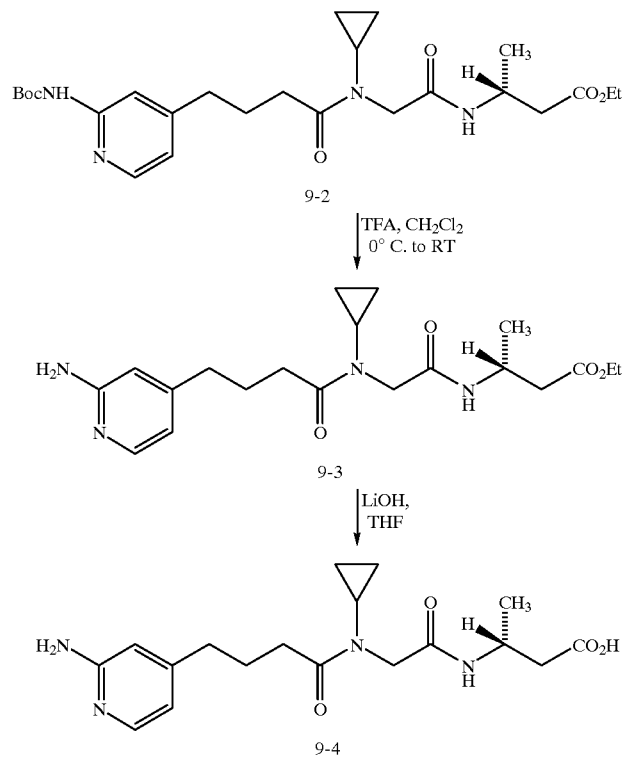

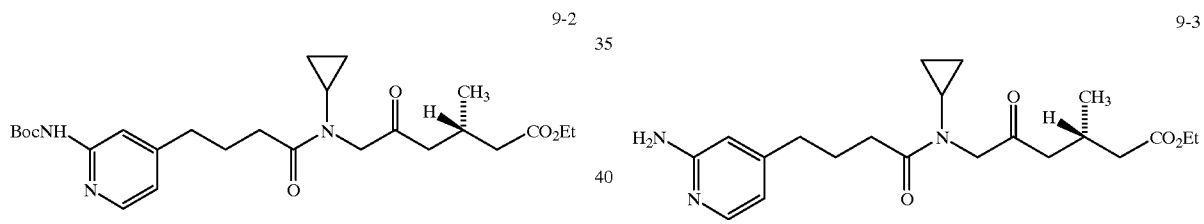

4-(2-Boc-amino-pyridin-4-yl)butanoyl-N-cyclopropylglycyl-3(R)-methyl-β-alanine ethyl ester (9-2)

Acid 7-4 (100 mg, 0.26 mmol), amine hydrochloride 9-1 (see U.S. Pat. No. 5,281,585) (49 mg, 0.29 mmol), NMM (117 μL, 1.1 mmol) and BOP (176 mg, 0.40 mmol) were combined in 1.3 mL DMF. After 3 d the mixture was concentrated, redissolved in EtOAc, washed with water (2×), 5% KHSO$_4$, sat. NaHCO$_3$, and brine, dried (MgSO$_4$), filtered and concentrated. Flash chromatography (silica, EtOAc) provided 9-2 as a colorless oil.

TLC R$_f$ 0.27 (silica, EtOAc)

$^1$H-NMR (400 MHz, CDCl$_3$): δ8.10 (d, J=5 Hz, 1H), 8.00 (br s, 1H), 7.85 (s, 1H), 6.90 (dd, J=5, 1 Hz, 1H), 6.63 (d, J=8 Hz, 1H), 4.30 (m, 1H), 4.12 (q, J=7 Hz, 2H), 4.02 (AB d, J=15 Hz, 1H), 3.93 (AB d, J=15 Hz, 1H), 2.77 (m, 1H), 2.73 (t, J=7 Hz, 2H), 2.62 (t, J=7 Hz, 2H), 2.47 (m, 2H), 2.04 (m, 2H), 1.53 (s, 9H), 1.25 (t, J=7 Hz, 3H), 1.20 (d, J=7 Hz, 3H), 0.88–0.78 (m, 4H).

4-(2-Amino-pyridin-4-yl)butanoyl-N-cyclopropylglycyl-3(R)-methyl-β-alanine ethyl ester (9-3)

A solution of 9-2 (84 mg, 0.17 mmol) in 1 mL CH$_2$Cl$_2$ at 0° C. was treated with 1 nmL TFA. After 3 h the mixture was warmed to RT for 1 h, then concentrated and azeotroped with toluene. Flash chromatography (silica, 15% NH$_3$ satd. i-PrOH/EtOAc) and lyophilization from aq. acetonitrile provided 9-3 as a semi-solid.

TLC R$_f$ 0.19 (silica, 15% NH$_3$ satd. i-PrOH/EtOAc)

$^1$H-NMR (400 MHz, d$_6$-DMSO): δ7.78 (d, J=5 Hz, 1H), 7.76 (d, J=8 Hz, 1H), 6.37 (dd, J=5, 1 Hz, 1H), 6.30 (s, 1H), 5.90 (br s, 1H), 4.09 (m, 1H), 4.04 (q, J=7 Hz, 2H), 3.86 (AB d, J=16 Hz, 1H), 3.79 (AB d, J=16 Hz, 1H), 2.73 (m, 1H), 2.45 (t, J=7 Hz, 2H), 2.35 (ABX dd, J=15, 7 Hz, 1H), 1.77 (qn, J=7 Hz, 2H), 1.17 (t, J=7 Hz, 3H), 1.07 (d, J=7 Hz, 3H), 0.76–0.67 (m, 4H).

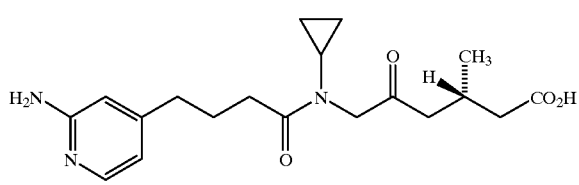

4-(2-Amino-pyridin-4-yl)butanoyl-N-cyclopropylglycyl-3 (R)-methyl-β-alanine (9-4)

Ester 9-3 (44 mg, 0.11 mmol) was dissolved in 1.1 mL THF, then 1 N LiOH (0.28 mL, 0.28 mmol) was added. After stirring overnight the reaction mixture was loaded directly onto a flash chromatography column (silica, eluting with 7:20:1:1 EtOAc/EtOH/$H_2O$/$NH_4OH$) providing 9-4 as a white solid.

TLC $R_f$ 0.62 (silica, 7:20:1:1 EtOAc/EtOH/$H_2O$/$NH_4OH$)

$^1$H-NMR (300 MHz, $D_2O$): δ7.72 (d, J=7 Hz, 1H), 6.90–6.80 (m, 2H), 4.16 (hex, J=7 Hz, 1H), 4.04 (s, 2H), 2.86 (tt, J=7, 4 Hz, 1H), 2.80–2.65 (m, 4H), 2.41 (ABX dd, J=14, 6 Hz, 1H), 2.31 (ABX dd, J=14, 7 Hz, 1H), 1.98 (qn, J=7 Hz, 2H), 1.16 (d, J=7 Hz, 3H), 0.89 (m, 2H), 0.80 (m, 2H).

SCHEME 10

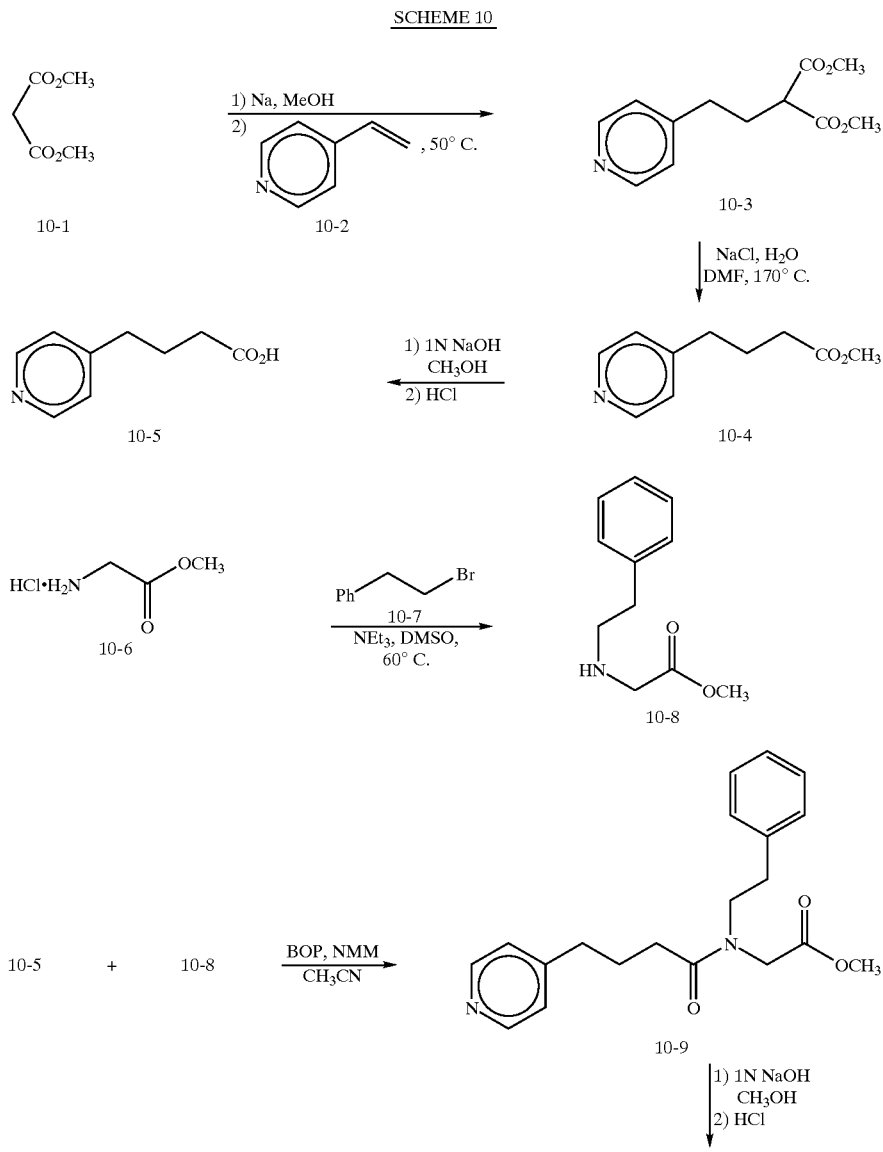

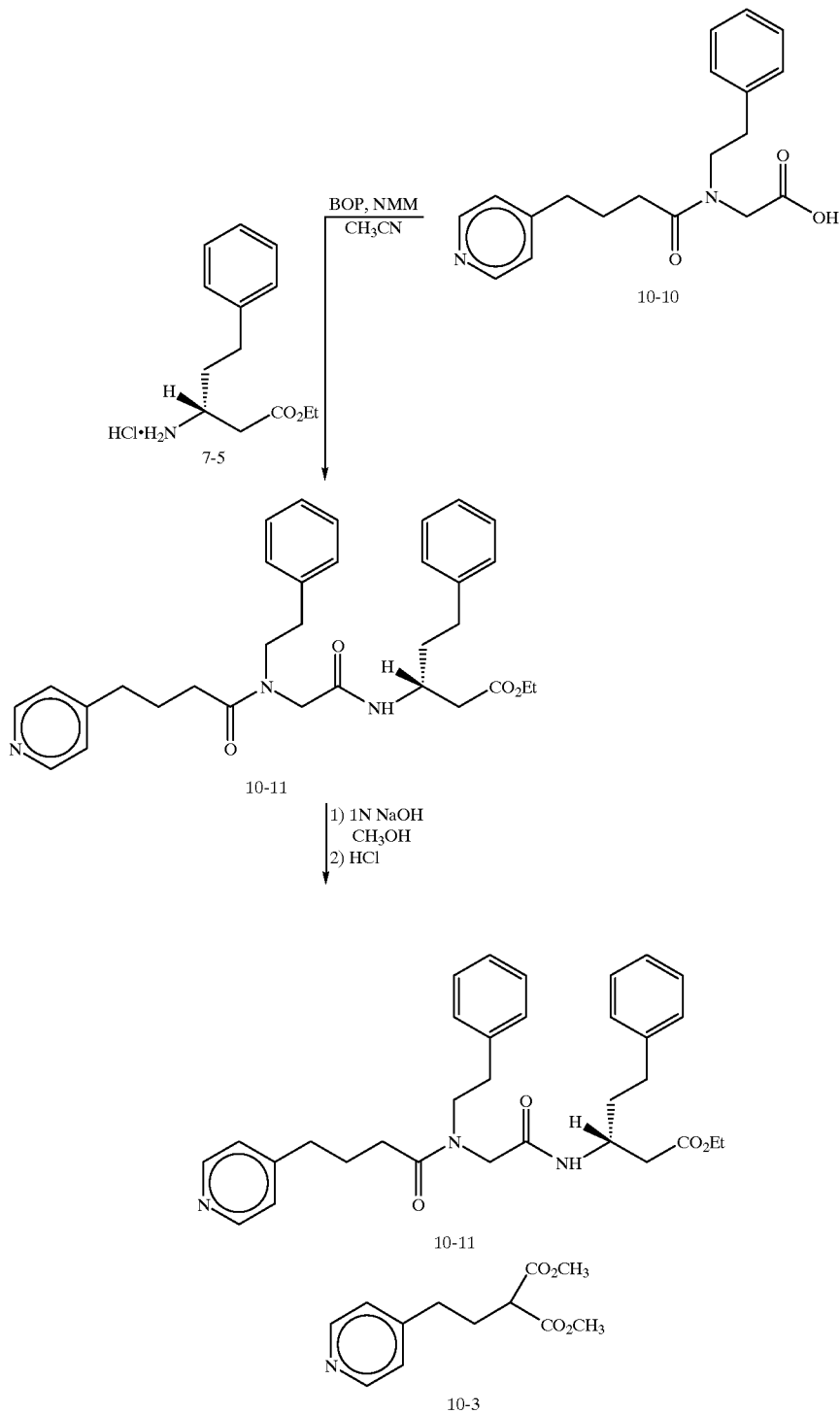

Methyl 2-(methoxycarbonyl)-4-(pyridin-4-yl)butyrate (10-3)

To a stirred solution of elemental sodium (20 g, 840 mmol) and CH$_3$OH (600 ml) was added dimethyl malonate 10-1 (135 ml, 1120 mmol). After 5 minutes, 4-vinyl pyridine 10-2 (15.3 ml, 140 mmoles) was added and the solution was heated to 50° C. for 18 h. The reaction was diluted with EtOAc and then washed with sat NaHCO$_3$, brine, dried (MgSO$_4$) and concentrated. Flash chromatoraphy (silica, 60% EtOAc/hexanes) furnished the diether 10-3 (19.1 g) as a yellow oil.

TLC R$_f$=0.43 (silica, EtOAc)

$^1$H NMR (400 MHz, CDCl$_3$) δ8.52 (d, J=6 Hz, 2H), 7.12 (d, J=6 Hz, 2H), 3.75 (s, 6H), 3.38 (t, J=8 Hz, 1H), 2.64 (t, J=8 Hz, 2H), 2.24 (m, 2H).

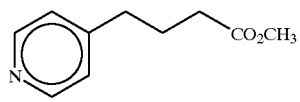

10-4

Methyl 4-(Pyridin-4-yl)butyrate (10-4)

A solution of diester 10-3 (19.0 g, 80.1 mmol), H₂O (1.45 ml, 80.1 mmol), NaCl (10.5 g, 160.2 mmol) and DMF was heated to 170° C. for 18 h. The reaction was diluted with EtOAc and then washed with sat. NaHCO₃, brine, dried (MgSO₄) and concentrated. Flash chromatography (silica, 60% EtOAc/hexanes) afforded ester 10-4 as a brown oil.

TLC $R_f$ 0.32 (silica, EtOAc)

$^1$H NMR (400 MHz, CD₃OD) 5 8.40 (d, J=6 Hz, 2H), 7.28 (d, J=6 Hz, 2H), 3.64 (s, 3H), 2.67 (t, J=8 Hz, 2H), 2.36 (t, J=8 Hz, 2H), 1.94 (m, 2H).

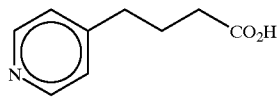

10-5

4-(Pyridin-4-yl)butanoic acid (10-5)

A solution of ester 10-4 (10.0 g, 56 mmol), 1N NaOH (84 ml, 84 mmole) and CH₃OH (200 ml) was stirred at ambient temperature for 1.0 h. Concentrated HCl (7.0 ml, 84 mmol) was added followed by concentration. The residue was dissolved in CHCl₃, dried (MgSO₄) and concentrated to give acid 10-5 as a yellow solid.

TLC $R_f$ 0.41 (silica 10:1:1 CH₂Cl₂/MeOH/AcOH)

$^1$H NMR (400 MHz, CD₃OD) δ8.40 (d, J=6 Hz, 2H), 7.30 (d, J=6 Hz, 2H), 2.71 (t, J=8 Hz, 2H), 2.32 (t, J=7 Hz, 2H), 1.93 (m, 2H).

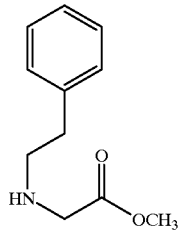

10-8

N-(2-Phenethyl)glycine methyl ester (10-8)

A solution of amine methyl ester 10-6 (1.0 g, 7.96 mmol), bromide 10-7 (1.09 ml, 7.96 mmole), NEt₃ (3.33 ml, 23.9 mmol) and DMSO (25 ml) was heated to 60° C. for 16 h. The reaction mixture was diluted with EtOAc and then washed with sat. NaHCO₃, brine, dried (MgSO₄) and concentrated. Flash chromatography (silica, 80% EtOAc/hexanes) furnished ester 10-8 as a yellow oil.

TLC $R_f$ 0.29 (silica, EtOAc)

$^1$H NMR (400 MHz, CDCl₃) δ7.29 (m, 2H), 7.22 (m, 3H), 3.71 (s, 3H), 3.43 (s, 2H), 2.89 (m, 2H), 2.82 (m, 2H).

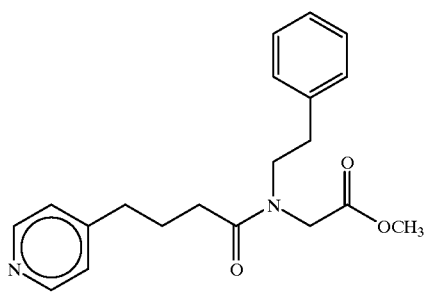

10-9

4-(Pyridin-4-yl)butanoyl-N-(2-phenethyl)glycine methl ester (10-9)

To a stirred solution of acid 10-5 (342 mg, 2.07 mmol), NMM (910 μl, 8.28 mmol) and CH₃CN (15 ml) was added BOP reagent (1.01 g, 2.28 mmol). After 30 minutes, amine 10-8 (400 mg, 2.07 mmol) was added and stirring continued for an additional 18 h. The reaction was diluted with EtOAc and then washed with sat. NaHCO₃, brine, dried (MgSO₄) and concentrated. Flash chromatography (silica, EtOAc) furnished ester 10-9 as a yellow oil.

TLC $R_f$=0.23 (silica, EtOAc)

$^1$H NMR (CD₃OD) 8.39 (d, J=8 Hz, 2H), 7.14–7.29 (m, 7H), 4.84 (s, 2H), 3.70 (s, 3H), 3.58 (t, J=7 Hz, 2H), 2.82 (t, J=7 Hz, 2H), 2.66 (t, J=8 Hz, 0.56 H), 2.55 (t, J=8 Hz, 1.44 H), 2.28 (t, J=7 Hz, 0.56 H), 2.10 (t, J=7 Hz, 1.44 H).

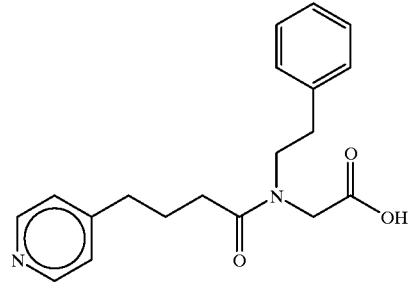

10-10

4-(Pyridin-4-yl)butanoyl-N-(2-phenethyl)gylcyl (10-10)

A solution of ester 10-9 (500 mg, 1.47 mnmole), 1N NaOH (2 ml, 2 mmol) and CH₃OH (5 ml) was stirred at ambient temperature for 2.0 h. Concentrated HCl (167 μl, 2.0 mmol) was added followed by concentration. The residue was dissolved in CHCl₃, dried (MgSO₄) and concentrated to give acid 10-10 as a white solid.

$^1$H NMR (400 MHz, CD₃OD) δ8.47 (d, J=5 Hz, 2H), 7.44 (m, 2H), 7.25 (m, 5H), 4.02 (s, 1.44H), 3.96 (s, 0.56H), 3.58 (m, 2H), 2.84 (m, 2H), 2.74 (t, J=8 Hz, 0.56H), 2.63 (t, J=8 Hz, 1.44H), 2.33 (t, J=7 Hz, 0.56H), 2.14 (t, J=7 Hz, 1.44H), 1.94 (m, 0.56H), 1.79 (m, 1.44H).

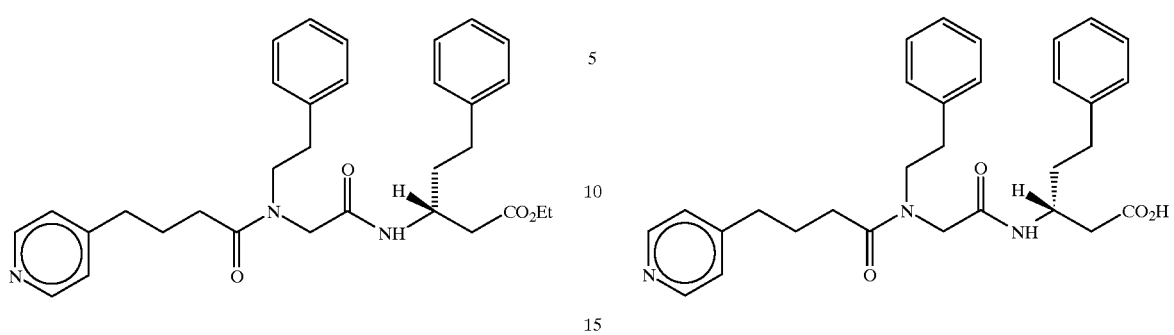

10-11

10-12

4-(Pyridin-4-yl)butanoyl-N-(2-phenylethyl)glycyl-3(R)-(2-phenethyl)-β-alanine ethyl ester (10-11)

A solution of acid 10-10 (160 mg, 0.4903 mmol) amine 7-5 (164 mg, 0.49 immol), NMM (216 μl, 1.96 mmol), BOP reagent (239 mg, 0.539 mmol) and CH$_3$CN (5 ml) was stirred at ambient temperature for 18 h. The reaction was diluted with EtOAc and then washed with sat. NaHCO$_3$, brine, dried (MgSO$_4$) and concentrated. Flash chromatography (silica, EtOAc) furnished ester 10-11 (220 mg) as a colorless oil.

TLC R$_f$=0.21 (silica, EtOAc)

$^1$H NMR (400 MHz, CD$_3$OD) δ8.37 (m, 2H), 7.24 (m, 12H), 4.23 (m, 1H), 4.06 (m, 2H), 3.95 (m, 2H), 2.84 (m, 2H), 2.56 (m, 6H), 2.34 (t, J=7 Hz, 0.56H), 2.16 (t, J=7 Hz, 1.44H), 1.83 (m, 0.56H), 1.81 (m, 1.44H), 1.91 (m, 3H).

4-(Pyridin-4-yl)butanoyl-N-(2-phenyl)glycyl-3(R)-(2-phenethyl)-β-alanine (10-12)

A solution of ester 10-11 (200 mg, 0.3778 mmole), 1N NaOH (0.5 ml, 0.5 mmol) and CH$_3$OH was stirred at ambient temperature for 1.5 h followed by concentration. The crude acid was dissolved in H$_2$O, acidified with conc. HCl, concentrated and then azeotroped with toluene. Flash chromatography (silica, 20:20:1:1 EtOAc/EtOH/NH$_4$OH/H$_2$O) furnished acid 10-12 (100 mg) as a white solid.

TLC R$_f$ 0.18 (20:20:1:1 EtOAc/EtOH/NH$_4$OHIH$_2$O)

$^1$H NMR (400 MHz, D$_2$O) δ8.47 (d, J=6 Hz, 1.36H), 8.43 (d, J=6 Hz, 0.64H), 7.71 (d, J=6 Hz, 0.64H), 7.66 (d, J=6 Hz, 1.36H), 7.20 (m, 10H), 4.07 (m, 1H), 3.81 (s, 1.36H), 3.73 (d, J=6 Hz, 0.64H), 3.51 (bt, 1.36H), 3.43 (m, 0.64H), 2.73 (m, 3H), 2.60 (t, J=7 Hz, 1.36H), 2.53 (m, 3.64H), 2.18 (t, J=7 Hz, 0.64H), 1.78 (m, 5.36H).

SCHEME 11

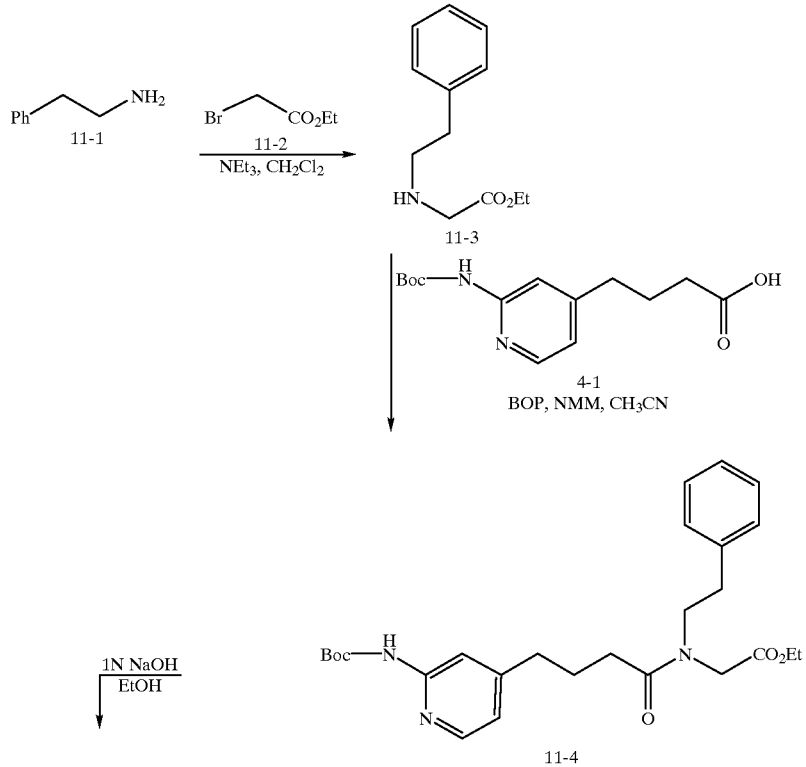

-continued
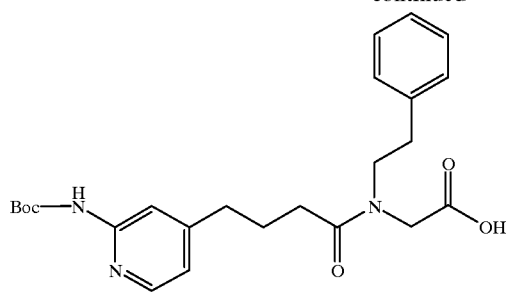
11-5
↓ 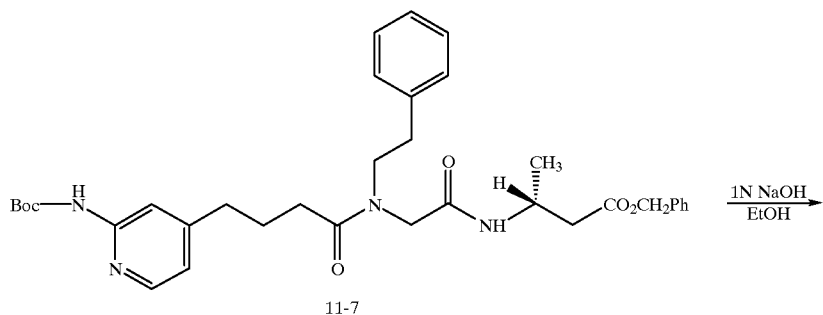
11-7
↓ 1N NaOH / EtOH
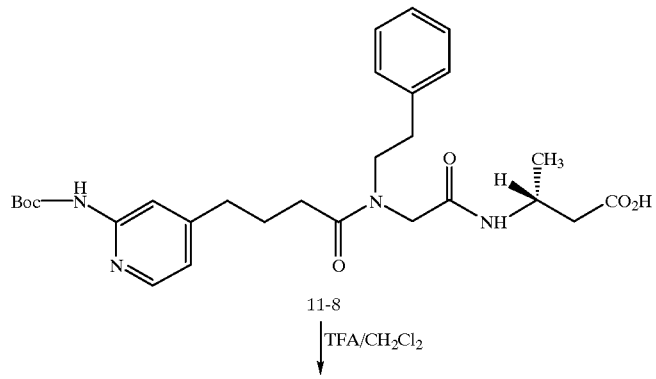
11-8
↓ TFA/CH₂Cl₂
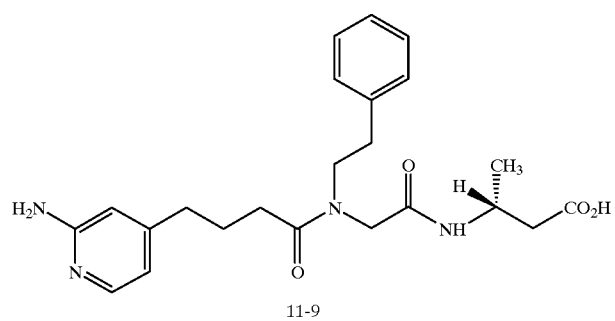
11-9

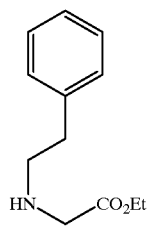

11-3

N-(2-Phenethyl)glycine ethyl ester (11-3)

A solution of amine 11-1 (20.0 g, 165 mmol), NEt₃ (47 ml, 330 mmol) in CH₂Cl₂ at 0° C. was treated with bromide 11-2 (22.4 ml, 182 mmol) followed by the removal of the cooling bath. After 1.0 h, the solution was washed with sat. NaHCO₃, brine, dried (MgSO₄) and concentrated. Flash chromatography (silica, 50% EtOAc/hexanes) afforded ester 11-3 as a yellow oil.

TLC $R_f$ 0.25 (silica, 50% EtOAc/hexanes)

$^1$H NMR (400 MHz, CD₃OD) 7.25 (m, 5H), 4.15 (q, J=7 Hz, 2H), 3.37 (s, 2H), 2.81 (m, 4H), 1.23 (t, J=7 Hz, 3H).

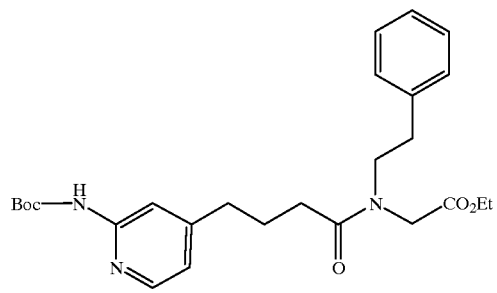

11-4

[4-(2-Boc-aminopyzidin-4-yl)butanoyl]-N-(2-phenethyl) glycine ethyl ester (11-4)

A solution of acid 4-1 (1.5 g, 5.35 mmol), amine 11-3 (1.66 g, 8.03 mmol), BOP reagent (2.61 g, 5.89 mmol), NMM (3.0 ml, 21.4 inmol) and CH₃CN (30 ml) was stirred at ambient temperature for 18 h. The solution was diluted with EtOAc and then washed with H₂O, sat. NaHCO₃, 10% KHSO₄, brine, dried (MgSO₄) and concentrated. Flash chromatography (silica, 50% EtOAc/hexanes 80% EtOAc/hexanes) furnished ester 11-4 as a yellow solid.

TLC $R_f$ 0.35 (silica, 50% EtOAc/hexanes)

$^1$H NMR (400 MHz, CDCl₃) δ8.12 (d, J=5 Hz, 1H), 7.77 (m, 2H), 7.21 (m, 4H), 7.10 (d, J=7 Hz, 1H), 6.79 (m, 1H), 4.18 (q, J=7 Hz, 2H), 4.02 (s, 2H), 3.58 (m, 2H), 2.82 (m, 2H), 2.62 (t, J=7 Hz, 0.64H), 2.57 (t, J=7 Hz, 1.36H), 2.15 (m, 2H), 1.91 (m, 2H), 1.52 (s, 9H), 1.27 (m, 3H).

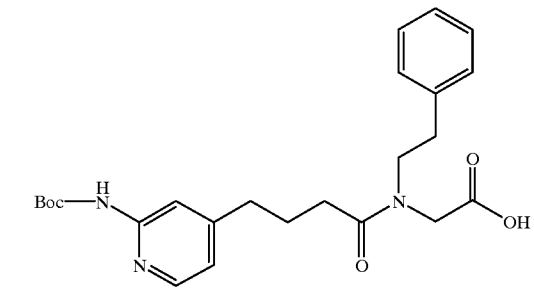

11-5

[4-(2-BOC-Aminopyridin-4-yl)butanoyl]-N-(2 phenethyl) glycine (11-5)

A solution of ester 11-4 (1.8 g, 3.84 mmol), 1N NaOH (6 ml, 6 mmol) and EtOH (10 ml) was stirred at ambient temperature for 30 minutes. The solution was acidified with 10% KHSO₄ and then extracted with EtOAc. The EtOAc phase was washed with brine, dried (MgSO₄) and concentrated to furnish acid 11-5 as a yellow solid.

TLC $R_f$ 0.80 (silica, 20:1:1 CH₂Cl₂/MeOH/AcOH)

$^1$H NMR (400 MHz, CD₃OD) δ8.12 (m, 1H), 7.17–7.29 (m, 7H), 4.06 (m, 2H), 3.61 (t, J=7 Hz, 2H), 2.85 (t, J=7 Hz, 2H), 2.81 (m, 0.64H), 2.63 (t, J=8 Hz, 1.36H), 2.35 (t, J=7 Hz, 0.64H), 2.14 (t, J=7 Hz, 1.36H), 1.79 (m, 2H), 1.57 (s, 9H).

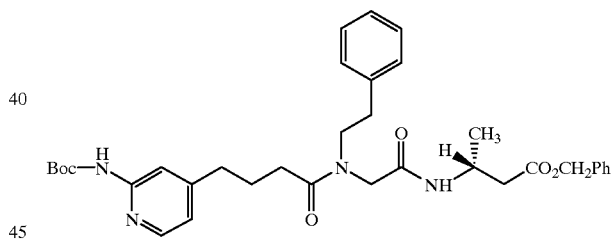

11-7

4-(2-BOC-Aminopyridin-4-yl)butanoyl-N-(2-phenethyl) glycyl-3(R)-methyl-β-alanine benzyl ester (11-7)

A solution of acid 11-5 (400 mg, 0.91 mmol), amine 11-6 (available from Celgene) (285 mg, 1.09 mmol), BOP reagent (440 mg, 0.997 mmol), NMM (502 μl, 3.63 mmol) and CH₃CN (20 ml) was stirred at ambient temperature for 18 h. The solution was diluted with EtOAc and then washed with H₂O, sat. NaHCO₃, 10% KHSO₄, brine, dried (MgSO₄) and then concentrated. Flash chromatography (silica, 80% EtOAc/hexanes) furnished benzyl ester 11-7 as a yellow oil.

TLC $R_f$ 0.49 (silica, EtOAc)

$^1$H NMR (400 MHz, CD₃OD) δ8.06 (d, J=5 Hz, 1H), 7.7 (s, 0.32H), 7.68 (s, 0.68H), 7.09–7.36 (m, 10H), 6.83 (m, 1H), 5.16 (s, 1.36H), 5.08 (s, 0.64H), 4.29 (m, 1H), 3.93 (m, 2H), 3.51 (t, J=7 Hz, 2H), 2.79 (q, J=7 Hz, 2H), 2.50–2.61 (m, 4H), 2.25 (t, J=8 Hz, 0.64H), 2.09 (t, J=7 Hz, 1.36H), 1.73–1.84 (m, 4H), 1.51 (s, 9H), 1.25 (d, J=7 Hz, 3H).

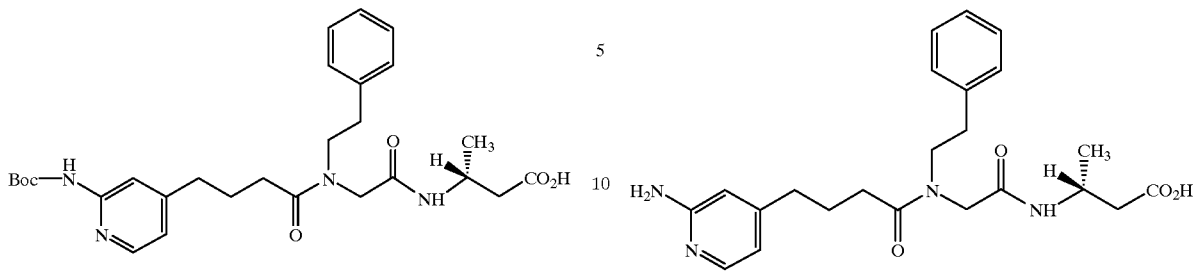

4-(2-BOC-Aminopyridin-4-yl)butanoyl-N-(2-phenethyl) glycyl-3(R)-methyl-β-alanine (11-8)

A solution of benzyl ester 11-7 (380 mg, 0.597 mmol), 1N NaOH (1 ml, 1.0 mmol) and EtOH (5 ml) was stirred at ambient temperature for 1.0 h. The solution was acidified with 10% $KHSO_4$ and then extracted with EtOAc. The EtOAc phase was washed with brine, dried ($MgSO_4$) and concentrated to furnish acid 11-8 as a yellow oil.

$^1$H NMR (400 MHz, $CD_3OD$) δ8.13 (m, 1H), 7.15–7.35 (m, 7H), 4.24 (m, 1H), 3.91 (m, 2H), 3.58 (m, 2H), 2.81 (m, 2.64H), 2.62 (t, J=8 Hz, 1.36H), 2.36 (t, J=7 Hz, 0.64H), 2.14 (t, J=7 Hz, 1.36H), 1.79 (m, 2H), 1.57 (s, 9H), 1.19 (m, 3H).

4-(2-Aminopyridin-4-yl)butanoyl-N-(2-phenethyl)glycyl-3 (R)-methyl-β-alanine (11-9)

A solution of acid 11-8 (320 mg, 0.59 mmol) in $CH_2Cl_2$ (5 ml) was treated with TFA (5 ml). After 1.0 h, the solution was concentrated and then azeotroped with toluene. Flash chromatography (silica, 10:10:1:1 EtOAc/EtOH/$NH_4OH$/$H_2O$) furnished amine 11-10 (210 mg) as a white solid.

TLC $R_f$=0.28 (silica, 5:5:.5:.5 EtOAc/EtOH/$NH_4OH$/$H_2O$)

$^1$H NMR (400 MHz, $CD_3ODD$) δ7.71 (d, J=6 Hz, 1H), 7.15–7.32 (m, 5H), 6.62–6.69 (m, 2H), 4.25 (m, 1H), 3.99 (m, 2H), 3.58 (t, J=7 Hz, 2H), 2.81 (m, 2H), 2.61 (t, J=7 Hz, 0.64H), 2.31–2.51 (m, 3.36H), 2.12 (td, J=3 Hz, 7 Hz, 1.36H), 1.89 (t, J=8 Hz, 0.64H), 1.79 (m, 2H), 1.19 (m, 3H).

SCHEME 12

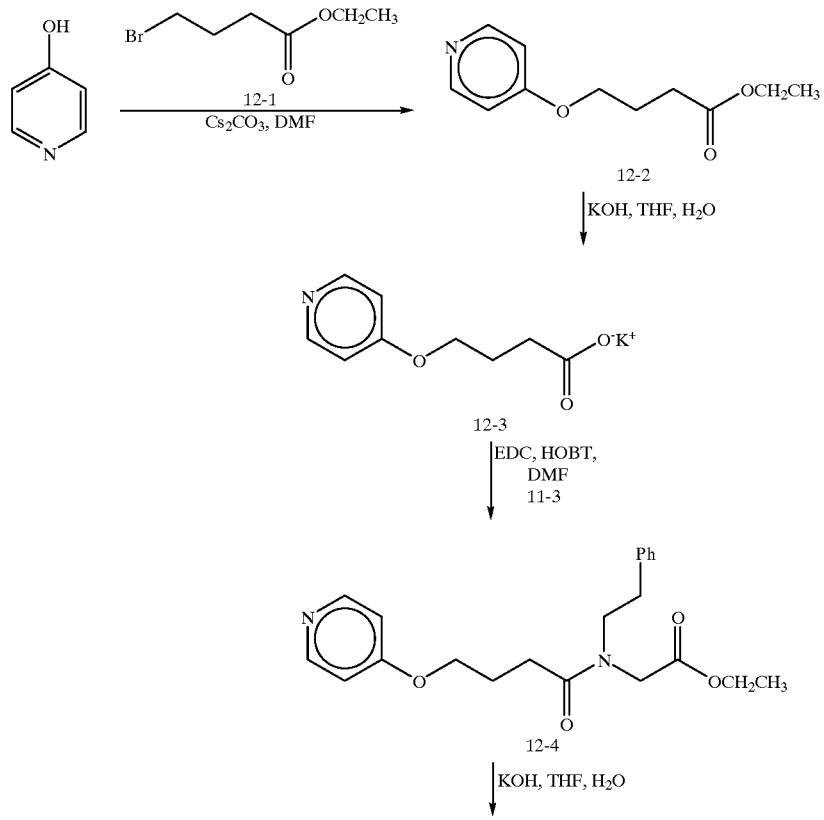

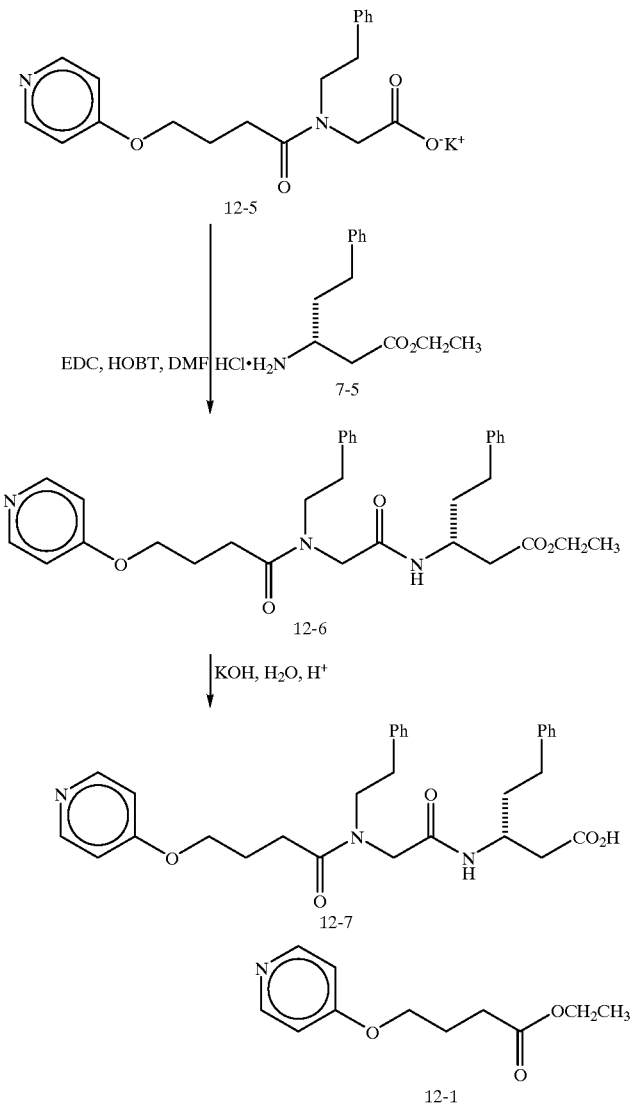

Ethyl-4-(4-Pyridyloxy)butyrate (12-2)

A mixture of 4-hydroxypyridine (10 g, 105 mmol), ethyl 4-bromobutyrate 12-1 (15.0 ml, 105 mmol) and $Cs_2CO_3$ (34.2 g, 105 mmol) in DMF (100 ml) was stirred at room temperature for 24 h. The reaction was filtered and the filtrate diluted with ethyl acetate (300 ml) and washed with water (4×100 ml) and brine (100 ml) then dried ($Na_2SO_4$), filtered, and evaporated. The resulting oil was purified by chromatography on silica gel (3% $CH_3OH/CH_2Cl_2$) to give 12-2 as a colorless glass.

TLC $R_f$ 0.45 (silica, 5% $CH_3OH/CH_2Cl_2$)

$^1$H NMR (300 MHz, $CDCl_3$) δ8.41 (d, J=6.8 Hz, 2H), 6.83 (d, J=6 Hz, 2H), 4.16 (q, J=7 Hz, 2H), 4.07 (t, J=7 Hz, 2H), 2.52 (t, J=7 Hz, 2H), 2.81 (t, J=7 Hz, 2H), 1.23 (t, J=7.0 Hz, 3H).

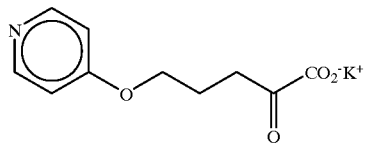

12-3

Potassium 4-(4-pyridyloxy)butyrate (12-3)

The ester 12-1 (2.5 g, 12.0 mmol) was dissolved in 10 ml THF and treated with 0.5 N KOH (24 ml, 12.0 mmol) and $H_2O$ (10 ml). The resulting solution was stirred at room temperature for 78 h then evaporated at reduced pressure to give 12-2 as a white solid.

$^1$H NMR (300 MHz, $D_2O$) δ8.19 (d, J=6.8 Hz, 2H), 6.83 (d, J=6.8 Hz, 2H), 6.83 (d, J=6.8 Hz, 2H), 3.96 (t, J=7.1 Hz, 2H), 2.18 (t, J=7.1 Hz, 2H), 1.93 (m, 2H).

12-4

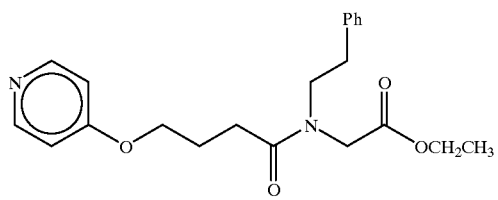

4-(4-Pyridyloxy)butyrate-N-(2-phenethyl)glycine ethyl ester (12-4)

The alkoxy pyridine 12-3 (298 mg, 1.36 mmol) and amine 11-3 (450 mg, 1.36 mmol) were combined with EDC (260 mg, 136 mmol), HOBT (208 mg, 136 mmol), in DMF (30 ml) and stirred at room temperature for 16 h. The solution was then diluted with ethyl acetate (200 ml) and washed with sat. NaHCO$_3$ (2×100 ml) and brine (100 ml). The organic layer was dried (Na$_2$SO$_4$), filtered, and evaporated and the residue chromatographed on silica gel (3% CH$_3$OH/CH$_2$Cl$_2$) to give 12-4 as a colorless glass.

$^1$H NMR (300 MHz, CDCl$_3$) δ8.41 (d, J=6.5 Hz, 2H), 7.25 (m, 5H), 6.78 (d, J=6.5 Hz, 2H), 61.23 (m, 2H), 4.02 (s, 2H), 4.00 (m, 2H), 3.63 (m, 2H), 3.41 (m, 2H), 2.15 (m, 2H), 1.31 (m, 3H).

12-6

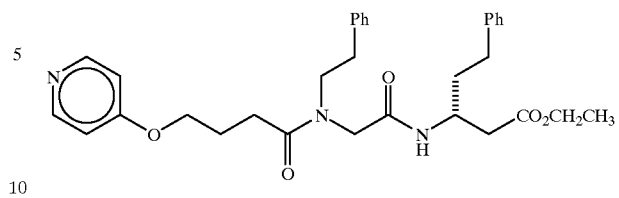

4-(Pyridyloxy)butyrate-N-(2-phenethyl)glycyl-3(R)-2-phenethyl-β-alanine ethyl ester (12-6)

Acid salt 12-5 (352 mg, 0.93 mmol) and amino ester 7-5 (240 mg, 193 mmol), HOBT (142 mg, 0.93 mmol), EDC (198 mg, 0.93 mmol), and triethylamine (130 μl, 0.93 mmol) was dissolved in DMF (15 ml) and stirred at room temperature for 18 h. The solution was diluted with ethyl acetate (200 ml) washed with sat. NaHCO$_3$, water and brine (100 ml each), dried (Na$_2$SO$_4$) and concentrated to give a colorless oil. Chromatography on silica gel afforded 12-6 as a colorless glass.

TLC R$_f$ 0.50 (silica, 3% CH$_3$OH/CH$_2$C$_2$)

$^1$H NMR (300 MHz, CDCl$_3$) δ8.40 (d, J=6.6 Hz, 2H), 7.25 (m, 10H), 6.85 (t, J=7.4 Hz, 1H), 7.25 (d, J=6.6 Hz, 2H), 4.25 (m, 1H), 4.18 (m, 2H), 4.00 (m, 2H), 3.60 (m, 2H), 2.95 (m, 2H), 2.63 (m, 2H), 2.58 (m, 2H), 2.40 (m, 2H), 2.08 (m, 2H), 1.85 (m, 2H), 1.16 (m, 3H).

12-5

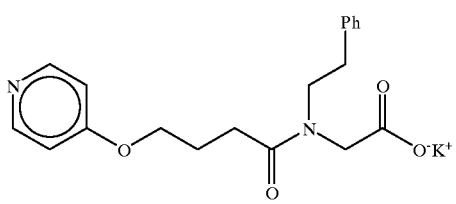

4-(4-Pyridyloxy)butyrate-N-(2-phenethyl)glycine potassium salt (12-5)

Ester 124 (360 mg, 0.97 mmol) was hydrolyzed in 0.5 N KOH (1.94 ml, 0.97 mmol) to give the potassium salt 12-5 as a white solid.

$^1$H NMR (300 MHz, DMSO-d$_6$) δ8.38 (d, J=6.5 Hz, 2H), 7.25 (m, 5H), 6.93 (d, J=6.5 Hz, 2H), 4.016 m, 2H), 3.45 (m, 2H), 3.25 (s, 2H), 2.68 (m, 2H), 2.21 (m, 2H), 1.86 (m, 2H).

12-7

4-(4-Pyridyloxy)butyrate-N-(2-phenethyl)glycyl-3(R)-2-phenethyl-β-alanine (12-7)

Ester 12-6 (123 mg, 0.23 mmol) was hydrolyzed with 0.5 N KOH and the acid was isolated as its TFA salt following preparative reverse phase chromatography.

$^1$H NMR (300 MHz, CD$_3$OD) δ8.63 (d, J=6.5 Hz, 2H), 7.52 (d, J=6.5 Hz, 2H), 7.20 (m, 10H), 4.41 (m, 1H), 4.32 (m, 2H), 4.01 (m, 2H), 3.81 (m, 2H), 2.85 (m, 2H), 2.63 (m, 2H), 2.30 (m, 2H), 2.41 (m, 2H), 2.20 (m, 2H), 1.85 (m, 2H).

SCHEME 13

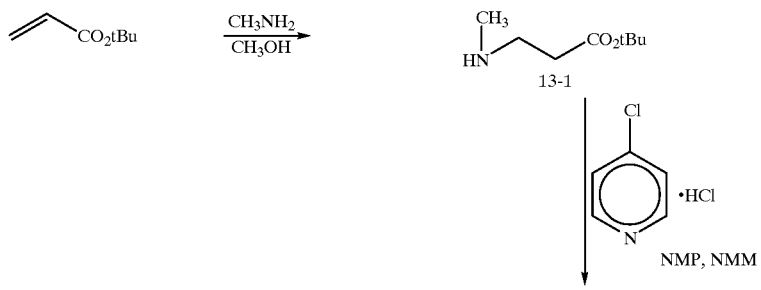

-continued
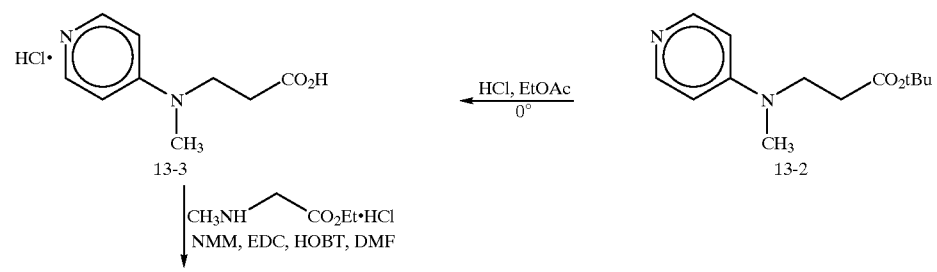
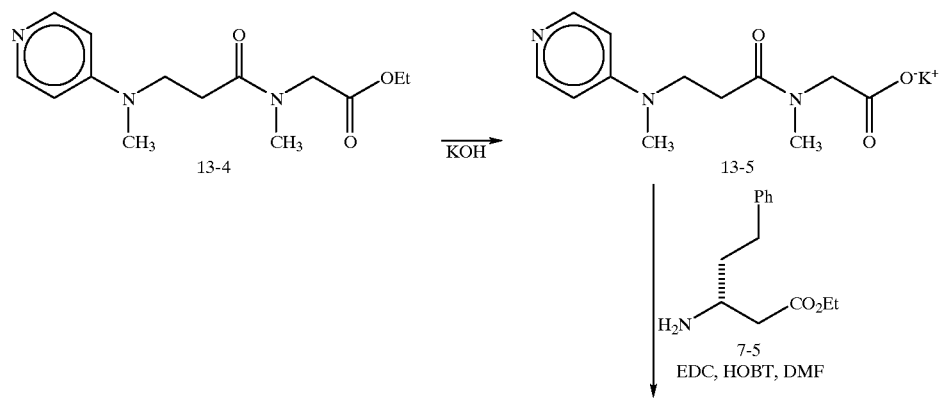
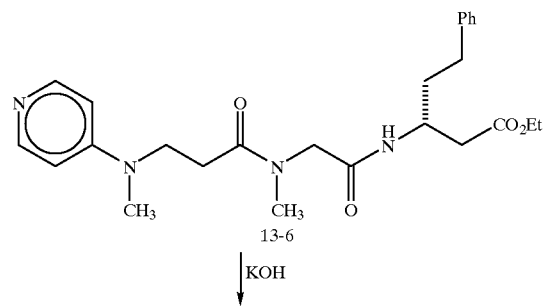
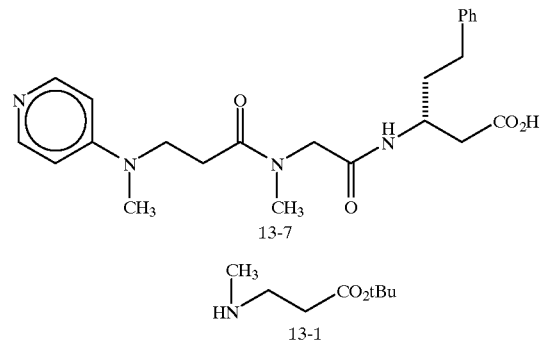

tert-Butyl 3-N-methylaminopropionate (13-1)

Tert-butyl acrylate (15 g, 117 mmol) was added to a solution or methanol saturated with $CH_3NH_2$ (300 ml) and stirred at room temperature for 16 h. The solution was evaporated to afford 13-1 as a colorless liquid.

$^1$H NMR (300 MHz, CDCl$_3$) δ2.81 (t, J=7.2 Hz, 2H), 2.43 (t, J=7.2 Hz, 2H), 1.45 (s, 9H).

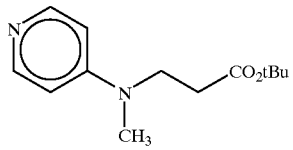

13-2 tert-Butyl 3-[(N-methyl-N-(4-pyridyl)]aminopropionate (13-2)

A mixture of 4-chloropyridine hydrochloride (10 g, 75 mmol), 13-1 (12 g, 75 mmol) and N-methylmorpholine (9.1 ml, 82.5 mmol) in N-methyl pyrrolidinone (100 ml) was heated at 120° C. for 16 h. The solvent was removed at reduced pressure and the residue partitioned between EtOAc (100 ml) and water (50 ml). The organic layer was washed with water and brine (50 ml each) then dried (Na$_2$SO$_4$), filtered and evaporated. The ester 13-2 was isolated as a colorless glass following flash chromatography on silica gel (5% CH$_3$OH/CH$_2$Cl$_2$).

$^1$H NMR (300 MHz, CDCl$_3$) δ8.30 (d, J=6.8 Hz, 2H), 6.91 (d, J=6.8 Hz, 2H), 3.81 (t, J=7.1 Hz, 3H), 3.22 (s, 3H), 2.65 (t, J=7.1 Hz, 2H), 1.41 (s, 9H).

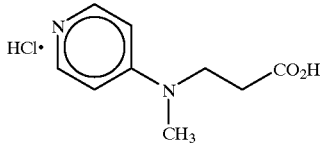

13-3

3-[(N-Methyl-N'-(4-pyridyl)]aminopropionate hydrochloride (13-3)

A solution of 13-2 (2.2 g, 9.3 mmol) in 75 ml anhydrous EtOAc was cooled to 0° and treated with HCl gas for 10 min. The solution was warmed to room temperature and stirred. For 16 h the resulting solid was filtered to give 13-3 as a hygroscopic yellow solid.

$^1$H NMR (300 mHz, DMSO-d$_6$) δ8.26 (d, J=6.8 Hz, 2H), 7.0 (br d, 2H), 3.82 (t, J=7.1 Hz, 2H), 3.21 (s, 3H), 2.60 (t, J=7.1 Hz, 2H).

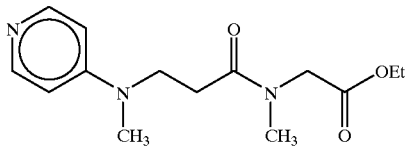

13-4

3-[(N-methyl-N-(4-pyridyl)]aminoprolionyl-sarcosine ethyl ester (13-4)

Acid 13-3 (383 mg, 1.5 mmol) was coupled with sarcosine ethyl ester hydrochloride (253 mg, 1.65 mmol) following the EDC/HOBT procedure previously described to give 13-4 as a colorless glass.

TLC R$_f$ 0.45 (silica, 3% CH$_3$OH/CH$_2$Cl$_2$)

$^1$H NMR (300 MHz, CDCl$_3$) δ8.21 (d, J=6.8 Hz, 2H), 6.51 (d, J=6.8 Hz, 2H), 4.20 (q, J=7.0 Hz, 2H), 4.18 (s, 2H), 3.75 (t, J=7.0 Hz, 2H), 3.09 (s, 3H), 3.04 (s, 3H), 2.65 (t, J=7.0 Hz, 2H), 1.31 (t, J=7.0 Hz, 3H).

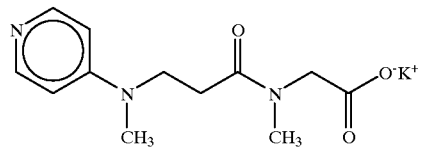

13-5

3-[(N-Methyl)-N'-(4-pyridyl)]aminopropionyl-sarcosine potassium salt (13-5)

A solution of 13-4 (353 mg, 1.26 mmol) in THF (5 ml) was treated with 0.5 N KOH (2.52 ml, 1.21 mmol) and H$_2$O (5 ml) and stirred at room temperature for 18 h. The solvent was removed in vacuo to afford the potassium salt 13-5 as a white solid.

$^1$H NMR (300 MHz, DMSO-d$_6$) δ8.08 (d, J=6.7 Hz, 2H), 6.57 (d, J=6.7 Hz, 2H), 3.61 (t, J=7 Hz, 2H), 3.51 (s, 2H), 2.86 (s, 3H), 2.75 (s, 3H), 2.42 (t, J=7.0 Hz, 2H).

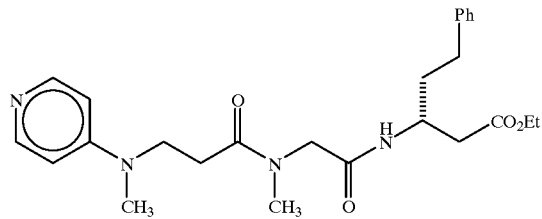

13-6

3-[(N-Methyl)-N'-(4-pyridyl)]aminopropionyl-sarcosine-3 (R)-(2-phenethyl)-β-alanine ethyl ester (13-6)

The acid 13-5 was coupled with 7-5 (229 mg, 0.88 mmol) under the EDC/HOBT procedure to afford 13-6 following chromatography (CH$_2$Cl$_2$/CH$_3$OH/NH$_2$/OH, 90:8:2)

$^1$H NMR (300 MHz, CDCl$_3$) δ8.21 (d, J=6.8 Hz, 2H) 7.25 (m, 2H), 6.73 (d, J=7.0 Hz, 1H), 6.51 (d, J=6.8 Hz, 2H), 4.36 (m, 1H), 61.18 (m, 2H), 3.89 (m, 2H), 3.81 (t, J=7.0 Hz, 2H), 3.06 (s, 3H), 2.98 (s, 3H), 2.85 (m, 2H), 2.65 (m, 2H), 2.51 (m, 2H), 1.83 (m, 2H), 1.20 (m, 3H).

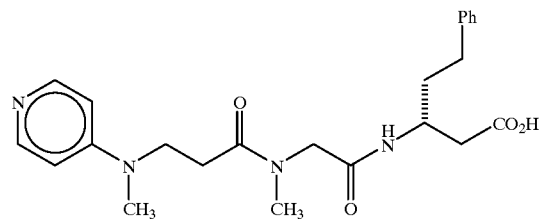

13-7

3-[(N-Methyl)-N'-(4-pyridyl)]aminopropionyl-sarcosine-3 (R)-(2-phenethyl)-β-alanine (13-7)

A solution of the ester 13-6 (75 mg, 0.16 mmol) in THF (5 ml) was treated with 0.5N KOH (320 ml, 0.16 mmol) and H$_2$O (5 ml). The resulting solution was stirred at room temperature for 7.5 h then evaporated at reduced pressure. The resulting residue was purified by reverse phase a white powder.

$^1$H NMR (300 MHz, DMSO-d$_6$) δ8.61 (d, J=6.8 Hz, 2H), 7.25 (m, 5H), 7.18 (d, J=7.0 Hz, 1H), 6.83 (d, J=6.8 Hz, 2H), 4.35 (m, 1H), 3.83 (m, 2H), 3.81 (t, 2H), 3.13 (s, 2H), 2.95

(s, 3H), 2.85 (m, 2H), 2.65 (m, 2H), 2.56 (m, 2H), 1.86 (m, 2H).

SCHEME 14

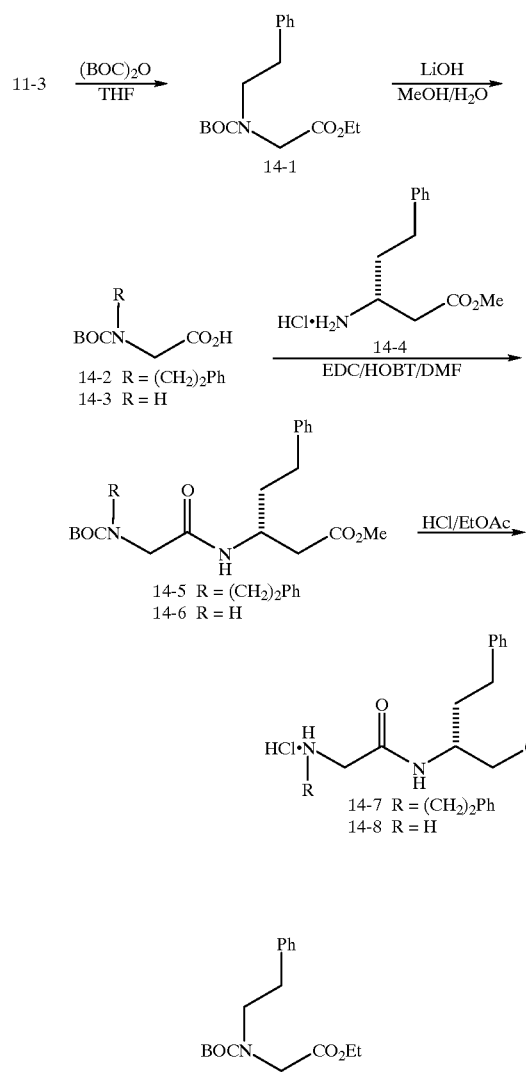

N-(t-Butoxycarbonyl)-N-(2-phenylethyl)glycine ethyl ester (14-1)

The amine 11-3 (1.11 g, 5.36 mmol) and (BOC)$_2$O (1.28 g, 5.9 mmol) in 10 ml THF were stirred for 48 h under argon. Removal of the solvent in vacuo gave a yellow oil which was purified by chromatography (silica, hexane/EtOAc 9:1) to afford 14-1 as a colorless oil.

R$_f$ (silica, hexane/EtOAc 9:1) 0.41.

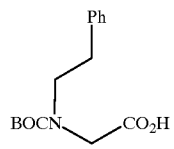

N-(t-Butoxycarbonyl)-N-(2-phenylethyl)glycine (14-2)

A solution of the ester 14-1 (1.7 g, 5.5 mmol), 11.1 mL 1N LiOH and 11 mL MeOH was stirred at room temperature for 16 h. The mixture was poured into water/EtOAc and acidified with 1N HCl to pH≈3. After extraction with EtOAc (2×), the organic layers were washed with brine, dried (MgSO$_4$) and evaporated to give 14-2 as a foam which was used as such in the next step.

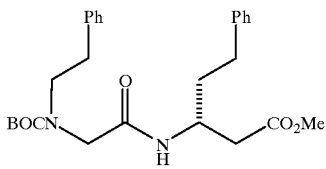

N—[N-(t-Butoxycarbonyl)—N'-(2-phenylethyl)glycyl-3(R)-(2-phenylethyl)-β-alanine methyl ester (14-5)

The acid 14-5 (502 mg, 1.8 mmol), 3(R)-(2-phenylethyl)-β-alanine methyl ester hydrochloride 14-4 (see U.S. Pat. No. 5,281,585) (482 mg, 2.0 mmol), HOBT (267 mg, 2.0 mmol), EDC hydrochloride (515 mg, 2.7 mmol) and N-methylmorpholine (0.22 ml, 2.0 mmol) were stirred in 10 ml DMF for 16 h under argon. After pouring the solution into EtOAc/10% citric acid (aqueous solution) the mixture was extracted twice with EtOAc, washed with water then brine, dried (MgSO$_4$) and the solvent removed in vacuo. The residual yellow oil was subjected to column chromatography (silica, hexane/EtOAc 1:1) to give 14-5 as a colorless oil.

R$_f$ (silica, hexane/EtOAc 1:1) 0.44.

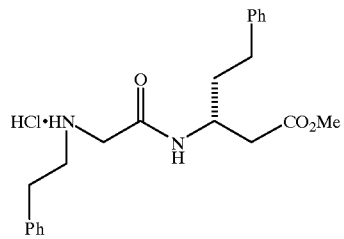

N—[N'-(2-phenethyl)glycyl]-3(R)-(2-phenethyl)-β-alanine methyl ester hydrochloride (14-7)

A solution of 14-5 (719 mg, 1.5 mmol) in 40 mL of EtOAc was treated with HCl (g) until saturated. After 30 min the solvent was removed in vacuo and the residue was triturated with ether from which 14-10 crystallized as a white solid.

$^1$H NMR (CD$_3$OD) δ1.87 (2H, m), 2.5–2.8 (4H, m), 3.05 (2H, m), 3.28 (2H, m), 3.62 (3H, s), 3.78 (1H, d), 3.84 (1H, d), 4.26 (1H, m), 7.1–7.4 (10H, m).

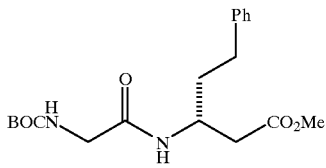

N—[N'-(t-Butoxycarbonyl)glycyl]-3(R)-(2-phenethyl)-β-alanine methyl ester (14-6)

N-(t-butoxycarbonyl)glycine 14-3 (Aldrich) was coupled with 14-4 according to the procedure described for the preparation of 14-5. The title compound 14-6 was purified by column chromatography (silica, hexane/EtOAc 1:1).

$R_f$ (silica, hexane/EtOAc 1:1) 0.22.

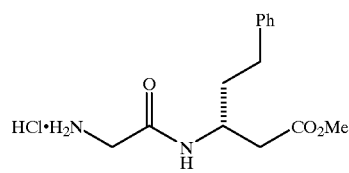

14-8

N-Glycyl-3(R)-(2-phenethyl)-β-alanine methyl ester hydrochloride (14-8)

Following the procedure described for the preparation of 14-7 compound 14-6 was converted into 14-8.

$^1$H NMR (CD$_3$OD) δ1.88 (2H, m), 2.5–2.8 (4H, m), 3.64 (5H, s), 4.25 (1H, m), 7.1–7.3 (5H, m).

SCHEME 15

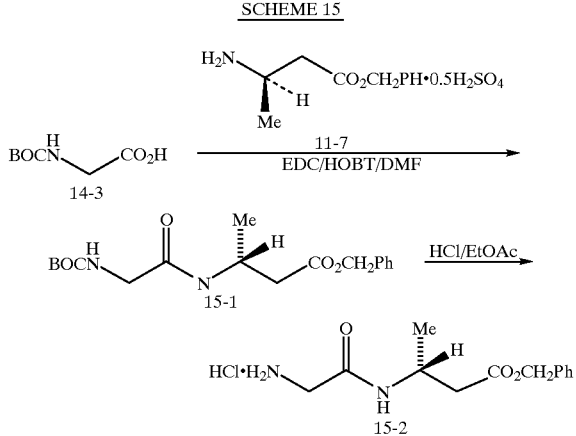

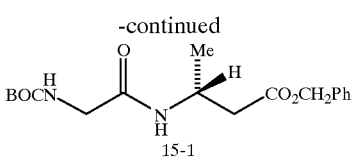

15-1

N—[N'-(t-Butoxycarbonyl)glycyl]-3(R)-methyl-β-alanine benzyl ester (15-1)

N-(t-Butoxycarbonyl)glycine 14-3 (Aldrich) was coupled with 3(R)-methyl-β-alanine benzyl ester 0.5 H$_2$SO$_4$, 11-7 (Celgene) according to the procedure described for the preparation of 14-5. The title product 15-1 was then obtained by chromatography (silica, hexane/EtOAc 2:3).

$R_f$ (silica, hexane/EtOAc 1:1) 0.3.

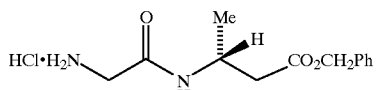

15-2

N-(Glycyl-3(R)-methyl-β-alanine benzyl ester hydrochloride (15-2)

Following the procedure for the preparation of 14-7, compound 15-1 was converted into 15-2 which was isolated as a white solid.

$^1$H NMR (CD$_3$OD) δ1.22 (3H, d), 2.58 (2H, m), 3.53 (1H, d), 3.63 (1H, d), 6.3 (2H, s), 7.35 (5H, m).

SCHEME 16

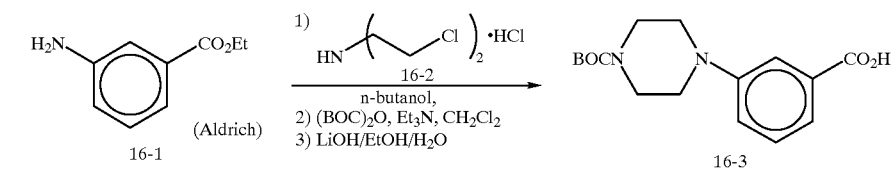

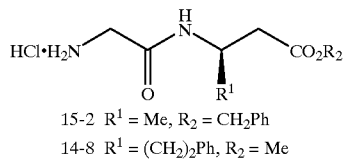

15-2 R$^1$ = Me, R$_2$ = CH$_2$Ph
14-8 R$^1$ = (CH$_2$)$_2$Ph, R$_2$ = Me

EDC/HOBT/DMF

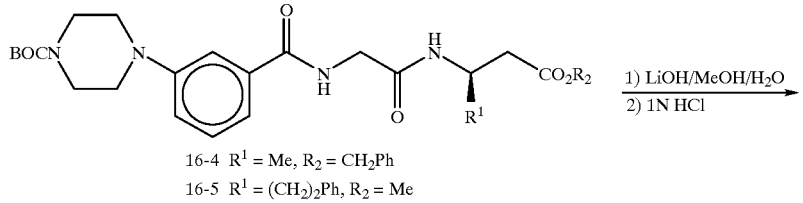

16-4 R$^1$ = Me, R$_2$ = CH$_2$Ph
16-5 R$^1$ = (CH$_2$)$_2$Ph, R$_2$ = Me

1) LiOH/MeOH/H$_2$O
2) 1N HCl

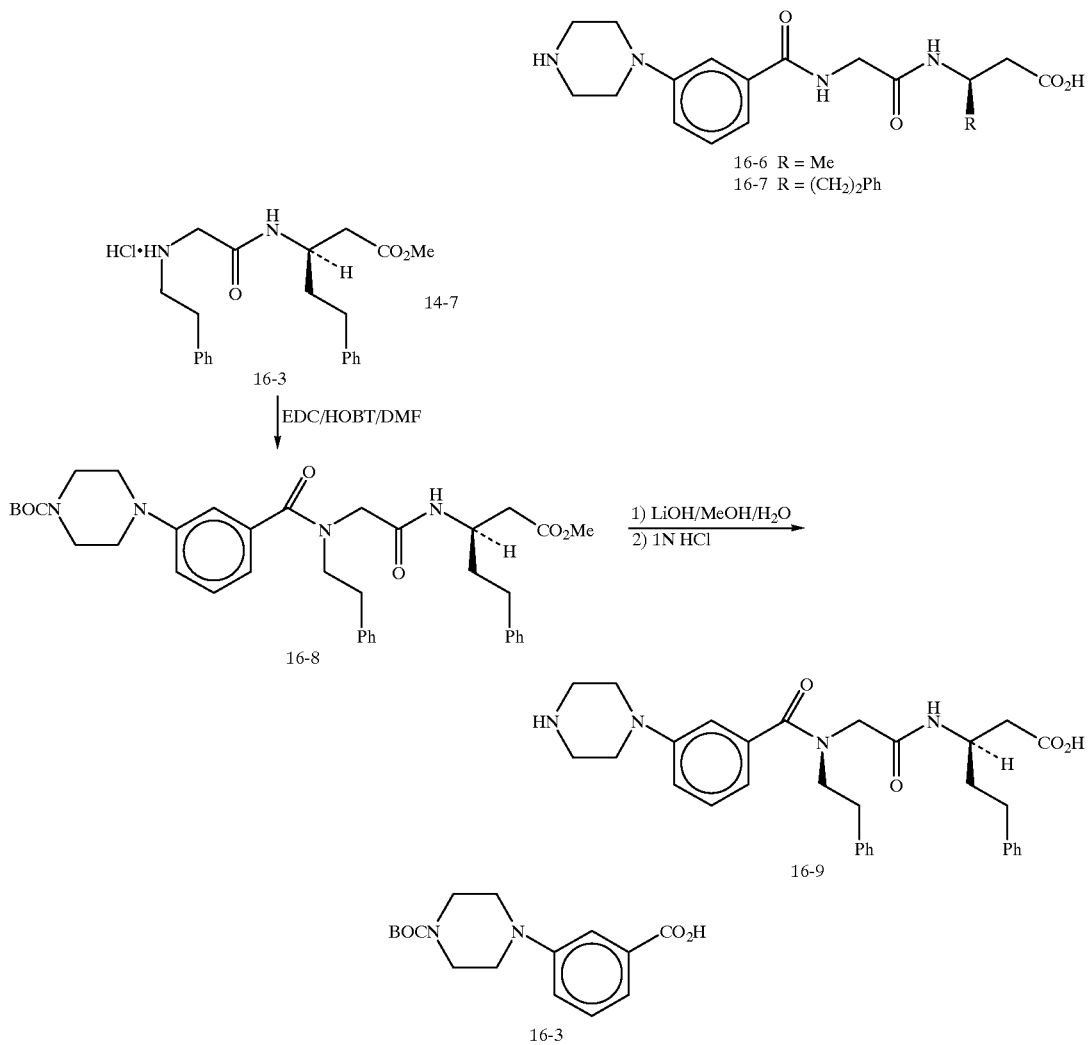

3-(4-t-Butoxycarbonyl-1-piperizinyl)benzoic acid (16-3)

Ethyl 3-aminobenzoate 16-1 (Aldrich, 24.3 g, 0.147 mol) and bis(2-chloroethyl)amine hydrochloride 16-2 (Aldrich, 26.3 g, 0.147 mol) were heated at reflux in 500 mL n-butanol for 24 h. The solution was concentrated in vacuo, the residue was taken up in EtOAc and washed successively with saturated aqueous $NaHCO_3$ then brine. After drying ($MgSO_4$), the solvent was removed and the resulting black oil chromatographed (silica, EtOAc then EtOAc/MeOH 1:1 then MeOH) to give the corresponding piperizine derivative as a mixture of ethyl and butyl esters.

This piperazine (17.8 g, 76 mmol) was dissolved in 500 mL dry $CH_2Cl_2$ and $Et_3N$ (13.3 ml, 95.6 mmol) was then added. To this cooled $-5°$ C. solution was added $(BOC)_2O$ (17.4 g, 79.9 mmol) in 45 ml dry $CH_2Cl_2$ and stirring was continued until the reaction was complete (as monitored by TLC). The solution was poured into 10% citric acid solution then the organic layer was washed with water, saturated aqueous $NaHCO_3$ and brine. After drying over $MgSO_4$, the solvent was removed in vacuo to give a brown oil. Silica gel chromatography (hexane/EtOAc 1:1) gave the BOC-protected piperazine as a mixture of ethyl and butyl esters.

The BOC-protected piperazine (22.1 g) was dissolved in 150 ml 1N LiOH and 600 ml absolute ethanol and this solution was heated at reflux for 16 h. After removal of the ethanol, EtOAc and 10% citric acid solution were added. The organic layer was washed with 1N NaOH, the aqueous layer was then re-acidified with 1N HCl and extracted with EtOAc. This EtOAc extract was washed with brine, dried ($MgSO_4$) and concentrated to give 16-3 as a white solid.

$R_f$ (silica, hexane/EtOAc 1:1) 0.22.

$^1H$ NMR ($CDCl_3$) $\delta$1.49 (9H, s), 3.21 (4H, br t), 3.61 (4H, br t), 7.16 (1H, dd), 7.36 (1H, t), 7.64 (2H, m).

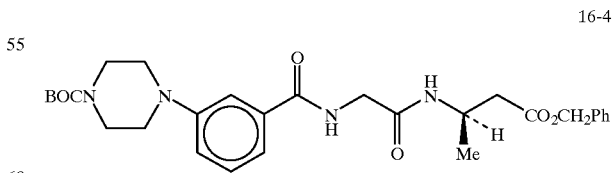

16-4

N-{N'-3-(4-t-Butoxycarbonyl-1-piperizinyl)benzoyl)glycyl}-3(R)-methyl-β-alanine benzyl ester (16-4)

The acid 16-3 was coupled with 15-2 according to the procedure described for the preparation of 14-5 to yield 16-4.

$R_f$ (silica, EtOAc) 0.45.

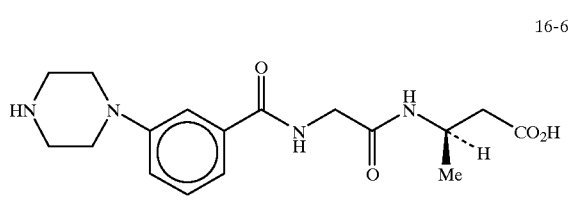

16-6

N—[N'-[3-(1-Piperazinyl)benzoyl]glycyl]-3(R)-methyl-β-alanine trifluoroacetic acid salt (16-6)

The ester 16-4 (452 mg, 0.84 mmol) was dissolved in 4 ml MeOH, treated with 1N LiOH (2.5 ml, 2.5 mmol) and stirred for 48 h. The solvent was removed under reduced pressure and to the residue was added 10 ml 1N HCl. After 10 min, the solution was concentrated and the residue purified by preparative HPLC ($H_2O/CH_3CN$ with 0.1% TFA, gradient) to give 16-6.

FAB mass spectrum m/z=349 (m+1)

$^1$H NMR ($CD_3OD$) δ1.22 (3H, d), 2.43 (1H, dd), 2.57 (1H, dd), 3.38 (4H, m), 3.46 (4H, m), 3.96 (1H, d), 4.04 (1H, d), 4.30 (1H, sextet), 7.25 (1H, m), 7.4 (2H, m), 7.5 (1H, m).

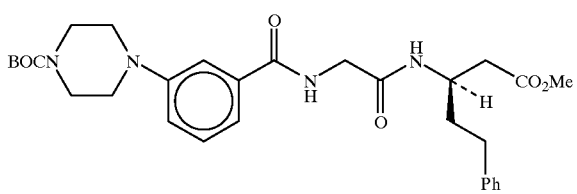

16-5

N—[N'-[3-(4-t-Butoxycarbonyl-1-piperazinyl)benzoyl]glycy ]-3(R)-(2-phenethyl)-β-alanine methyl ester (16-5)

The acid 16-3 was coupled with 14-8 according to procedure described for the preparation 14-5 to yield 16-5.

$^1$H NMR ($CDCl_3$) δ1.49 (9H, s), 1.90 (2H, m), 2.58 (2H, d), 2.63 (2H, m), 3.15 (6H, m), 3.55 (4H, m), 3.62 (3H, s), 4.10 (2H, d), 4.32 (1H, m), 7.0–7.5 (9H, m).

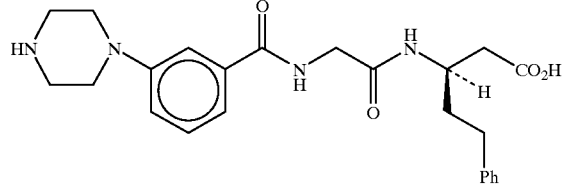

16-7

N—[N'-[3-(1-Piperazinyl)benzoyl]glycyl]-3(R)-(2-phenethyl)-β-alanine trifluoroacetic acid salt (16-7)

Following the procedure described for the preparation of 16-6, 16-5 was converted into 16-7.

FAB mass spectrum m/z=439 (m+1)

Anal. calcd. for $C_{24}H_{30}N_4$. 1.35TFA. 1.0$H_2O$ C, 52.53; H, 5.51; N, 9.18.

found: C, 52.57; H, 5.44; N, 9.26.

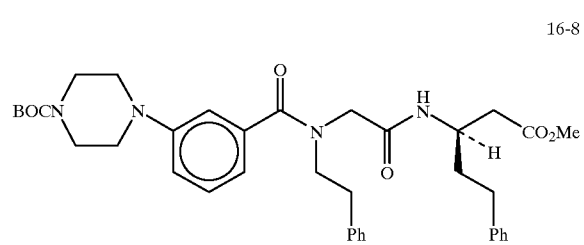

16-8

N—[N'-[3-(4-t-Butoxycarbonyl-1-piperazinyl)benzoyl]-N'-(2-phenethyl)glycyl]-3(R)-(2-phenethyl)-β-alanine methyl ester (16-8)

The acid 16-3 was coupled with 14-7 according to the procedure described for the preparation of 14-5 to yield 16-8.

$R_f$ (silcia, EtOAc/hexane 2:1) 0.37.

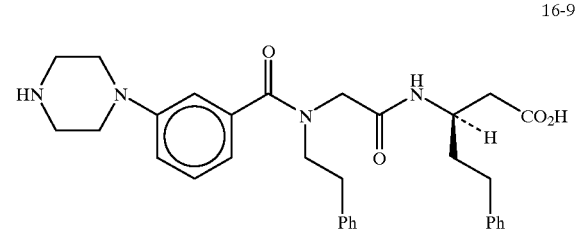

16-9

N—[N'-[3-(1-Piperazinyl)benzoyl]-N'-(2-phenethyl)glycyl]-3(R)-(2-phenethyl)-β-alanine trifluoroacetic acid salt (16-9)

Following the procedure described for the preparation of 16-6, 168 was converted into 16-9.

FAB mass spectrum m/z=543 (m+1)

Anal. calcd. for $C_{32}H_{38}N_4O_4$. 1.8TFA. 0.8$H_2O$ C, 56.09; H, 5.47; N, 7.35.

found: C, 56.09; H, 5.41; N, 7.74.

SCHEME 17

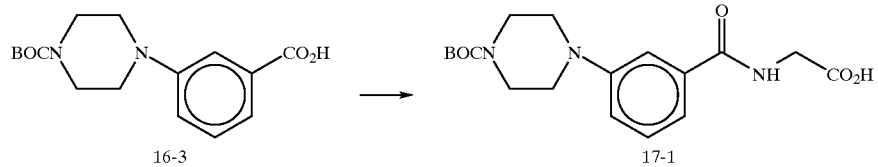

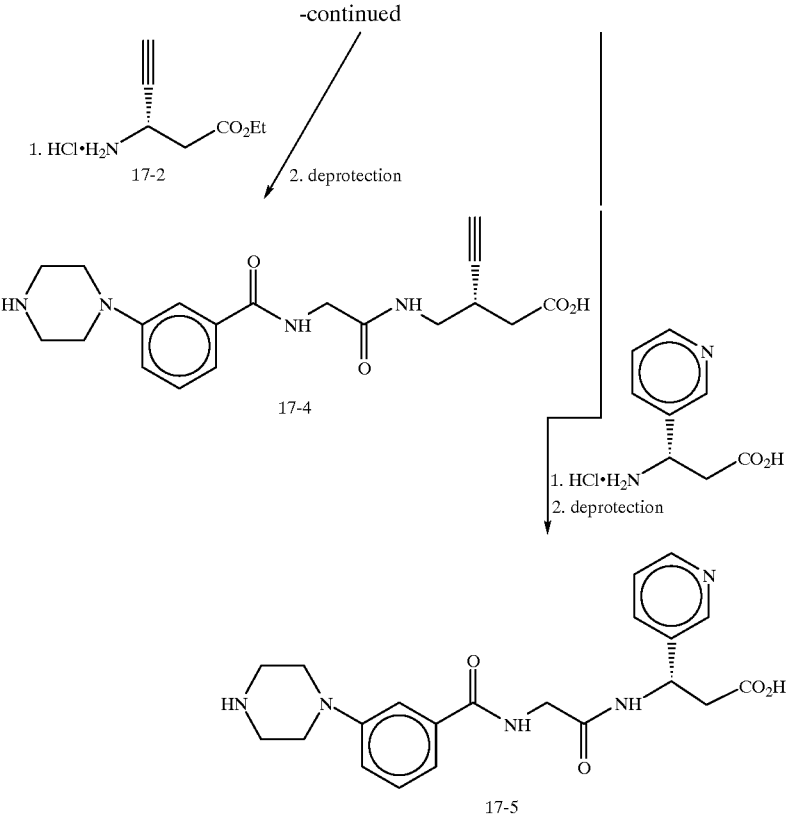

3-(4-t-Butoxycarbonyl-1-piperazinyl)benzoyl glylcine (17-1)

The acid 16-3 was coupled with glycine ethyl ester followed by hydrolysis of the resulting ester using previously described chemistry to yield 17-1.

$^1$H NMR (300 MHz, CD$_3$OD) δ1.48 (9H, s), 3.22 (4H, m), 3.59 (4H, m), 4.08 (2H, s), 7.22 (1H, m), 7.40 (2H, m), 7.55 (1H, s).

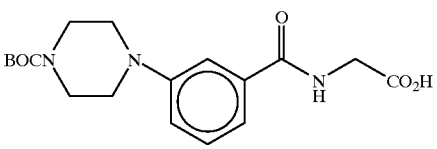

N—[N'-[3-(1-Piperazinyl)benzoyl]glycyl]-3(S)-ethynyl-β-alanine trifluoroacetic acid salt (17-4)

The acid 17-1 was coupled with 3(S)-ethynyl-β-alanine ethyl ester hydrochloride (Zablocki et al., *J. Med. Chem.*, 1995, 38, 2378–2394) using standard peptide coupling conditions. The product was then fully deprotected using previously described methodology to give, after reverse phase chromotography, 17-4 as the trifluoroacetate salt.

FAB mass spectrum m/z=359 (M+1)

Anal. calculated for C$_{18}$H$_{22}$N$_4$O$_4$. 1.10TFA. 0.30H$_2$O C, 49.59; H, 4.88; N, 11.45.

Found: C, 49.58; H, 4.80; N, 11.57.

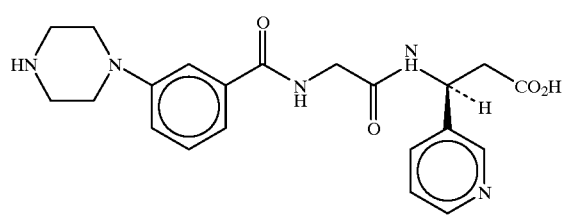

N—{N'-[3-(1-Piperazinyl)benzoyl]glycyl}-3(S)-(3-pyridyl)-β-alanine trifluoroacetic acid salt (17-5)

The acid 17-1 was coupled with 3(S)-(3-pyridyl)-β-alanine ethyl ester hydrochloride (Rico et al., *J. Org Chem.*, 1993, vol. 58, p. 7948) using standard peptide coupling conditions. The product was then fully deprotected using previously described methodology to give, after reverse phase chromatography, 17-5 as the trifluoroacetate salt.

FAB mass spectrum m/z=412 (M+1)

Anal. calculated for C$_{21}$H$_{25}$N$_5$O$_4$. 2.55TFA. 0.75 H$_2$O C, 43.80; H, 4.09; N, 9.79.

Found: C, 43.76; H, 3.98; N, 10.15.

SCHEME 18

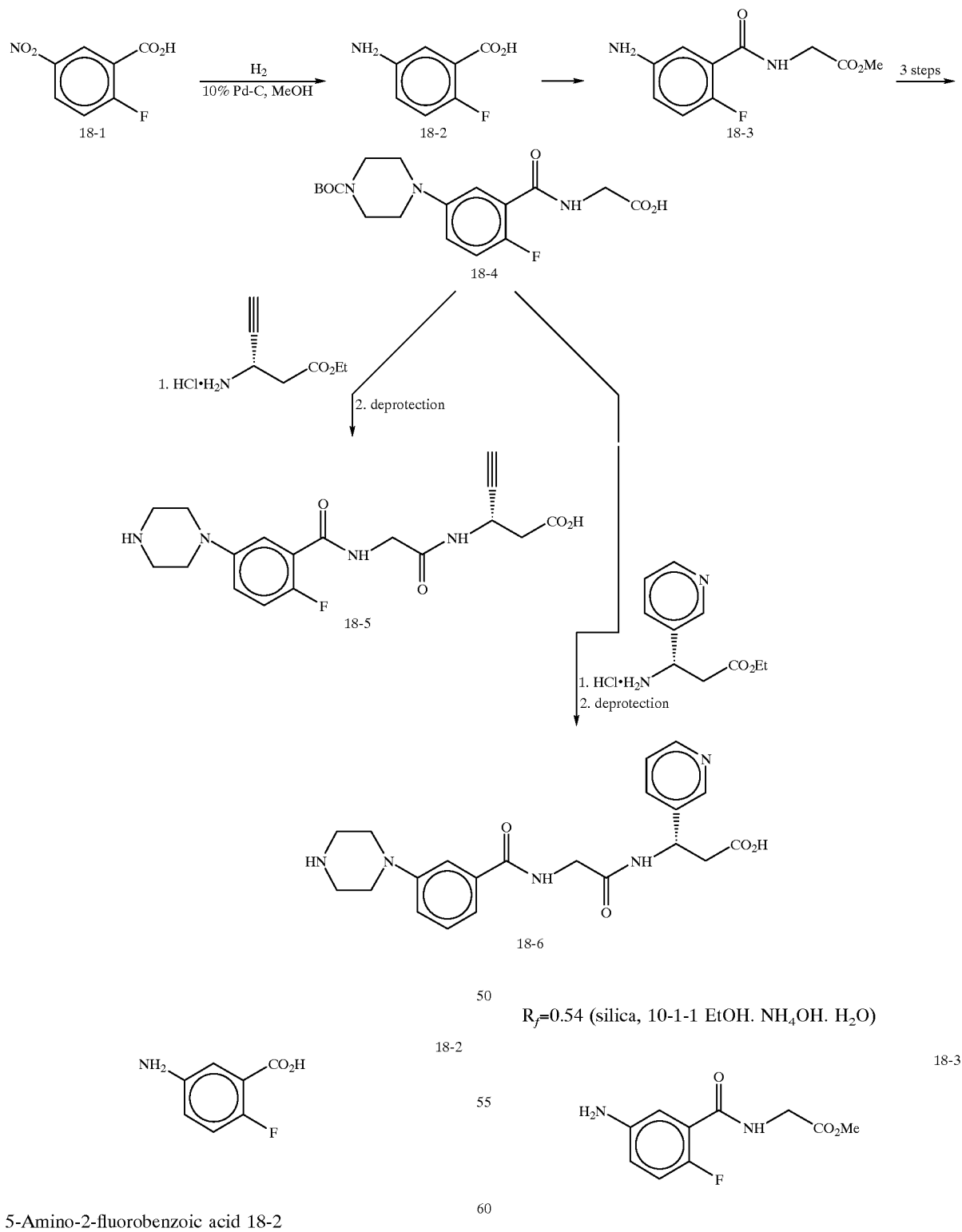

$R_f$=0.54 (silica, 10-1-1 EtOH. NH$_4$OH. H$_2$O)

5-Amino-2-fluorobenzoic acid 18-2

2-Fluoro-5-nitrobenzoic acid 18-1 (Aldrich) was reduced using 10% Pd-C catalyst in MeOH under an atmosphere of H$_2$ to give, after filtration of the catalyst and removal of the solvent, 18-2 as a solid.

N-(5-Amino-2-Fluorobenzoyl)glycine methyl ester 18-3

The acid 18-2 was coupled with glycine methyl ester using standard peptide coupling conditions to give 18-3.

$R_f$=0.65 (silica; EtOAc/MeOH 9:1)

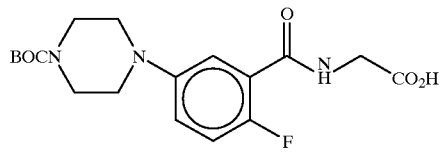

18-4

5-(4-t-Butoxycarbonyl-1-piperizinyl)-2-fluoro benzoyl Livcine 18-4

Following the procedure described for the preparation of 16-3, the aniline 13 was converted into the piperazine-acid 18-4

$^1$H NMR (300 MHz, CD$_3$OD) δ1.46 (9H, s), 3.11 (4H, m), 3.58 (4H, m), 4.12 (2H, s), 7.05–7.21 (2H, m), 7.40 (1H, m).

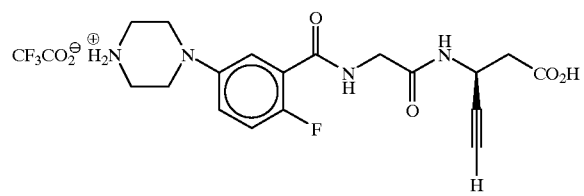

18-5

N—{N'-[2-Fluoro-5-(1-piperazinyl)benzoyl]glycyl}-3(S)-ethynyl-β-alanine trifluoro acetic acid salt 18-5

Following the procedure described for the preparation of 17-4, compound 18-4 was converted into 18-5.

FAB mass spectrum m/z=377 (M+1)

Anal. calculated for C$_{18}$H$_{21}$N$_4$O$_4$F. 1.30TFA. 0.50H$_2$O C, 46.37; H, 4.40; N, 10.50.

Found: C, 46.34; H, 4.37; N, 10.58.

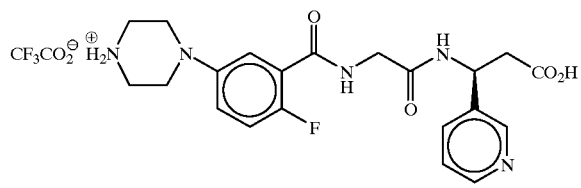

18-6

N—{N'-[2-fluoro-5-(1-piperazinyl)benzoyl]glycyl}-3(S)-(3-pyridyl)-β-alanine trifluoroacetic acid salt 18-6

Following the procedure described for the preparation of 17-5, compound 18-4 was converted into 18-6.

FAB mass spectrum m/z=430 (M+1)

Analysis calculated for C$_{21}$H$_{24}$N$_5$O$_4$F. 2.65TFA. 0.90H$_2$O C, 42.24; H, 3.83; N, 9.37.

Found: C, 42.25; H, 3.81; N, 9.71.

SCHEME 19

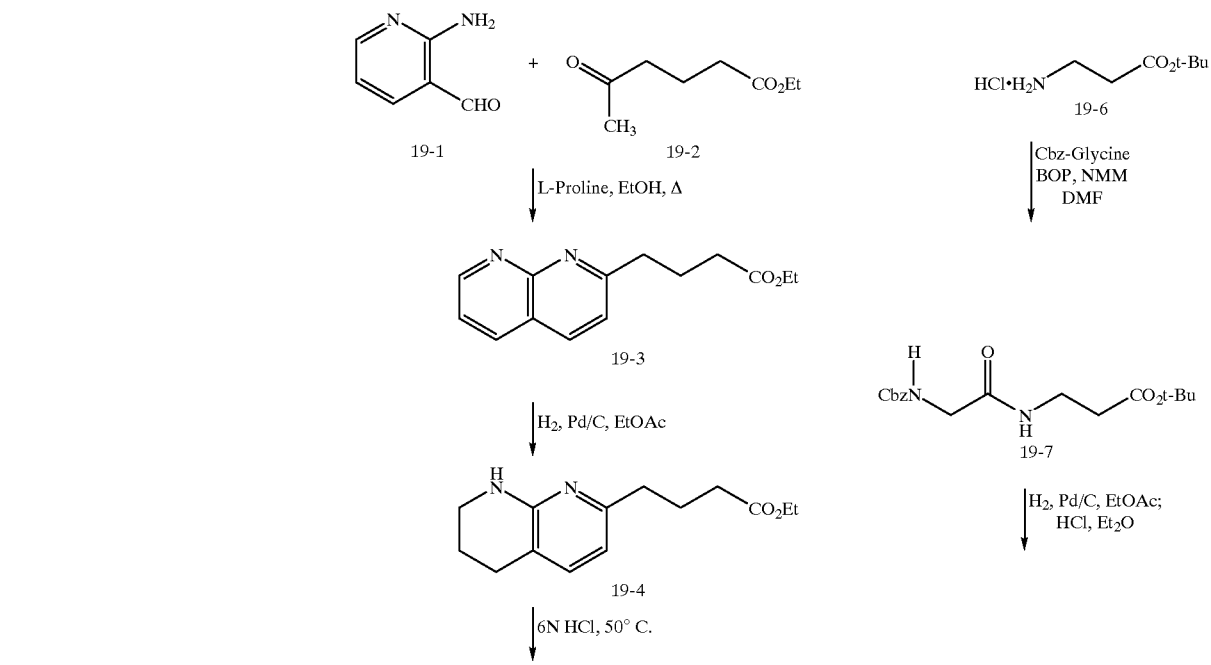

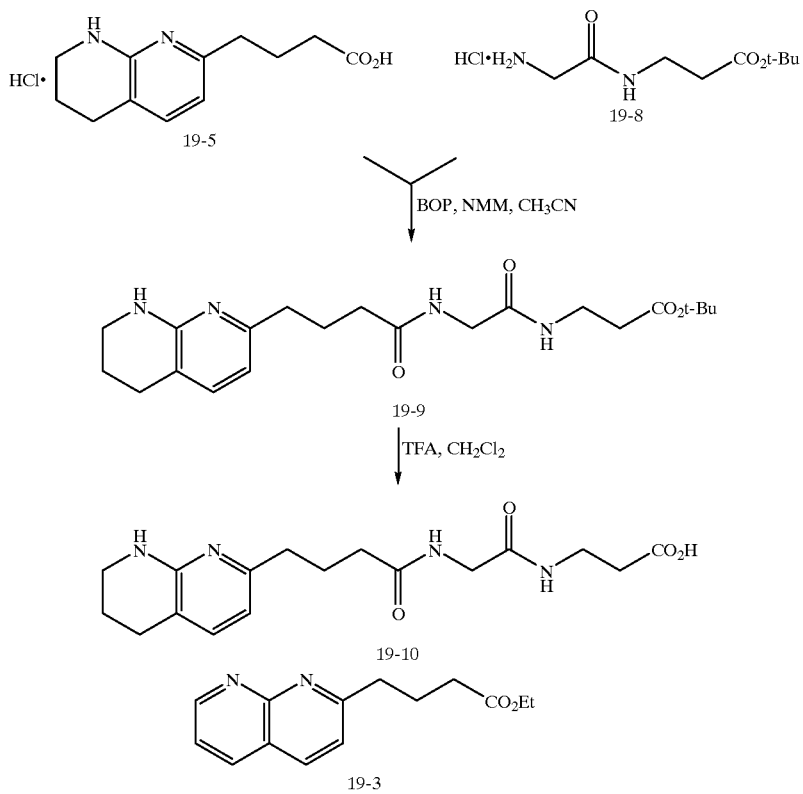

Ethyl 4-(1,8-naphthyrdin-2-yl)butanoate (19-3)

Aminoaldehyde 19-1 (2.02 g, 16.6 mmol, prepared according to *Het.* 1993, 36, 2513), ketone 19-2 (5.3 mL, 33.1 mmol) and L-proline (0.48 g, 4.17 mmol) were combined in 75 mL EtOH. After heating at reflux 10 overnight the reaction was concentrated. Flash chromatography (silica, EtOAc) provided 19-3 as an off-white crystalline solid.

TLC $R_f$ 0.23 (silica, EtOAc)

$^1$H NMR (300 MHz, CDCl$_3$): δ9.09 (dd, J=4, 2 Hz, 1H), 8.17 (dd, J=8, 2 Hz, 1H), 8.12 (d, J=8 Hz, 1H), 7.46 (dd, J=8, 4 Hz, 1H), 7.42 (d, J=8 Hz, 1H), 4.12 (q, J=7 Hz, 2H), 3.11 (t, J=8 Hz, 2H), 2.44 (t, J=7 Hz, 1H), 2.26 (qn, J=8 Hz, 2H), 1.25 (t, J=7 Hz, 3H).

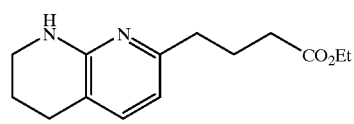

Ethyl 4-(1,2,3,4-tetrahydro-1,8-naphthyridin-7-yl)butanoate (19-4)

A solution of 19-3 (2.3 g, 9.4 mmol) in 50 mL EtOAc was treated with 10% Pd/C (230 mg) and a hydrogen balloon. After 4 d the reaction filtered through celite, concentrated, and purified by flash chromatography (silica, 70% EtOAc/hexane), providing 19-4 as a yellow oil.

TLC $R_f$ 0.40 (silica, EtOAc)

$^1$H NMR (300 MHz, CDCl$_3$): δ7.05 (d, J=7 Hz, 1H), 6.35 (d, J=7 Hz, 1H), 4.73 (br s, 1H), 4.12 (q, J=7 Hz, 2H), 2.69 (t, J=6 Hz, 2H), 2.57 (t, J=8 Hz, 2H), 2.33 (t, J=7 Hz, 2H), 1.98 (m, 2H), 1.90 (m, 2H), 1.25 (t, J=7 Hz, 3H).

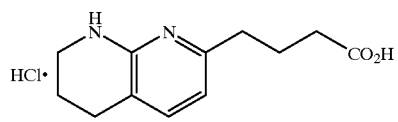

4-(1,2,3,4-Tetrahydro-1,8-naphthyridin-7-yl)butanoic acid hydrochloride (19-5)

Ester 19-4 (1.8 g, 7.25 mmol) in 36 mL 6 N HCl was heated at 50° C. for 4 h, then concentrated, providing 19-5 as a yellow solid.

$^1$H NMR (300 MHz, CD$_3$OD): δ7.59 (d, J=7 Hz, 1H), 6.63 (d, J=7 Hz, 1H), 3.50 (t, J=5 Hz, 2H), 2.82 (t, J=6 Hz, 2H), 2.74 (t, J=8 Hz, 2H), 2.38 (t, J=7 Hz, 2H), 2.02–1.90 (m, 4H).

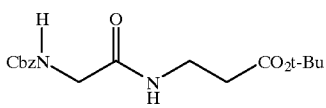

N—Cbz-Glycyl-β-alanine t-butyl ester (19-7)

N—CBz-Glycine (1.0 g, 4.78 mmol), amine 19-6 (0.91 g, 5.02 mmol), NMM (2.1 mL, 19.1 mmol) and BOP (3.17 g, 7.17 mmol) were combined in 15 mL DMF. After stirring overnight the mixture was concentrated, diluted with EtOAc, washed with water, sat. NaHCO$_3$, water, 5% KHSO$_4$ and brine, dried (MgSO$_4$), filtered and concentrated. Flash chromatography (silica, 60% EtOAc/hexane) provided 19-7 as a colorless oil.

TLC $R_f$ 0.24 (silica, 60% EtOAc/hexane)

$^1$H NMR (400 MHz, $d_6$-DMSO): δ7.89 (br t, J=5 Hz, 1H), 7.44 (br t, J=6 Hz, 1H), 7.40–7.30 (m, 5H), 5.02 (s, 2H), 3.56 (d, J=6 Hz, 2H), 3.25 (q, J=6 Hz, 2H), 2.35 (t, J=7 Hz, 2H), 1.40 (s, 9H).

19-8

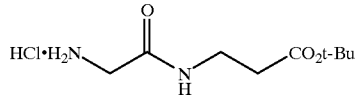

Glycyl-β-alanine t-butyl ester hydrochloride (19-8)

A solution of 19-7 (1.51 g, 4.49 mmol) in 40 mL EtOAc was treated with 10% Pd/C (0.30 g), and a $H_2$ balloon. After stirring overnight under a hydrogen atmosphere, an additional 200 mg of 10% Pd/C was added and hydrogenation was continued for 4 h before filtering through Celite and concentrating, providing the free amine as a colorless oil. The amine was dissolved in $Et_2O$ and an excess of 1 M HCl in $Et_2O$ was added. Concentration provided 19-8 as a waxy solid.

$^1$H NMR (free amine, 400 MHz, $d_6$-DMSO): δ8.31 (br s, 1H), 5.30 (br s, 2H), 3.29 (q, J=6 Hz, 2H), 3.25 (s, 2H), 2.38 (t, J=7 Hz, 2H), 1.41 (s, 9H).

19-9

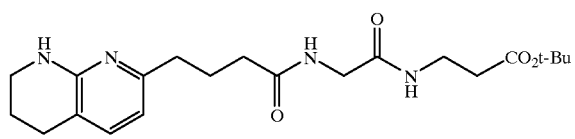

4-(1,2,3,4-Tetrahydro-1,8-naphthyridin-7-yl)butanoyl-glycyl-β-alanine t-butyl ester (19-9)

A mixture of 19-5 (62 mg, 0.24 mmol), 19-8 (69 mg, 0.29 mmol), NMM (130 μL, 1.2 mmol) and BOP (160 mg, 0.36 mmol) in 2 mL $CH_3CN$ was stirred overnight. After diluting with EtOAc the mixture was washed with sat. $NaHCO_3$, water (5×) and brine, dried ($MgSO_4$), filtered and concentrated, providing 19-9.

TLC $R_f$ 0.79 (silica, 25% $NH_3$-sat. EtOH/EtOAc)

$^1$H NMR (300 MHz, $CDCl_3$): δ8.50 (br t, 1H), 7.08 (d, J=7 Hz, 1H), 6.64 (br t, 1H), 6.33 (d, J=7 Hz, 1H), 5.69 (br s, 1H), 3.99 (d, J=7 Hz, 2H), 3.53 (q, J=6 Hz, 2H), 3.43 (m, 2H), 2.69 (t, J=6 Hz, 2H), 2.60 (t, J=7 Hz, 2H), 2.46 (t, J=6 Hz, 2H), 2.25 (t, J=7 Hz, 2H), 2.05–1.90 (m, 4H), 1.45 (s, 9H).

19-10

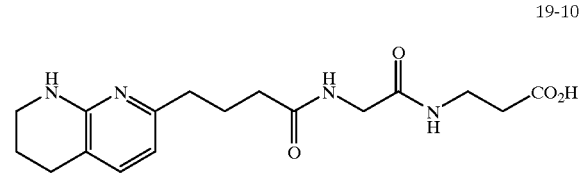

4-(1,2,3,4-Tetrahydro-1,8-naphthyridin-7-yl)butanoyl-glycyl-β-alanine (19-10)

Ester 19-9 (69 mg, 0.17 mmol) was dissolved in 1 mL $CH_2Cl_2$ at 0° C., 1 mL TFA was added, and the reaction was warmed to ambient temperature for 6 hr. After concentrating and azeotroping with toluene, flash chromatography (silica, 7:20:1:1 EtOAc/EtOH/$H_2O$/$NH_4OH$) provided 19-10 as a white solid.

TLC $R_f$ 0.38 (silica, 7:20:1:1 EtOAc/EtOH/$H_2O$/$NH_4OH$)

$^1$H NMR (400 MHz, $D_2O$): δ7.53 (d, J=7 Hz, 1H), 6.59 (d, J=7 Hz, 1H), 3.85 (s, 2H), 3.46 (t, J=6 Hz, 2H), 3.42 (t, J=7 Hz, 2H), 2.78 (t, J=6 Hz, 2H), 2.72 (t, J=8 Hz, 2H), 2.40 (apparent q, J=7 Hz, 4H), 2.00 (qn, J=6 Hz, 2H), 1.92 (qn, J=6 Hz, 2H).

-continued

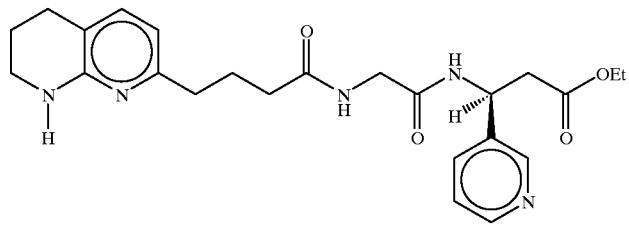

20-2

MeOH
1N NaOH

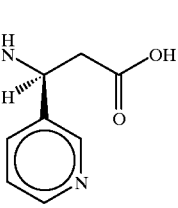

20-3

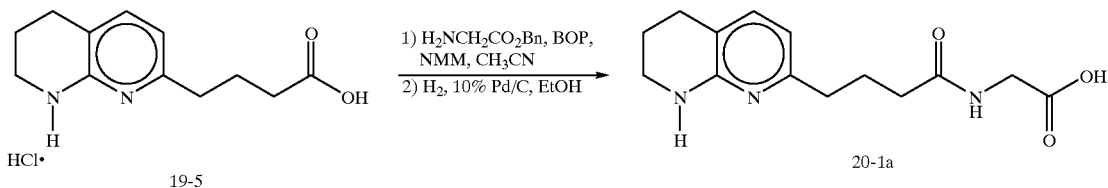

4-(1,2,3,4-Tetrahydro-1,8-naphthyridin-7-yl)butanoyl glycine (20-1a)

A mixture of 19-5 (1.02 g, 4.0 mmol), glycine benzyl ester (0.8 g, 4.0 mmol), NMM (1.76 ml, 16 mmol) and BOP (2.03 g, 4.6 mmol) in $CH_3CN$ (100 ml) was stirred overnight. The reaction was concentrated and the residue was partitioned between EtOAc and $H_2O$. The organic layer was washed with sat. $NaHCO_3$ solution, brine, dried ($MgSO_4$), filtered and concentrated to a yellow gum which was purified by flash chromatography (silica, 1:1, acetone/$CH_2Cl_2$) to provide the ester as a colorless gum.

A solution of the ester (1.3 g, 3.5 mmol) in EtOH (100 ml) was hydrogenated at 1 atm for 18 hr. The reaction was diluted with EtOAc (200 ml) to dissolve the product, filtered and concentrated to a solid which was sonicated with ether (100 ml) to provide 20-1a as a colorless solid.

TLC $R_f$ 0.35 (silica, EtOH/NH3)

$^1H$ NMR (300 MHz, $CD_3OD$): δ7.50 (d, J=7 Hz, 2H), 6.59 (d, J=7 Hz, 2H), 3.80 (s, 2H), 3.47 (t, J=6 Hz, 2H), 2.79 (t, J=6 Hz, 2H), 2.72 (t, J=7 Hz, 2H), 2.26 (t, J=7 Hz, 2H), 2.02 (m, 2H), 1.94 (m, 2H).

4-(1,2,3,4-Tetrahydro-1,8-naphthyridin-7-yl)butanoyl-glycyl-3(S)-pyhdin-3-yl-β-alanine ethyl ester (20-2)

The $CH_3CN$ solution (300 mL) of 20-1a (164 mg, 0.59 mmol), 20-1 (Rico et al., J. Org. Chem., 1993, 58, 7948) (158 mg, 0.58 mmol), NMM (260 μl, 2.36 mmol) and BOP (300 mg, 0.68 mmol) was stirred under ambient conditions for 48 h. The reaction was concentrated to a yellow gum which was purified by flash chromatography (silica, 9:1 $CH_2Cl_2$/EtOH. $NH_3$) to provide 20-2 as a colorless gum.

$R_f$ 0.21 (silica, 9:1 $CH_2Cl_2$/EtOH. $NH_3$)

$^1H$ NMR (300 MHz, $CD_3OD$): δ8.53 (bs, 1H), 8.42 (d, J=5 Hz, 1H), 7.82 (d, J=8 Hz, 1H), 7.39 (dd, J=8 Hz, 5 Hz, 1H), 7.10 (d, J=8 Hz, 1H), 6.36 (d, J=7 Hz, 1H), 5.40 (t, J=7 Hz, 1H), 4.07 (q, d=7 Hz, 2H), 3.85 (s, 2H), 3.36 (t, J=6 Hz, 2H), 2.91 (m, 2H), 2.68 (t, J=6 Hz, 2H), 2.51 (t, J=7 Hz, 2H), 2.23 (t, J=7 Hz, 2H), 1.89 (m, 4H), 1.16 (t, J=7 Hz, 3H).

4-(1,2,3,4-Tetrahydro-1,8-naphthyridin-7-yl)butanoyl-glycyl-3(S)-pyridin-3-yl-β-alanine (20-3)

A methanol solution (10 mL) of 20-2 (190 mg, 0.42 mmol) and 1N NaOH (2.1 mL, 2.1 mmol) was stirred under ambient conditions for 18 h. The reaction was concentrated to dryness and the residue neutralized with 1N HCl and the resultant solution concentrated to a gum which was chromatographed (silica, 38/1/1 EtOH/$NH_4OH$/$H_2O$) to provide a solid which was purified by HPLC using a VyOAC $C_{18}$ semi prep column with gradient elution [95:5(99.9:0.1 $H_2O$/TFA)/(99.9:0.1 $CH_3CN$/TFA)→50:50 (99.9:0.1 $H_2O$/TFA)/(99.9:0.1 $CH_3CN$/TFA)80 min] to provide 20-3 as a hygroscopic solid ditrifluoroacetate salt.

$R_f$ 0.36 (silica 38:1:1 EtOH/$NH_4OH$/$H_2O$)

$^1H$ NMR (300 MHz, $CD_3OD$): δ8.79 (bs, 1H), 8.65 (d, J=5 Hz, 1H), 8.7 (d, J=8 Hz, 1H), 7.84 (m, 1H), 7.57 (d, J=7 Hz, 1H), 6.61 (d, J=7 Hz, 1H), 5.44 (t, J=7 Hz, 4H), 3.88 (m, 2H), 3.48 (t, J=5 Hz, 2H), 2.98 (d, J=7 Hz, 2H), 2.81 (t, J=6 Hz, 2H), 2.70 (m, 2H), 2.31 (m, 2H), 1.96 (m, 4H).

SCHEME 21
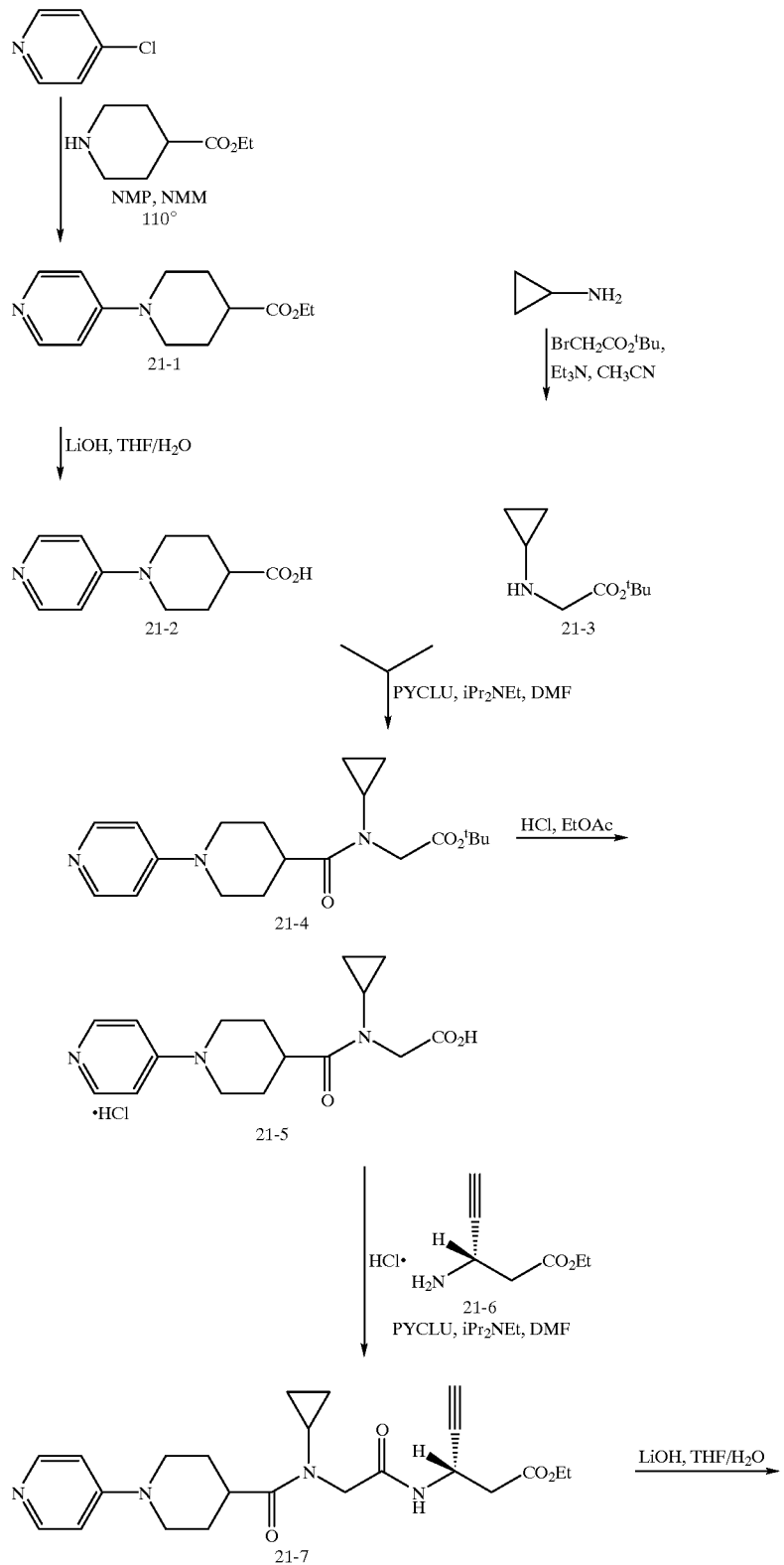

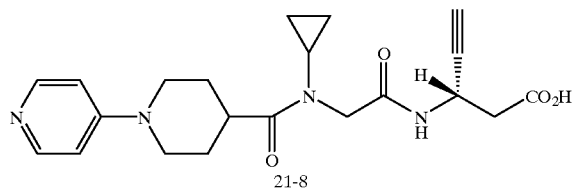

21-8

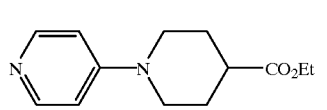

21-1

Ethyl N-pyridin-4-ylisonipecotate (21-1)

Ethyl isonipecotate (6.0 g, 38.66 mmol), 4-chloropyridine hydrochloride (5.9 g, 38.66 mmol) and N-methylmorpholine (9.3 mL, 85.0 mmol) were dissolved in N-methylpyrrolidinone (50 mL) and the resulting solution heated at 100° for 48 h. The solution was concentrated in vacuo and the residue dissolved in ethyl acetate (200 mL), washed with water and brine (2×100 mL), then dried ($Na_2SO_4$) and evaporated. The resulting residue was purified by flash chromatography (5%MeOH/$CH_2Cl_2$) to afford 21-1 as a crystalline solid.

$^1$H NMR (300 MHz, $CDCl_3$) δ8.21 (d, J=6.8 Hz, 2H), 6.78 (d, J=6.8 Hz, 2H), 4.18 (q, J=7.0 Hz, 2H), 3.85 (m, 2H), 3.10 (m, 2H), 2.61 (m, 1H) 2.05 (m, 2H), 1.85 (m, 2H), 1.23 (t, J=7.0 Hz, 3H).

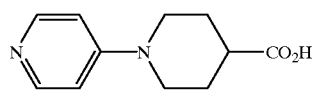

21-2

N-Pyridin-4-ylisonipecotic acid (21-2)

A solution of ester 21-1 (10 g, 42.7 mmol) in THF (50 mL) was treated with 1N LiOH (47 mL, 47.0 mmol) and $H_2O$ (50 mL). The resulting solution was concentrated and the aqueous residue cooled to 0° C., then adjusted to pH≈6 with 1N HCl and the resulting solid 21-2, collected by filtration.

$^1$H NMR (300 MHz, $D_2O$) δ7.95 (d, 6.8 Hz, 2H), 6.73 (d, 6.8 Hz, 2H), 3.76 (d, J=12.8 Hz, 2H), 2.81 (m, 2H), 2.20 (m, 1H), 1.85 (d, J=12.8 Hz, 2H), 1.55 (m, 2H).

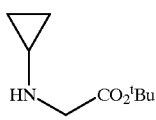

21-3 tert-Butyl-N-cyclopropylglycine (21-3)

A mixture of cyclopropylamine (10.0 g, 175.1 mmol) and triethylamine (4.9 ml, 35.5 mmol) in 100 ml $CH_2Cl_2$ was cooled to 0° C. and treated with tert-butyl bromoacetate (5.25 ml, 35.0 mmol). The resulting mixture was stirred at 0° C. for 2 h, refluxed for 1.5 h, then cooled and washed with sat. $NaHCO_3$, and brine (50 ml each) then dried ($Na_2SO_4$) and evaporated to afford 21-3 a colorless oil.

$^1$H NMR (300 MHz, $CDCl_3$) δ3.35 (s, 2H), 2.19 (m, 1H), 2.08 (br s, 1H), 1.48 (s, 9H), 0.47 (m, 2H), 0.38 (m, 2H).

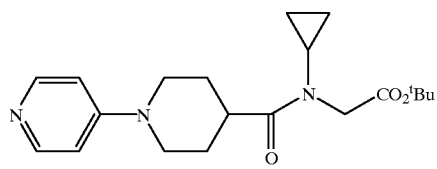

21-4 tert-Butyl N-pyridin-4-ylisonipecotyl-N-cyclopropylglucine (21-4)

A solution of acid 21-2 (500 mg, 2.36 mmol), ester 21-4 (404 mg, 2.36 mmol), chloro-N,N,N',N'-bis (pentamethylene)-formamidirnum hexafluorophosphate (PYCLU) (851 mg, 2.36 mmol), and diisopropylethyl amine (305 mg, 2.36 mmol) in anhydrous DMF (50 mL) was stirred at room temperature for 18 h then concentrated in vacuo to afford a yellow residue. Chromatography on silica gel (1:1 MeOH/EtOAc) afforded 21-4 as a crystalline solid.

$^1$H NMR (300 MHz, $CD_3OD$) δ8.12 (d, J=6.8 Hz, 2H), 6.75 (d, J=6.8 Hz, 2H), 3.94 (d, J=12.8 Hz, 2H), 3.85 (s, 2H), 2.81 (m, 2H), 1.95 (m, 2H), 1.85 (m, 2H), 1.55 (m, 2H), 1.42 (s, 9H), 0.47 (m, 2H), 0.38 (m, 2H).

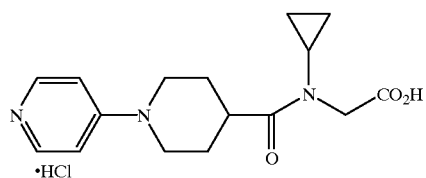

21-5

N-Pyridin-4-ylisonipecotyl-N-cyclooropylylycyl (21-5)

Ester 21-5 (250 mg, 0.70 mmol) was suspended in EtOAc (25 mL), cooled to 0° and treated with HCl gas for 15 min. The resulting solution was stirred at 0° for 3.5 h then evaporated to give 21-5 as a yellow glass.

$^1$H NMR (300 MHz, $CD_3OD$) δ8.18 (d, J=6.8 Hz, 2H), 7.18 (d, J=6.8 Hz, 2H), 4.24 (d, J=12.8 Hz, 2H), 3.95 (s, 2H), 3.21 (m, 2H), 1.95 (m, 2H), 1.85 (m, 2H), 1.62 (m, 2H), 0.87 (m, 2H), 0.75 (m, 2H).

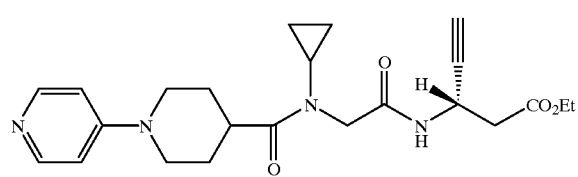

21-7

Ethyl N-pyridin-4-ylisonipecotyl-N-cyclopropylglycyl-3(S)-ethynyl-β-alanine (21-7)

A solution of acid 21-5 (232 mg, 0.68 mmol), ester 21-6 (121 mg, 0.68 mmol) (21-6 prepared as described in U.S. Pat. No. 5,272,162), PYCLU (245 mg, 0.68 mmol), and diisopropylethyl amine (176 mg, 0.68 mmol) in anhydrous DMF (50 ml) was stirred at room temperature for 18 h then concentrated in vacuo to afford a yellow residue. Preparative reverse phase chromatographic purification afforded ester 21-7 as its TFA salt.

$^1$H NMR (300 MHz, CD$_3$OD) δ8.48 (d, J=6.8 Hz, 1H), 8.08 (d, J=6.8 Hz, 2H), 7.18 (d, J=6.8 Hz, 2H), 5.01 (m, H), 4.24 (d, J=12.8 Hz, 2H), 4.12 (q, J=7 Hz, 2H), 3.99 (s, 2H), 3.72 (m, 1H), 3.31 (m, 2H), 2.95 (m, 1H), 2.73 (m, 2H), 1.95 (m, 2H), 1.85 (m, 2H), 1.21 (t, J=7.0 Hz, 2H), 0.87 (m, 2H), 0.75 (m, 2H).

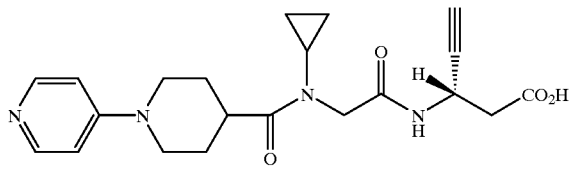

21-8

N-Pyridin-4-ylisonipecotyl-N-cyclopropylglycyl -3(S)-ethynyl-β-alanine (21-8)

A solution of ester 21-7 (180 mg, 0.422 mmol), in THF (10 mL) was treated with 1N LiOH (0.84 mL, 0.84 mmol) and stirred at room temperature for 16 h. The mixture was concentrated and the residue purified by preparative reverse, phase chromatography to afford 19-8 as its TFA salt.

$^1$H NMR (300 MHz, CD$_3$OD) δ8.40 (d, J=6.8 Hz, 1H), 8.21 (d, J=6.8 Hz, 2H), 7.21 (d, J=6.8 Hz, 2H), 4.81 (m, 1H), 4.22 (d, J=12.8 Hz, 2H), 3.99 (m, 2H), 3.72 (m, 1H), 3.31 (m, 2H), 2.95 (m, 1H), 2.76 (m, 1H), 2.71 (m, 2H), 1.95 (m, 2H), 1.85 (m, 2H), 0.87 (m, 2H), 0.75 (m, 2H).

SCHEME 22

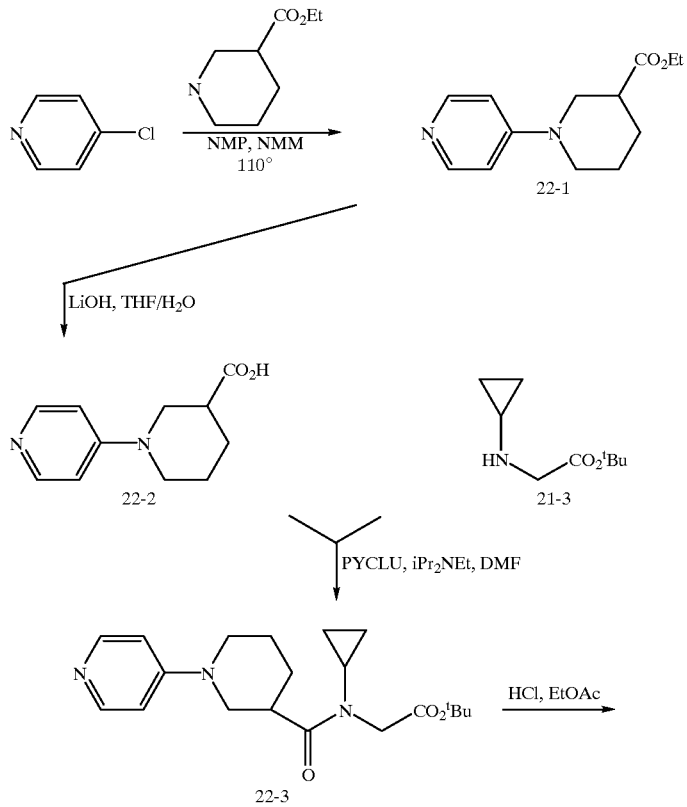

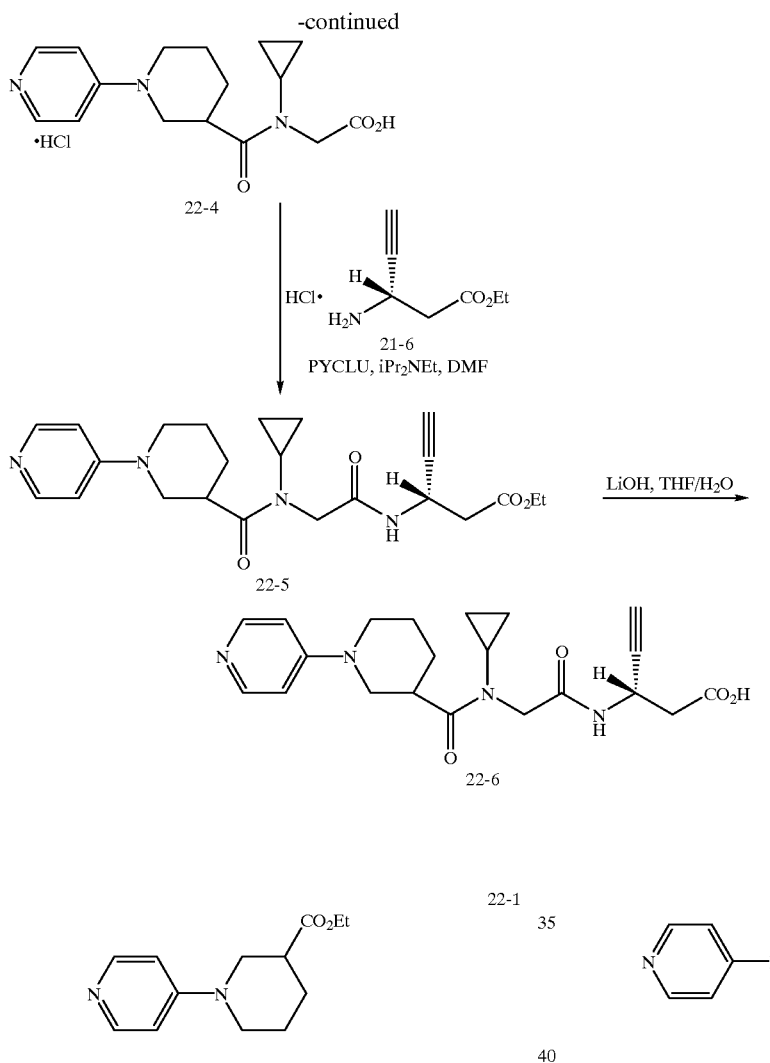

Ethyl N-pyridin-4-ylnipecotate (22-1)

Ethyl (+) nipecotate (7.0 g, 44.53 mmol) was reacted with 4-chlorpyridine hydrochloride (6.67 g, 44.53 mmol) as described for 21-1 to give the title compound as a yellow solid.

$^1$H NMR (300 MHz, CDCl$_3$) δ8.22 (d, J=6.8 Hz, 2H), 6.68 (d, J=6.8 Hz, 2H), 4.18 (q, J=7.0 Hz, 2H), 3.85 (m, 1H), 3.72 (m, 1H), 3.21 (m, 1H), 3.10 (m, 1H), 2.60 (m, 1H), 2.08 (m, 1H), 1.81 (m, 2H), 1.60 (m, 1H), 1.13 (t, J=7.0 Hz, 3H).

N-Pyridin-4-ylnipecotic acid (22-2)

Prepared from 22-1 (764 mg, 3.25 mmol) in a manner similar to that described for 21-2.

$^1$H NMR (300 MHz, DMSO-d$_6$) δ8.13 (d, J=6.8 Hz, 2H), 6.74 (d, J=6.8 Hz, 2H), 4.08 (d, 1H), 3.78 (m, 1H), 2.92 (m, 2H), 2.10 (m, 1H), 1.95 (m, 1H), 1.71 (m, 1H), 1.42 (m, 2H).

tert-Butyl N-pyridin-4-ylnipecotyl-N-cyclopropyllycine (22-3)

Prepared from 22-2 (320 mg, 1.51 mmol) and 21-3 (258 mg, 1.51 mmol) in a manner similar to that described for 21-4.

$^1$H NMR (300 MHz, CDCl$_3$) δ8.12 (d, 6.8 Hz, 2H), 6.62 (d, J=6.8 Hz, 2H), 3.94 (s, 2H), 3.85 (m, 1H), 3.12 (m, 1H), 3.08 (m, 1H), 2.51 (m, 2H), 1.95 (m, 1H), 1.85 (m, 2H), 1.58 (m, 2H), 1.42 (s, 9H), 0.47 (m, 2H), 0.38 (m, 2H).

N-Pyridin-4-ylnipecotyl-N-cyclopropylglycine hydrochloride (22-4)

Ester 22-3 (250 mg, 0.70 mmol) was suspended in EtOAc (25 mL), cooled to 0° and treated with HCl gas for 15 min. The resulting solution was stirred for 3.5 h then evaporated to give 22-4 as a white solid.

$^1$H NMR (300 MHz, DMSO-d$_6$) δ8.18 (d, J=6.8 Hz; 2H), 7.18 (d, J=6.8 Hz, 2H), 4.24 (d, J=12.8 Hz, 2H), 3.95 (m,

2H), 3.21 (m, 1H), 1.94 (m, 1H), 1.85 (m, 1H), 1.72 (m, 1H), 1.53 (m, 1H), 0.87 (m, 2H), 0.75 (m, 2H).

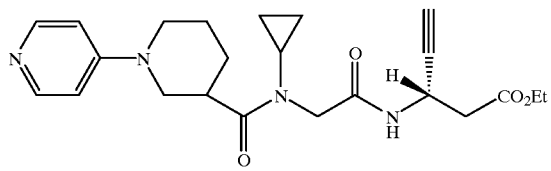

22-5

Ethyl N-pyridin-4-ylnipecotyl-N-cyclopropylglycyl-3(S)-ethynyl-β-alanine (22-5)

Prepared from 22-4 (195 mg, 0.60 mmol) in a manner similar to that described for 21-7.

¹H NMR (300 MHz, CD₃OD) δ8.49 (d, J=6.8 Hz, 1H), 8.17 (d, J=6.8 Hz, 2H), 7.21 (d, J=6.8 Hz, 2H), 5.15 (m, 1H), 4.26 (m, 1H), 4.21 (d, 1H), 4.08 (q, 2H), 3.82 (m, 1H), 3.5–3.3 (m, 3H), 2.95 (m, 1H), 2.76 (m, 1H), 2.71 (m, 2H), 2.15 (m, 1H), 1.95 (m, 1H), 1.81 (m, 1H), 1.72 (m, 1H), 1.21 (t, 3H), 0.87 (m, 2H).

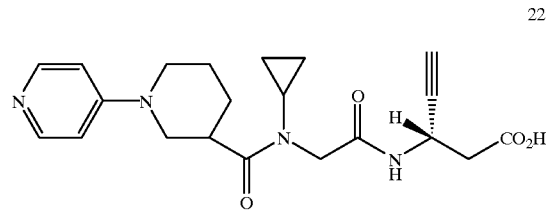

22-6

N-Pyzidin-4-ylnipecotyl-N-cyclopropylglycyl-3(S)-ethynyl-β-alanine (22-6)

Prepared from 22-4 (20 mg, 0.04 mmol) in a manner similar to that described for 21-8.

FAB mass spectrumi n/z=399 (M+1).

¹H NMR (300 MHz, CD₃OD) δ8.16 (d, J=6 Hz, 2H), 6.91 (d, J=6.8 Hz, 2H), 5.05 (m, 1H), 4.26 (d, Hz, 1H), 4.21 (d, 1H), 3.82 (m, 1h), 3.5–3.3 (m, 3H), 2.95 (m, 1H), 2.76 (m, 1H), 2.71 (m, 2H), 2.15 (m, 1H), 1.95 (m, 1H), 1.81 (m, 1H), 1.72 (m, 1H), 1.21 (t, 1H), 0.87 (m, 2H).

SCHEME 23

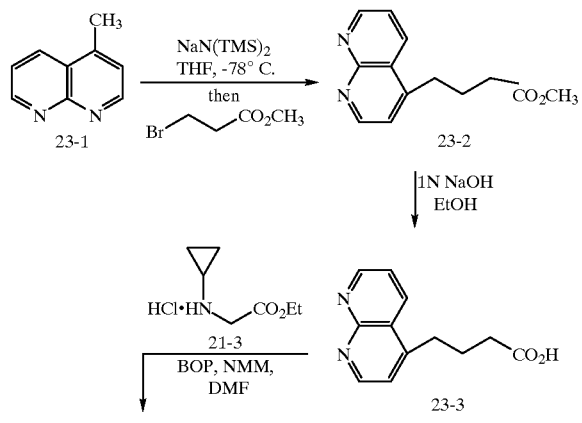

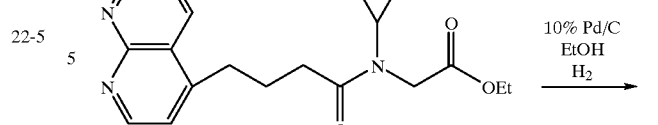

23-4

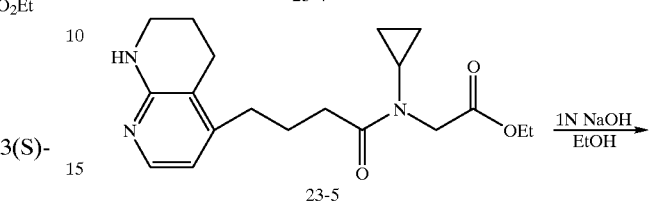

23-5

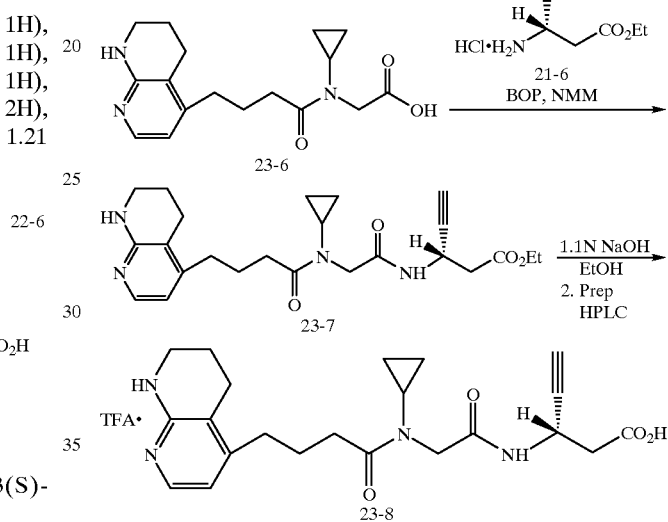

23-2

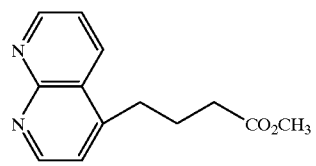

Methyl 4-(1,8-naphthyridin-4-yl)butyrate (23-2)

To a stirred solution of naphthyridine 23-1 (Hamada, Y. et al., *Chem. Pharm. Bull. Soc.*, 1971, 19(9), 1857–1862), (2.2 g, 15.2 mmol) and THF (200 ml) at −78° C. was added NaN(TMS)₂ (1M/THF, 18 ml, 18 mmol) dropwise over a 20 min period. After 30 minutes at −78° C., methyl 3-bromopropionate was added in a stream. After 30 min, the reaction was quenched with 50 ml 10% KHSO₄. The mixture was extracted with Et₂O. The remaining aqueous portion was basified with sat. NaHCO₃ and then extracted with EtOAc. The EtOAc portion was washed with brine, dried (MgSO₄) and concentrated. Flash chromatography (silica, 2% EtOH/EtOAc) gave the ester 23-2 (1.61 g) as a yellow oil.

TLC R$_f$=0.27 (silica, 2% EtOH/EtOAc)

¹H NMR (400 MHz, CDCl₃) δ9.14 (m, 1H), 9.35 (d, J=4 Hz, 1H), 8.50 (d, J=7 Hz, 1H), 7.52 (q, J=4 Hz, 1H), 7.33 (d, J=4 Hz, 1H), 3.71 (s, 3H), 3.14 (t, J=8 Hz, 2H), 2.46 (t, J=7 Hz, 2H), 2.09 (m, 2H).

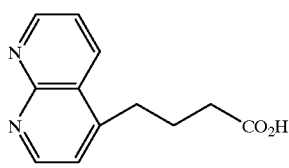

23-3

4-(1,8-Naphthyridin-4-yl)butanoic acid (1-3)

A solution of ester 23-2 (1.60 g, 6.9 mmol), 1N NaOH (7 ml, 7 mmol) and EtOH (20 ml) was stirred at ambient temperature for 1.0 h. The solution was extracted with $Et_2O$. The aqueous portion was neutralized with concentrated HCl (583 gl, 7.0 mmol). The precipitate was collected, washed with $Et_2O$, and dried in vacuo to furnish carboxylic acid 23-3 as a tan solid.

TLC $R_f$=0.59 (silica, 20:1:1 $CH_2Cl_2$/MeOH/AcOH)

$^1$H NMR (400 MHz, $CD_3OD$) δ9.05 (q, J=2H, 1H), 8.95 (d, J=4H, 1H), 8.77 dd, J=2 Hz, 8 Hz, 1H), 7.67 (q, J=4H, 1H), 7.53 (d, J=4 Hz, 1H), 3.22 (t, J=8 Hz, 2H), 2.46 (t, J=7 Hz, 2H), 2.03 (m, 2H).

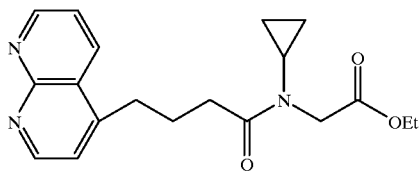

23-4

4-(1,8-Naphthyridin-4-yl)butanoyl-N-(cyclopropyl)glycine ethyl ester (23-4)

A solution of acid 23-3 (400 mg, 1.84 mmol), amine 21-3 (331 mg, 1.84 mmol), BOP reagent (979 mg, 2.21 mmol), NMM (1.03 ml, 7.36 mmol) and DMF (20 ml) was stirred at ambient temperature for 20 h. The solution was diluted with ethyl acetate and then washed with sat. $NaHCO_3$, brine, dried ($MgSO_4$) and concentrated. Flash chromatography (silica, 10:1 EtOAc/sat. $NH_3$-EtOH) furnished ester 23-4 (600 mg) as an orange solid.

TLC $R_f$=0.15 (silica, 10:1 EtOAc/sat. $NH_3$-EtOH)

$^1$H NMR (300 MHz, $CDCl_3$) δ9.12 (m, 1H), 9.03 (d, J=4 Hz, 1H), 8.62 (dd, J=2 Hz, 8 Hz, 1H), 7.53 (q, J=4 Hz, 1H), 7.38 (d, J=4 Hz, 1H), 4.20 (q, J=7 Hz, 2H), 4.13 (s, 2H), 3.19 (t, J=8 Hz, 2H), 2.79 (m, 1H), 2.70 (m, 2H), 2.13 (m, 2H), 1.29 (t, J=8 Hz, 3H), 0.85 (m, 2H), 0.74 (m, 2H).

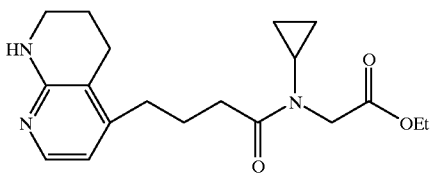

23-5

4-(1,2,3,4-Tetrahydro-1,8-naphthyridin-5-yl)butanoyl-N-(cyclo-propyl)glycine ethyl ester (23-5)

A mixture of ester 23-4 (600 mg, 1.75 mmol), 10% Pd/C (300 mg) and EtOH (30 ml) was stirred under hydrogen atmosphere (1 atm) at ambient temperature for 20 h. The catalyst was removed by filtration through celite and then the filtrate was concentrated. Flash chromatography (silica, 50%/EtOAc/sat. $NH_3$-EtOH) gave ester 23-5 as a colorless oil.

TLC $R_f$=0.25 (silica, 50:1 EtOAc/sat. $NH_3$-EtOH)

$^1$H NMR (400 MHz, $CD_3OD$) δ7.58 (d, J=6 Hz, 1H), 6.48 (d, J=6 Hz, 1H), 4.15 (q, J=7 Hz, 2H), 4.08 (s, 2H), 3.36 (t, J=5 Hz, 2H), 2.86 (m, 1H), 2.75 (t, J=6 Hz, 2H), 2.68 (t, J=7 Hz, 2H), 2.60 (t, J=8 Hz, 2H), 1.90 (m, 4H), 1.2 (t, J=7 Hz, 3H), 0.87 (m, 2H), 0.78 (m, 2H).

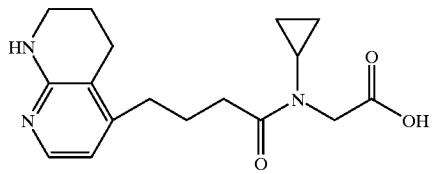

23-6

4-(1,2,3,4-Tetrahydro-1,8-napthyridin-5-yl)butanoyl-N-(cyclo-propyl)glycine (23-6)

A solution of ester 23-5 (200 mg, 0.5774 mmole), 1N NaOH (600 μl, 0.600 mmole) and $CH_3OH$ was stirred at ambient temperature for 1.5 h. The solution was concentrated. The residue was dissolved in 1N HCl (600 μl) and then the solution was concentrated. The residue was dissolved in $CHCl_3$, filtered and concentrated to give the carboxylic acid 23-6 (110 mg) as a white solid.

TLC $R_f$=0.14 (silica, 10:1:1 $CH_2Cl_2$/MeOH/AcOH)

$^1$H NMR (300 MHz, $CD_3OD$) δ7.56 (d, J=6 Hz, 1H), 6.64 (d, J=6 Hz, 1H), 3.98 (s, 2H), 3.41 (t, J=6 Hz, 2H), 2.89 (m, 1H), 2.81 (t, J=6 Hz, 2H), 2.71 (m, 4H), 1.88 (m, 4H), 0.82 (m, 4H).

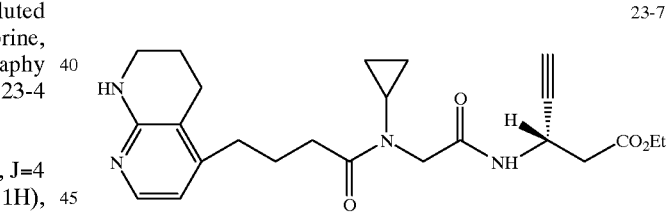

23-7

4-(1,2,3,4-Tetrahydro-1,8-naphthyridin-5-yl)butanoyl-N-(cyclo-propyl)glycyl-3(S)-ethynyl-β-alanine ethyl ester (23-7)

To a stirred solution of acid 23-6 (40 mg, 0.1256 mmol), amine 21-6 (33 mg, 0.1884 mmol), NMM (70 μl, 0.5024 mmol) and $CH_3CN$ (1 ml) was added BOP reagent (61 mg, 0.1382 mmol). After 20 h at ambient temperature, the solution was diluted with ethyl acetate and then washed with sat. $NaHCO_3$, brine, dried ($MgSO_4$) and concentrated. Flash chromatography (silica, 40:1:1 $CH_2Cl_2$/MeOH/AcOH) gave the ester 23-7 as a colorless oil.

TLC $R_f$=0.23 (silica, 40:1:1 $CH_2Cl_2$/MeOH/AcOH)

$^1$H NMR (300 MHz, $CD_3OD$) δ7.58 (d, J=6 Hz, 1H), 6.66 (d, J=6 Hz, 1H), 5.01 (m, 1H), 4.13 (q, J=7Hz, 2H), 4.02 (s, 2H), 3.42 (t, J=6 Hz, 2H), 2.72 (m, 10H), 1.95 (m, 4H), 1.24 (t, J=7 Hz, 3H), 0.85 (m, 2H), 0.78 (m, 2H).

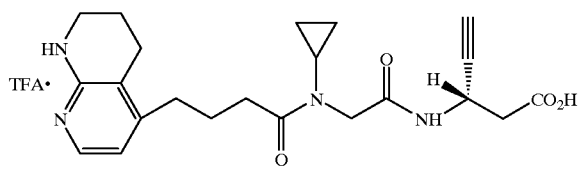

4-(1,2,3,4-Tetrahydro-1,8-naphthyridin-5-yl)butanoyl-N-(cyclo-prodyl)glycyl-3(S)-ethynyl-β-alanine (23-8)

A solution of ester 23-7 (32 mg, 0.0725 mmol), 1N NaOH (100 μl) and CH$_3$OH (500 ml) was stirred at ambient temperature for 1.0 h. The solution was concentrated. The residue was dissolved in 1N HCl (100 μl) and then concentrated. Preparative HPLC purification (C$_{18}$, H$_2$O/CH$_3$CN/TFA) provided acid 23-8 as a TFA salt.

TLC R$_f$=0.50 (silica, 10:1:1 EtOH/NH$_4$OH/H$_2$O)

$^1$H NMR (300 MHz, CD$_3$OD) δ8.43 (d, J=9 Hz, 1H), 7.58 (d, J=7 Hz, 1H), 6.76 (d, J=7 Hz, 1H), 4.99 (m, 1H), 4.03 (d, J=3 Hz, 2H), 3.46 (t, J=5 Hz, 2H), 2.72 (m, 10H), 1.95 (m, 4H), 0.87 (m, 2H), 0.79 (m, 2H).

SCHEME 24

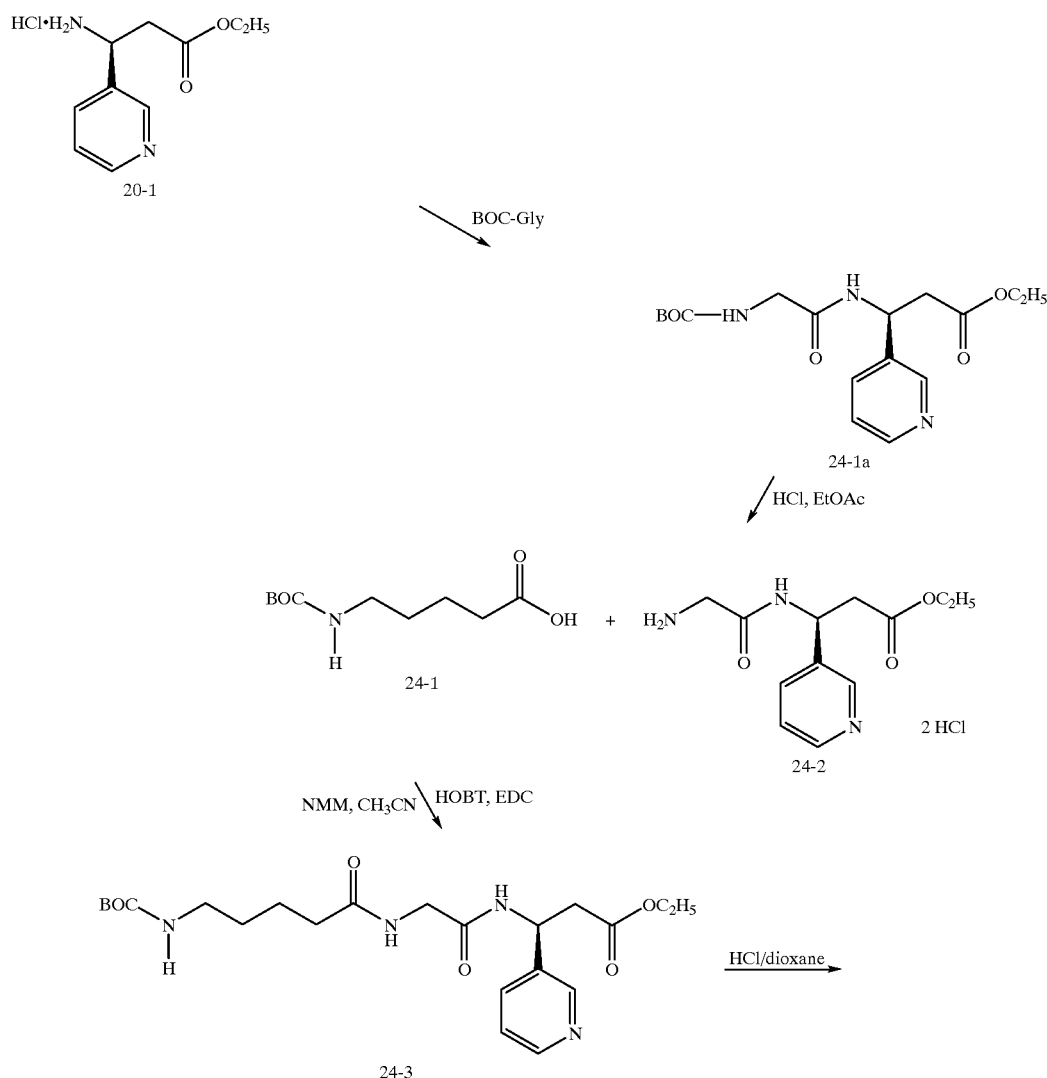

-continued
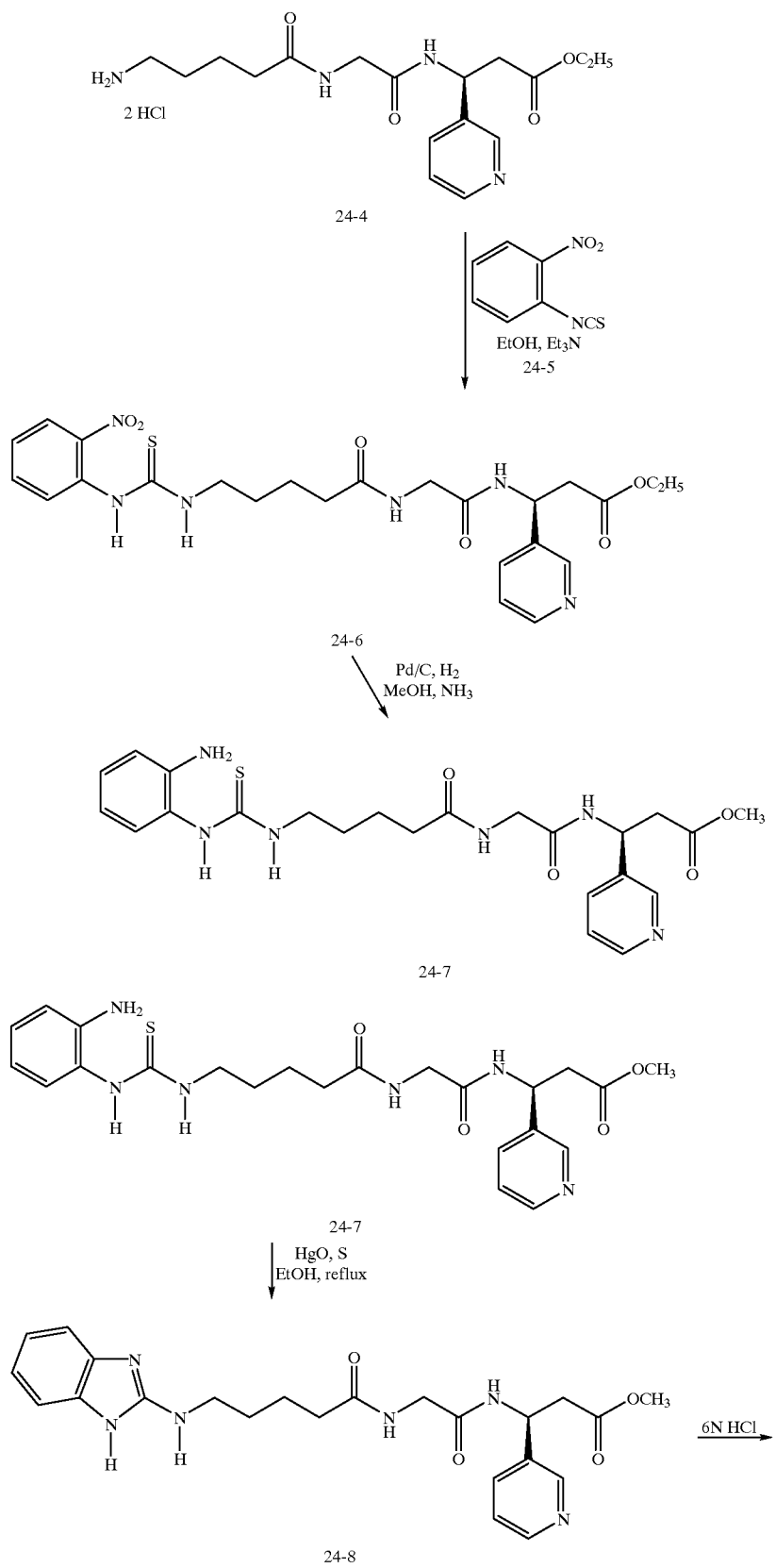

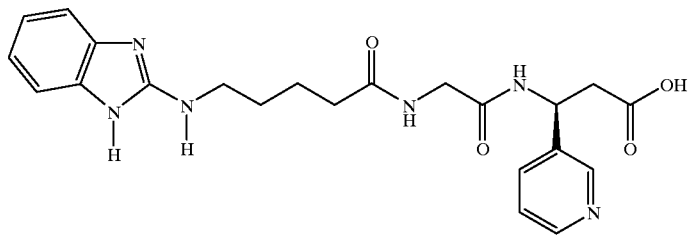

24-9

Preparation of 3-{2-[5-(1H-Benzoimidazol-2-yl-amino)-pentanoyl-amino]-acetylamino}-3(S)-pyridin-3-yl-propionic acid (24-9)

3-t-Butoxycarbonylaminoacetylamino-3(S)-pyridin-3-yl-propionic acid ethyl ester bis hydrochloride (24-1a)

A stirred solution of BOC—Gly (645 mg, 3.7 mmol), NMM (452 uL, 4.0 mmol), and EtOAc (35 mL) at 0° C. was treated with isobutyl chloroformate (534 uL, 4.0 mmol). After 20 min 20-1 (1.0 g, 3.7 mmol) and NMM (1.2 mL, 11 mmol) were added followed by removal of the cooling bath. After 20 hr, the reaction mixture was washed with $H_2O$, sat. $NaHCO_3$, and brine, dried ($MgSO_4$), and concentrated. Flash chromatography (silica, EtOAc to 5% MeOH/EtOAc) gave 24-1 as a colorless oil.

TLC: $R_f$=0.31 (20% MeOH/EtOAc), $^1$H NMR (300 MHz, CDCL3) δ8.58 (bs, 1H), 8.51(m, 1H), 7.62 (m, 1H), 7.49 (m, 1H), 5.48 (m, 1H), 4.13 (m, 1H), 4.08 (q, J=7 Hz, 2H), 3.83 (m, 2H), 2.90 (m, 2H), 1.43 (s, 9H), 1.13 (t, J=7 Hz, 3H).

3-Aminoacetylamino-3(S)-pyridin-3-yl-propionic acid ethyl ester bis-hydrochloride (24-2)

HCl gas was passed through a solution of 24-1a (0.84 g, 2.4 mmol) in EtOAc (24 mL) at 0° C. for 15 min and the reaction mixture stirred for an additional 15 min. The reaction mixture was concentrated and the residue triturated with ether to give 22 as a white solid.

TLC: $R_f$=0.29 (10:1:1 ethanol/$H_2O$/$NH_4OH$).

3-[2-(5-t-Butoxycarbonylaminopentanoylamino) acetylamino]-3(S)-pyridin-3-yl-propionic acid ethyl ester (24-3)

A $CH_3CN$ solution (20 mL) of 24-1 (71.7 mg, 0.33 mmol), 24-2 (97 mg, 0.30 mmol), HOBT (50.5 mg, 0.33 mmol), EDC (63.3 mg, 0.33 mmol) and NMM (132 ml, 1.2 mmol) was stirred under ambient conditions for 18 hr. The reaction solution was concentrated to a yellow gum which was partitioned between EtOAc and sat. $NaCO_3$ solution. The EtOAc layer was washed with $H_2O$, brine, dried ($MgSO_4$) and concentrated to provide 24-3 as a colorless gum.

TLC: $R_f$=0.41 (50% $CH_2Cl_2$/acetone), $^1$H NMR (300 MHz, $CDCL_3$) δ8.56(bs, 1H), 8.51(m, 1H), 7.62(m, 1H), 7.49(m, 1H), 5.43(m, 1H), 4.08(q, J=7 Hz, 2H), 3.94(m, 2H), 3.12(m, 2H), 2.90(m, 2H), 2.28(m, 2H), 1.64(m, 4H), 1.43(s, 9H), 1.13(t, J=7 Hz, 3H).

3-[2-(5-Aminopentanoylamino)-acetylamino]-3(S)-pyridin-3-yl-propionic acid ethyl ester dihydrochloride (24-4)

A 4M HCl/dioxane solution(10 mL) of 2 (101 mg, 0.24 mmol) was stirred under ambient conditions for 18 hr. The solution was concentrated to provide 24-4 as a pale yellow gum which was used in the next step without further purification.

$^1$H NMR (300 MHz, $CD_3OD$) δ8.93(bs, 1H), 8.79(m, 1H), 8.69(m, 1H), 8.10(m, 1H), 5.48(m, 1H), 4.14(q, J=7 Hz, 2H), 3.88(m, 2H), 3.07(m, 2H), 2.89(m, 2H), 2.33(m, 2H), 1.68(m, 4H), 1.23(t, J=7 Hz, 3H).

3-(2-{5-[3-(2-Nitrophenyl)-thioureido]-pentanoylamino}-acetylamino)-3(S)-pyridin-3-yl-propionic acid ethyl ester (24-6)

An ethanol solution (20 mL) of 24-5 (40 mg, 0.224 mmol) and 24-4 (95 mg, 0.224 mmol) was refluxed for 2 hr and concentrated to a yellow gum which was purified by flash chromatography (80% EtOAc/EtOH—$NH_3$) to provide 24-6 as a yellow gum.

TLC: $R_f$=0.41 (80% EtOAc/EtOH-$NH_3$), $^1$H NMR (300 MHz, $CD_3OD$) δ8.54(m, 1H), 8.42(m, 1H), 8.03(m, 2H), 7.83(m, 1H), 7.63(m, 1H), 7.41(m, 1H), 7.32 (m, 1H), 5.39(m, 1H), 4.09(q, J=7 Hz, 2H), 3.86(s, 2H), 3.61(m, 2H), 2.91(m, 2H), 2.33(m, 2H), 1.69(m, 4H), 1.16(t, J=7 Hz, 3H).

3-(2-{5-[3-(2-Aminophenyl)-thioureido]-pentanoylamino}-acetylamino)-3(S)-pyridin-3-yl-propionic acid methyl ester (24-7)

10% Pd/C (50 mg) and 24-6 (103 mg, 0.194 mmol) were added to methanol saturated with ammonia and the mixture hydrogenated at 1 atm. for 18 hr. The reaction was filtered and concentrated to provide 24-7 as a pale yellow gum which was used in the next step without further purification.

$^1$H NMR (300 MHz, $CD_3OD$) 5 8.53(m, 1H), 8.41(m, 1H), 7.84(m, 1H), 7.40(m, 1H), 7.07(m, 1H), 6.97(m, 1H), 6.82(m, 1H), 6.67(m, 1H), 5.38(m, 1H), 3.85(m, 2H), 3.62(s, 3H), 3.54(m, 2H), 2.93(m, 2H), 2.30(m, 2H), 1.60(m, 4H).

3-{2-[5-(1H-Benzoimidazol-2-yl-amino)-pentanoylamino]-acetyl-amino}-3(S)-pyridin-3-yl-propionic acid methyl ester (24-8)

An ethanol mixture (20 ml) of 24-7 (89 mg, 0.18 mmol), mercuric oxide (78.8 mg, 0.36 mmol) and sulfur (1.8 mg, 0.056 mmol) was refluxed for 2 hr. After cooling, the mixture was filtered and the filtrate concentrated to a semi-solid which was purified by flash chromatography (20% MeOH/$CH_2Cl_2$) to provide 24-8 as a solid.

TLC: $R_f$=0.13 (20% MeOH/$CH_2Cl_2$), $^1$H NMR (300 MHz, $CD_3OD$) δ8.52(m, 1H), 8.41(m, 1H), 7.81(m, 1H), 7.38(M, 1H), 7.23(m, 2H), 7.06(m, 2H), 5.38 (m, 1H), 3.85(s, 2H), 3.62(s, 3H), 3.37(m, 2H), 2.95(m, 2H), 2.33(m, 2H), 1.71(m, 4H).

3-{2-[5-(1H-Benzoimidazol-2-yl-amino)-pentanoylamino]-acetyl-amino}-3(S)-pyridin-3-yl-propionic acid (24-9)

A 6N HCl solution (5 ml) of 24-8 (33 mg, 0.073 mmol) was stirred under ambient conditions for 18 hr. The reaction was concentrated to give a viscous gum which was purified by prep HPLC (Delta-Pak $C_{18}$, gradient elution over 40 min., 5–50% $CH_3CN$/$H_2O$-0.1% TFA) to give 24-9.

$^1$H NMR (300 MHz, $CD_3OD$) δ8.78(m, 1H), 8.65(m, 1H), 8.40(m, 1H), 7.86(m, 1H), 7.34(m, 2H), 7.27(m, 2H), 5.40 (m, 1H), 3.87(m, 2H), 3.42(m, 2H), 2.98(m, 2H), 2.34(M, 2H), 1.74(m, 4H).

SCHEME 25
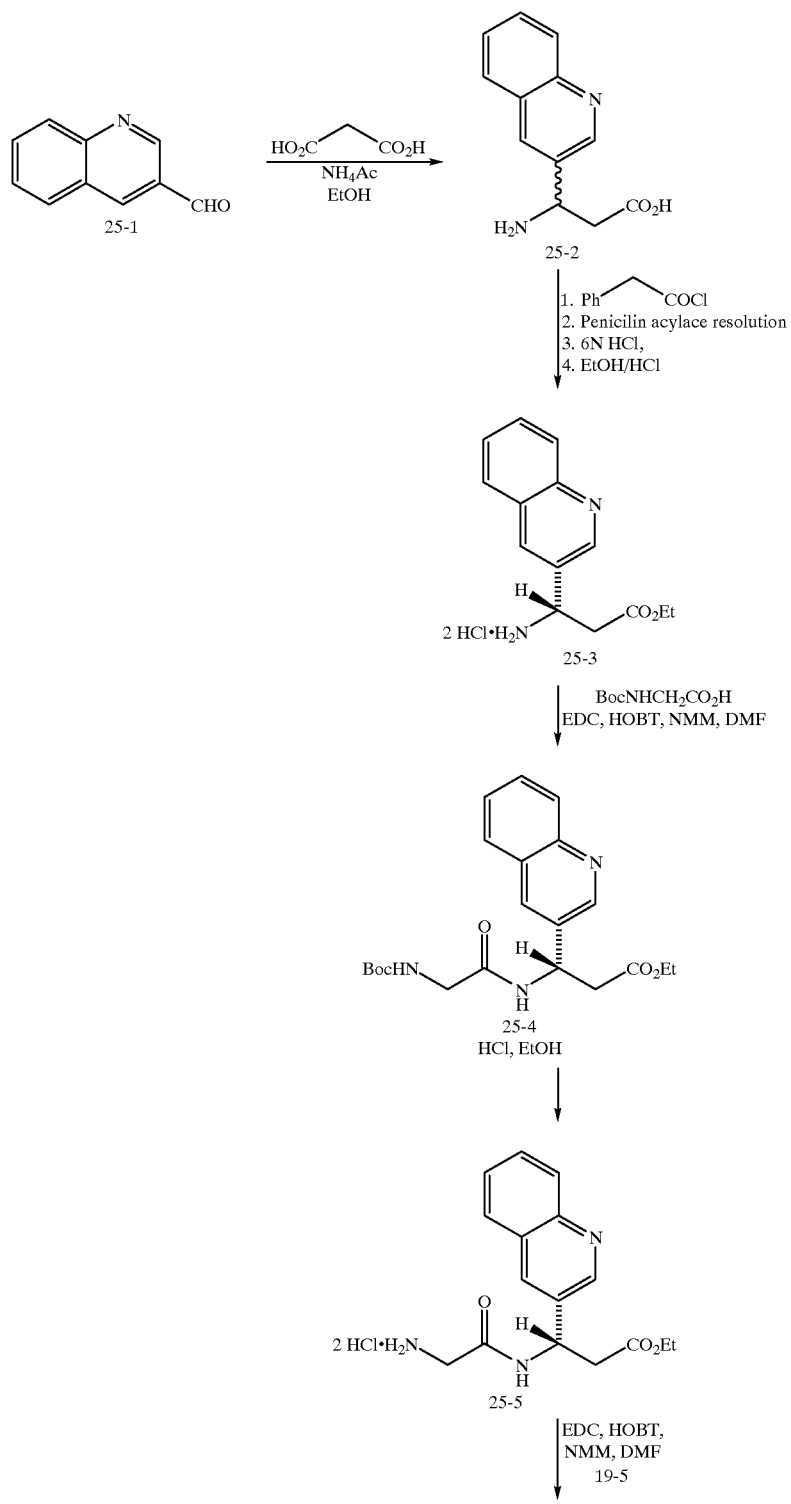

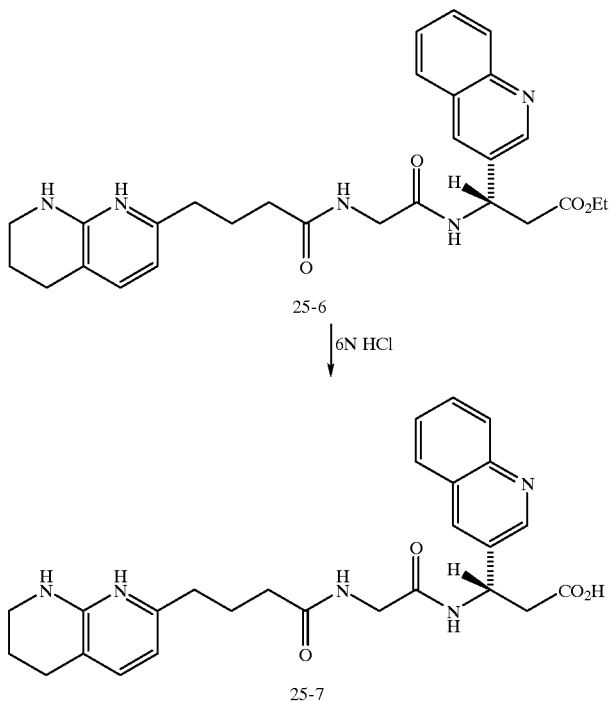

3(S)-Quinolin-3-yl-β-alanine ethyl ester hydrochloride (25-3)

A solution containing 25-1 3-carboxaldehyde (5 g, 31.8 mmol), malonic acid (3.6 g, 35.0 mmol), and ammonium acetate (5.0 g, 63.6 mmol) in anhydrous ethanol (125 mL) was heated at reflux for 12 h. After cooling to room temperature, the resulting white solid was collected by filtration and washed with cold ethanol (50 mL) and then dried under vacuum to provide 25-2 as a white solid.

$^1$H NMR (300 MHz, D$_2$O): δ8.91 (d, J=2 Hz 1H), 8.21 (d, J=2 Hz, 1H), 8.12 (d, J=8 Hz, 1H), 7.84 (d, J=7 Hz, 1H), 7.72 (t, J=7 Hz, 1H), 7.54 (t, J=7 Hz, 1,H), 4.72 (M, 1H), 2.73 (M, 2H). The (S)-enantiomer of 25-2 was prepared using the enzymatic resolution described by Soloshonok et al. (Tetrahedron: Asymmetry, 6, 1601, 1995). The resolved material was converted to 25-3 by refluxing in ethanolic HCl.

$^1$H NMR (300 MHz, CD$_3$OD): δ9.25 (d, J=2 Hz 1H), 8.31 (d, J=2 Hz, 1H), 8.15 (d, J=8 Hz, 1H), 7.84 (d, J=7 Hz, 1H), 7.72 (t, J=7 Hz, 1H), 7.54 (t, J=7 Hz, 1,H), 4.72 (M, 1H), 4.15 (q, J=6 Hz, 2H), 2.73 (M, 2H) 1.18 (t, J=6 Hz, 3H).

N—Boc-Glycyl-3(S)-guinolin-3-yl-β-alanine ethyl ester (25-4)

N—Boc-Glycine (60.7 mg, 0.35 mmol), amine 25-3 (0.10 mg, 3.15 mmol), NMM (0.13 mL, 1.26 mmol) and EDC (78.5 mg, 0.41 mmol) were combined in 3 mL DMF. After stirring overnight the mixture was concentrated, diluted with EtOAc, washed with water, sat. NaHCO$_3$, water, and brine, dried (MgSO$_4$), filtered and concentrated. Flash chromatography (silica, EtOAc) provided 25-4 as a colorless oil.

TLC R$_f$ 0.45 (silica, EtOAc)

$^1$H NMR (300 MHz, CDCl$_3$): δ8.88 (d, J=2 Hz 1H), 8.09 (d, J=2 Hz, 1H), 8.05 (d, J=8 Hz, 1H), 7.79 (d, J=6 Hz, 1H), 7.72 (t, J=6 Hz, 1H), 7.68 (br d, 1H), 7.54 (t, J=7 Hz, 1,H), 5.65 (M, 1H), 5.18 (br, t, 1H), 4.15 (q, J=6 Hz, 2H), 3.00 (M, 2H), 1.21 (s, 9H), 1.08 (t, J=7 Hz, 3H).

Glycyl-3(S)-guinolin-3-yl-β-alanine dihydrochloride (25-5)

The ester 25-4 (92 mg, 0.23 mmol) was dissolved in HCl saturated ethanol and stirred at room temperature for 3.5 h then concentrated at reduced pressure to afford 25-5 as a white solid.

$^1$H NMR (300 MHz, CD$_3$OD): δ9.38 (s, 1H), 9.15 (s, 1H), 8.45 (d, J=6 Hz, 1H), 8.22 (d, J=6 Hz, 1H), 8.17 (t, J=6 Hz, 1H), 8.00 (t, J=7 Hz, 1,H), 5.65 (M, 1H), 5.18 (br, t, 1H), 4.15 (q, J=6 Hz, 2H), 3.00 (M, 2H), 1.21 (s, 9H), 1.08 (t, J=7 Hz, 3H).

4-(1,2,3,4-Tetrahydro-1,8-naphthyridin-7-yl)butanoyl-glycyl-3(S)-quinolin-3-yl-β-alanine ethyl ester (25-6).

A mixture of 19-5 (57 mg, 0.22 mmol), 25-5 (84 mg, 0.22 mmol), NMM (123 mL, 1.12 mmol) and, HOBT (39 mg, 0.29 mmol) and EDC (55 mg, 0.29 mmol) in 2 mL DMF was stirred overnight. After diluting with EtOAc the mixture was washed with sat. NaHCO$_3$, water, and brine, dried (MgSO$_4$), filtered and concentrated,and chromatographed on silica (30% MeOH/EtOAc) providing 25-6.

$^1$H NMR (300 MHz, CDCl$_3$): δ9.91(s, 1H), 8.56 (br t, 1H), 8.18 (br d, 1H), 8.16 (s, 1H), 8.05 (d, J=6 Hz, 1H), 7.82 (d, J=6 Hz, 1H), 7.73 (t, J=6 Hz, 1H), 7.54 (t, J=6 Hz, 1H), 7.08 (d, J=7 Hz, 1H), 6.33 (d, J=7 Hz, 1H), 5.71 (m, 1H), 5.69 (br s, 1H), 4.15 (d, J=7 Hz, 2H), 4.05, (t, J=7 Hz, 2H), 3.53 (q, J=6 Hz, 2H), 3.43 (m, 2H), 3.00 (m, 2H), 2.69 (t, J=6 Hz, 2H), 2.60 (t, J=7 Hz, 2H), 2.46 (t, J=6 Hz, 2H), 2.25 (t, J=7 Hz, 2H), 2.05–1.90 (m, 4H), 1.08 (t, J=7 Hz, 3H).

4-(1,2,3,4-Tetrahydro-1,8-naphthyridin-7-yl)butanoyl-glycyl-3(S)-quinolin-3-yl-β-alanine (25-7).

Ester 25-6 was dissolved in 5 mL 6N HCl and warmed to 50° C. for 1.5 h then concentrated and the residue chromatographed on silica (75% EtOH. NH$_3$/EtOAc) to afford 25-7.

$^1$H NMR (300 MHz, D$_2$O): δ8.71(s, 1H), 8.16 (s, 1H), 7.71 (d, J=6 Hz, 1H), 7.64 (d, J=6 Hz, 1H), 7.54 (t, J=6 Hz, 1H), 7.54 (t, J=6 Hz, 1H), 7.08 (d, J=7 Hz, 1H), 6.06 (d, J=7 Hz, 1H), 5.35 (m, 1H), 4.81 (s, 2H), 3.53 (q, J=6 Hz, 2H), 3.43 (m, 2H), 3.00 (m, 2H), 2.69 (t, J=6 Hz, 2H), 2.60 (t, J=7

Hz, 2H), 2.46 (t, J=6 Hz, 2H), 2.25 (t, J=7 Hz, 2H), 2.05–1.90 (m, 4H).

EXAMPLE 26

Tablet Preparation

Tablets containing 25.0, 50.0, and 100.0 mg., respectively, of the following active compounds are prepared as illustrated below:

4-(2-Amino-pyridin-6-yl)butanoyl-N-cyclopropylglycyl-3 (R)-(2-phenethyl)-β-alanine;

4-(2-Bocamino-pyridin-6-yl)butanoyl-N-cyclopropylglycyl-3(R)-[(2-indol-3-yl)ethyl]-β-alanine; and 4-(2-Amino-pyridin-6-yl)butanoyl-N-cyclopropylglycyl-3 (R)-[(2-indol-3-yl)ethyl]-β-alanine.

Table for Doses Containing from 25–100 MG of the Active Compound

|  | Amount-mg | | |
| --- | --- | --- | --- |
| Active Compound | 25.0 | 50.0 | 100.1 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 27

Intravenous Formulations

An intravenous dosage form of the above-indicated active compound is prepared as follows:

| Active Compound | 0.5–10.0 mg |
| --- | --- |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopoeia/National Formulary for 1995, published by United States Pharmacopoeial Convention, Inc., Rockville, Md., copyright 1994.

EXAMPLE 28

Intravenous Formulation

A pharmaceutical composition was prepared at room temperature using 4-(2-Aminothiazol-4-yl)butanoyl-glycyl-2(S)-phenylsulfonamido-β-alanine t-butyl ester, a citrate buffer, and sodium chloride, to obtain a concentration of 4-(2-Aminothiazol-4-yl)butanoyl-glycyl-2(S)-phenylsulfonamido-β-alanine t-butyl ester of 0.25 mg/ml.

800 grams of water was introduced into a standard pharmaceutical mixing vessel. 0.25 grams of the ester was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
| --- | --- |
| 4-(2-Aminothiazol-4-yl)butanoyl-glycyl-2(S)-phenylsulfonamido-β-alanine t-butyl ester | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

Therapeutic Treatment

Oral dosages of the compounds used to elicit a vitronectin receptor antaginizing effect will range between about 0.01 mg per kg of body weight per day (mg/kg/day) to about 100 mg/kg/day and preferably 0.01–50 mg/kg/day and more preferably 0.01–20 mg/kg/day, e.g. 0.1 mg/kg/day, 1.0 mg/kg/day, 5.0 mg/kg/day, or 10 mg/kg/day. Advantageously, compounds of the present invention may be administered in divided doses of two, three, or four times daily. Intravenously, the most preferred doses will range from about 1 to about 10 mg/kg/minute during a constant rate infusion. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

EIB Assay

Duong et al., *J. Bone Miner. Res.*, 8:S 378, describe a system for expressing the human integrin $\alpha_v\beta_3$. It has been suggested that the integrin is involved in the attachment of osteoclasts to bone matrix, since antibodies against the integrin, or RGD-containing molecules, such as echistatin (European Publication 382 451), can effectively block bone resorption.

Reaction Mixture:

1. 175 µl TBS buffer (50 mM Tris.HCl pH 7.2, 150 mM NaCl, 1% BSA, 1 mM $CaCl_2$, 1 mM $MgCl_2$).
2. 25 µl cell extract (dilute with 100 mM octylglucoside buffer to give 2000 cpm/25 µl).
3. $^{125}$I-echistatin (25 µl/50,000 cpm) (see EP 382 451).
4. 25 µl buffer (total binding) or unlabeled echistatin (non-specific binding).

The reaction mixture was then incubated for 1 h at room temp. The unbound and the bound $\alpha_v\beta_3$ were separated by filtration using a Skatron Cell Harvester. The filters (prewet in 1.5% polyethyleneimine for 10 mins) were then washed with the wash buffer (50 mM Tris HCl, imM $CaCl_2$/$MgCl_2$, pH 7.2). The filter was then counted in a gamma counter.

SPA Assay

Materials:

1. Wheatgerm agglutinin Scintillation Proximity Beads (SPA): Amersham
2. Octylglucopyranoside: Calbiochem
3. HEPES: Calbiochem
4. NaCl: Fisher
5. $CaCl_2$: Fisher
6. $MgCl_2$: SIGMA
7. Phenylmethylsulfonylfluoride (PMSF): SIGMA
8. Optiplate: PACKARD
9. 29-10 (see preparation below)(specific activity 500–1000 Ci/mmole)
10. test compound
11. Purified integrin receptor: $\alpha_v\beta_3$ was purified from 293 cells overexpressing $\alpha_v\beta_3$ (Duong et al., *J. Bone Min. Res.*, 8:S378, 1993) according to Pytela (*Methods in Enzymology*, 144:475, 1987)
12. Binding buffer: 50 mM HEPES, pH 7.8, 100 mM NaCl, 1 mM $Ca^{2+}/Mg^{2+}$, 0.5 mM PMSF
13. 50 mM octylglucoside in binding buffer: 50-OG buffer Procedure:

1. Pretreatment of SPA beads:
   500 mg of lyophilized SPA beads were first washed four times with 200 ml of 50-OG buffer and once with 100 ml of binding buffer, and then resuspended in 12.5 ml of binding buffer.
2. Preparation of SPA beads and receptor mixture
   In each assay tube, 2.5 μl (40 mg/ml) of pretreated beads were suspended in 97.5 μl of binding buffer and 20 μl of 50-OG buffer. 5 μl (~30 ng/μl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 μl of binding buffer and 25 μl of 50-OG buffer.
3. Reaction
   The following were sequentially added into Optiplate in corresponding wells:
   (i) Receptor/beads mixture (75 μl)
   (ii) 25 μl of each of the following: compound to be tested, binding buffer for total binding or 29-8 (see preparation below) for non-specific binding (final concentration 1 μM)
   (iii) 29-10 in binding buffer (25 μl, final concentration 40 pM)
   (iv) Binding buffer (125 μl)
   (v) Each plate was sealed with plate sealer from PACKARD and incubated overnight with rocking at 4° C.
4. Plates were counted using PACKARD TOPCOUNT
5. % inhibition was calculated as follows:
   A=total counts
   B=nonspecific counts
   C=sample counts % inhibition=$[\{(A-B)-(C-B)\}/(A-B)]/(A-B) \times 100$

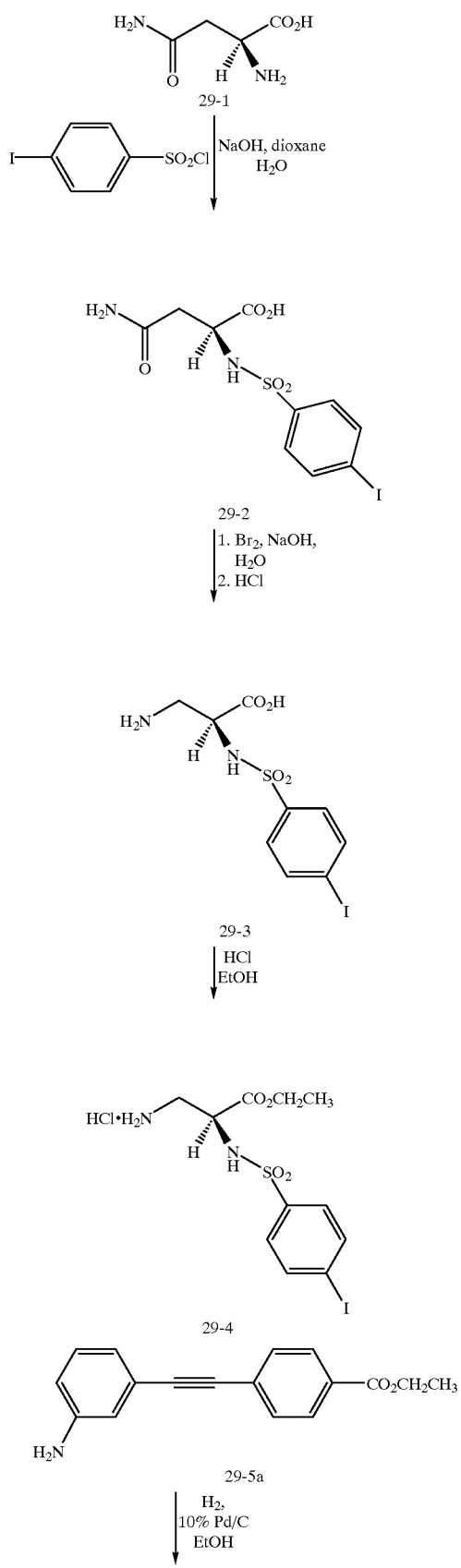

SCHEME 29

-continued

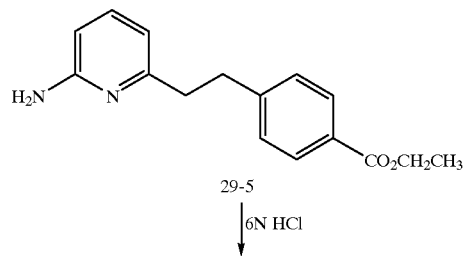
29-5

↓ 6N HCl

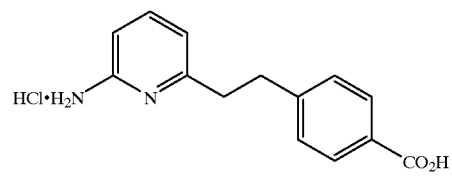
29-6

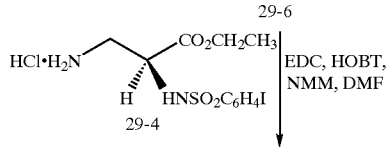
29-4

EDC, HOBT,
NMM, DMF

↓

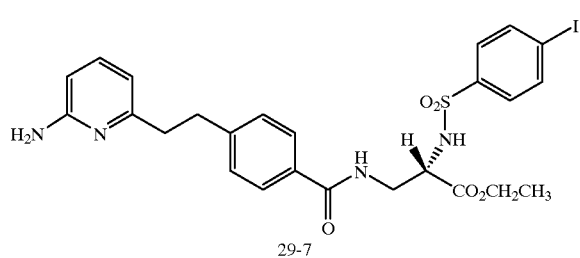
29-7

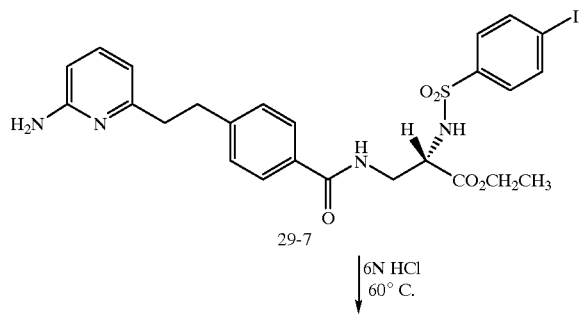
29-7

↓ 6N HCl
60° C.

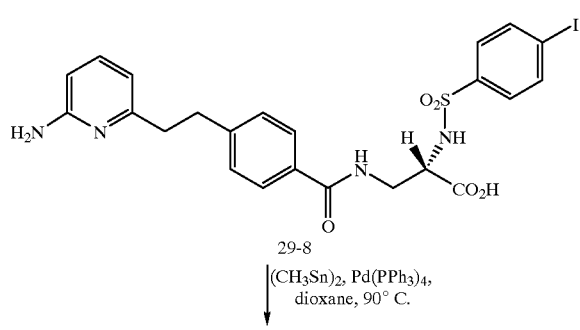
29-8

↓ (CH₃Sn)₂, Pd(PPh₃)₄,
dioxane, 90° C.

-continued

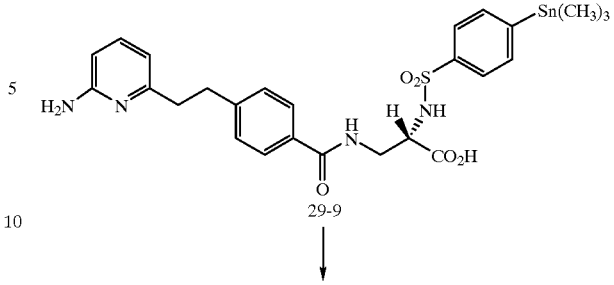
29-9

↓

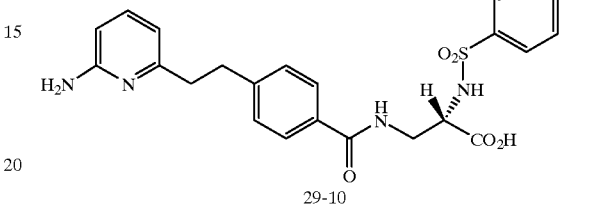
29-10

N-(4-Iodo-]2henylsulfonylamino)-L-asparaine (29-2)

To a stirred solution of acid 29-1 (4.39 g, 33.2 mmol), NaOH (1.49 g, 37.2 mmol), dioxane (30 ml) and H₂O (30 ml) at 0° C. was added pipsyl chloride (10.34 g, 34.2 mmol). After ~5 minutes, NaOH (1.49, 37.2 mmol) dissolved in 15 ml H₂O, was added followed by the removal of the cooling bath. After 2.0 h, the reaction mixture was concentrated. The residue was dissolved in H₂O (300 ml) and then washed with EtOAc. The aqueous portion was cooled to 0° C. and then acidified with concentrated HCl. The solid was collected and then washed with Et₂O to provide acid 29-2 as a white solid.

$^1$H NMR (300 MHz, D₂O) δ7.86 (d, 2H, J=8 Hz), 7.48 (d, 2H, J=8 Hz) 3.70 (m, 1H), 2.39 (m, 2H).

2(S)-(4-Iodo-phenylsulfonylamino)-β-alanine (29-3)

To a stirred solution of NaOH (7.14 g, 181.8 mmol) and H₂O (40 ml) at 0° C. was added Br₂ (1.30 ml, 24.9 mmol) dropwise over a ten minute period. After ~5 minutes, acid 29-2 (9.9 g, 24.9 mmol), NaOH (2.00 g, 49.8 mmol) and H₂O (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid 29-3 as a white solid.

$^1$H NMR (300 MHz, D₂O) δ8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (29-4)

HCl gas was rapidly bubbled through a suspension of acid 29-3 (4.0 g, 10.81 mmol) in EtOH (50 ml) at 0° C. for 10 minutes. The cooling bath was removed and the reaction was heated to 60° C. After 18 h, the reaction was concentrated to provide ester 29-4 as a white solid.

$^1$H NMR (300 MHz, CD₃OD) δ7.98 (d, 2H, J=8 Hz), 7.63 (d, 2H, J=8 Hz), 4.25 (q, 1H, J=5Hz), 3.92 (m, 2H), 3.33 (m, 1H), 3.06 (m, 1H), 1.01 (t, 3H J=7 Hz).

Ethyl 4-[2-(2-Aminopyridin-6-yl)ethyl]benzoate (29-5)

A mixture of ester 29-5a (700 mg, 2.63 mmol), (for preparation, see: Scheme 29 of PCT International Application Publication No. WO 95/32710, published Dec. 7, 1995) 10% Pd/C (350 mg) and EtOH were stirred under 1 atm $H_2$. After 20 h, the reaction was filtered through a celite pad and then concentrated to provide ester 29-5 as a brown oil.

TLC $R_f$=0.23 (silica, 40% EtOAc/hexanes)

$^1$H NMR (300 MHz, $CDCl_3$) δ7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (29-6)

A suspension of ester 29-5 (625 mg, 2.31 mmol) in 6N HCl (12 ml) was heated to 60° C. After ~20 h, the reaction was concentrated to give acid 29-6 as a tan solid.

$^1$H NMR (300 MHz, $CD_3OD$) δ7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodo-phenylsulfonylamino)-β-alanine (29-7)

A solution of acid 29-6 (400 mg, 1.43 mmol), amine 29-4 (686 mg, 1.57 mmol), EDC (358 mg, 1.86 mmol), HOBT (252 mg, 1.86 mmol), NMM (632 μl, 5.72 mmol) and DMF (10 ml) was stirred for ~20 h. The reaction was diluted with EtOAc and then washed with sat $NaHCO_3$, brine, dried ($MgSO_4$) and concentrated. Flash chromatography (silica, EtOAC 5% isopropanol/EtOAc) provided amide 29-7 as a white solid.

TLC $R_f$=0.4 (silica, 10% isopropanol/EtOAc)

$^1$H NMR (300 MHz, $CD_3OD$) δ7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenylsulfonylamino)-β-alanine (29-8)

A solution of ester 29-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/$NH_4OH$/$H_2O$) provided acid 29-8 as a white solid.

TLC $R_f$=0.45 (silica, 20:20:1:1 EtOAc/EtOH/$NH_4OH$/$H_2O$)

$^1$H NMR (400 MHz, DMSO) δ8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl]benzoyl-2(S)-(4-trimethylstannylphenylsulfonylamino)-β-alanine (29-9)

A solution of iodide 29-8 (70 mg, 0.1178 mmol), (($CH_3$)$_3$Sn)$_2$ (49 μl, 0.2356 mmol), Pd(PPh$_3$)$_4$ (5 mg) and dioxane (7 ml) was heated to 90° C. After 2 h, the reaction was concentrated and then purified by prep HPLC (Delta-Pak $C_{18}$ 15 μM 100 Å°, 40×100 mm; 95:5→5:95 $H_2O$/$CH_3CN$) provided the trifluoroacetate salt. The salt was suspended in $H_2O$ (10 ml), treated with $NH_4OH$ (5 drops) and then lyophilized to provide amide 29-9 as a white solid.

$^1$H NMR (400 MHz, DMSO) δ8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodo-phenylsulfonylamino)-β-alanine (29-10)

An iodobead (Pierce) was added to a shipping vial of 5 mCi of Na$^{125}$I (Amersham, IMS30) and stirred for five minutes at room temperature. A solution of 0.1 mg of 29-9 in 0.05 mL of 10% $H_2SO_4$/MeOH was made and immediately added to the Na$^{125}$I/iodobead vial. After stirring for three minutes at room temperature, approximately 0.04–0.05 mL of $NH_4OH$ was added so the reaction mixture was at pH 6–7. The entire reaction mixture was injected onto the HPLC for purification [Vydac peptide-protein C-18 column, 4.6× 250 mm, linear gradient of 10% acetonitrile (0.1% (TFA) :$H_2O$ (0.1% TFA) to 90% acetonitrile (0.1% TFA):$H_2O$ (0.1% TFA) over 30 minutes, 1 mL/min]. The retention time of 29-10 is 17 minutes under these conditions. Fractions containing the majority of the radioactivity were pooled, lyophilized and diluted with ethanol to give approximately 1 mCi of 29-10, which coeluted on HPLC analysis with an authentic sample of 29-8.

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UViis Diode Array Spectrophotometer. Sample radioactivities were determined in a Packard A5530 gamma counter.

αvβ5 Attachment Assay

Duong et al., J. Bone Miner. Res., 1:S 290, describe a system for expressing the human αvβ5.

Materials:
1. Media and solutions used in this assay are purchased from BRL/Gibco, except BSA and the chemicals are from Sigma.
2. Attachment medium: HBSS with 1 mg/ml heat-inactivated fatty acid free BSA and 2 mM $CaCl_2$.
3. Glucosaminidase substrate solution: 3.75 mM p-nitrophenyl-N-acetyl-beta-D-glucosaminide, 0.1 M sodium citrate, 0.25% Triton, pH 5.0.
4. Glycine-EDTA developing solution: 50 mM glycine, 5 mM EDTA, pH 10.5.

Methods:
1. Plates (96 well, Nunc Maxi Sorp) were coated overnight at 4° C. with human vitronectin (3 ug/ml) in 50 mM carbonate buffer (pH 9/.6), using 100 μl/well. Plates were then washed 2× with DPBS and blocked with 2% BSA in DPBS for 2 h at room temperature. After additional washes (2×) with DPBS, plates were used for cell attachment assay.
2. 293 (alpha v beta 5) cells were grown in MEM media in presence of 10% fetal calf serum to 90% confluence. Cells were then lifted from dishes with 1×Trypsin/EDTA and washed 3× with serum free MEM. Cells were resuspended in attachment medium (3×10$^5$ cells/ml).
3. Test compounds were prepared as a series of dilutions at 2× concentrations and added as 50 μl/well. Cell suspension was then added as 50 ml/well. Plates were incubated at 37° C. with 55 $CO_2$ for 1 hour to allow attachment.
4. Non-adherent cells were removed by gently washing the plates (3×) with DPBS and then incubated with glucosaminidase substrate solution (100 μl/well), overnight at room temperature in the dark. To quantitate cell numbers, standard curve of glucosaminidase activity was determined for each experiment by adding samples of cell suspension directly to wells containing the enzyme substrate solution.

5. The next day, the reaction was developed by addition of 185 μl/well of gylcine/EDTA solution and reading absorbance at 405 nm using a Molecular Devices V-Max plate reader. Average test absorbance values (4 wells per test samples) were calculated. Then, the number of attached cells at each drug concentration was quantitated versus the standard curve of cells using the Softmax program.

What is claimed is:

1. A method for inhibiting a condition selected from the group consisting of restenosis, angiogenesis, diabetic retinopathy, inflammation, and tumor growth in a mammal which comprises administering to the mammal a therapeutically effective amount of a compound of the formula:

$$X-(CH_2)_m-Y-(CH_2)_n-\overset{O}{\underset{}{C}}-\underset{R^3}{N}-CH_2-\overset{O}{\underset{}{C}}-NH-\underset{}{CH}-\underset{R^5}{\overset{R^4}{CH}}-CO_2R^6$$

and pharmaceutically acceptable salts thereof, wherein

X is
- a 5- or 6-membered monocyclic aromatic ring system containing 0, 1, 2, 3 or 4 heteroatoms selected from N, O or S and either unsubstituted or substituted with $R^1$ or $R^2$, or
- a 9- to 10-membered polycyclic ring system, wherein one or more of the rings is aromatic, containing 0, 1, 2, 3 or 4 heteroatoms selected from N, O or S and either unsubstituted or substituted with $R^1$ or $R^2$, wherein $R^1$ and $R^2$ are independently selected from the group consisting of
hydrogen, F, Cl, Br, I,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-4}$ alkoxy,
$C_{1-4}$ alkoxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl;

Y is $-(CH_2)_{0-6}-$, $-C\equiv C-$, $-C=C\sim\hspace{-1mm}\sim$,

-continued $-\overset{O}{\underset{}{C}}-$, $-\underset{R^7}{\overset{NHR^9}{C}}-$, $-\underset{}{\overset{R^8}{N}}-$, $-O-$, $-SO_2NH-$, $-NHSO_2-$, $-\underset{}{\overset{R^8}{N}}-\overset{O}{\underset{}{C}}-$, $-\overset{O}{\underset{}{C}}-\underset{}{\overset{R^8}{N}}-$, $-S(O)_{0-2}-CH_2-$, [phenyl ring],

[cyclohexyl ring], [heterocyclic ring with Z], $R^1-N\underset{R^2}{\overset{}{\frown}}N-$, or $R^1-N\underset{R^2}{\overset{}{\frown}}$, where Z is O, $NR^8$, or S; and $R^8$ is defined as $R^1$ above;

$R^3$ and $R^4$ are independently
hydrogen,
a five or six membered mono or nine or ten membered polycyclic unsaturated, partially or fully saturated ring system containing 0, 1, 2, 3, or 4 heteroatoms selected from nitrogen, oxygen or sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, —$(CH_2)_n$-aryl, wherein n=1–4 and aryl is defined as a five or six membered unsaturated or partially saturated monocyclic ring system, or nine or ten membered polycyclic ring system wherein at least one of the rings is unsaturated or partially saturated and each of the other rings is optionally unsaturated, partially saturated or fully saturated, said aryl group containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, halogen,
hydroxyl,
$C_{1-5}$alkylcarbonylamino,
aryl$C_{1-5}$ alkoxy,
$C_{1-5}$ alkoxycarbonyl,
aminocarbonyl,
$C_{1-5}$ alkylaminocarbonyl,
$C_{1-5}$ alkylcarbonyloxy,
$C_{3-8}$ cycloalkyl,
oxo,
amino,
$C_{1-3}$ alkylamino,
amino$C_{1-3}$ alkyl,
arylaminocarbonyl,
aryl$C_{1-5}$alkylaminocarbonyl,
aminocarbonyl, aminocarbonyl-$C_{1-4}$ alkyl,
hydroxycarbonyl,
hydroxycarbonyl $C_{1-5}$ alkyl,
$C_{1-6}$ alkyl, either unsubstituted or substituted, with one or more groups selected from halogen, hydroxyl, $C_{1-5}$ alkylcarbonylamino, aryl$C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino$C_{1-3}$ alkyl, arylaminocarbonyl, aryl$C_{1-5}$ alkylaminocarbonyl, aminocarbonyl, aminocarbonyl-$C_{1-4}$ alkyl, hydroxycarbonyl, or hydroxycarbonyl $C_{1-5}$ alkyl, provided that the carbon atom to which $R^3$ and $R^4$ are attached bears only one heteroatom,
—$(CH_2)_m C \equiv CH$,
—$(CH_2)_m C \equiv C — C_{1-6}$ alkyl,
—$(CH_2)_m C \equiv C — C_{3-7}$ cycloalkyl,
—$(CH_2)_m C \equiv C —$ aryl,
—$(CH_2)_m C \equiv C — C_{1-6}$ alkyl aryl,
—$(CH_2)_m CH = CH_2$,
—$(CH_2)_m CH = CH\ C_{1-6}$ alkyl,
—$(CH_2)_m CH = CH — C_{3-7}$cycloalkyl,
—$(CH_2)_m CH = CH$ aryl,
—$(CH_2)_m CH = CH\ C_{1-6}$ alkyl aryl,
—$(CH_2)_m SO_2 C_{1-6}$ alkyl, or
—$(CH_2)_m SO_2 C_{1-6}$ alkylaryl;
$R^5$ is
hydrogen,
fluorine,
$C_{1-8}$ alkyl,
hydroxyl,
hydroxy $C_{1-6}$ alkyl,
carboxy,
carboxy $C_{1-6}$ alkyl,
$C_{1-6}$ alkyloxy;
$C_{3-8}$ cycloalkyl,
aryl $C_{1-6}$ alkyloxy,
aryl,
aryl $C_{1-6}$ alkyl,
$C_{1-6}$ alkylcarbonyloxy,
amino,
$C_{1-6}$ alkylamino,
amino $C_{1-6}$ alkyl,
$C_{1-6}$ alkylamino $C_{1-6}$ alkyl,
aryl amino,
aryl amino $C_{1-6}$ alkyl,
aryl $C_{1-6}$ alkylamino,
aryl $C_{1-6}$ alkylamino $C_{1-6}$ alkyl,
aryl carbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
aryl sulfonylamino $C_{1-6}$ alkyl,
aryl sulfonylamino,
aryl $C_{1-6}$ alkylsulfonylamino,
aryl $C_{1-6}$ alkylsulfonylamino $C_{1-6}$ alkyl,
$C_{1-8}$ alkyloxycarbonylamino,
$C_{1-8}$ alkyloxycarbonylamino $C_{1-8}$ alkyl,
aryl $C_{1-8}$ alkyloxycarbonylamino,
aryl oxycarbonylamino,
aryl oxycarbonylamino $C_{1-8}$ alkyl,
aryl $C_{1-8}$ alkyloxycarbonylamino $C_{1-8}$ alkyl,
$C_{1-8}$ alkylcarbonylamino,
$C_{1-8}$ alkylcarbonylamino $C_{1-6}$ alkyl,
aryl carbonylamino $C_{1-6}$ alkyl,
aryl carbonylamino,
aryl $C_{1-6}$ alkylcarbonylamino,
aryl $C_{1-6}$ alkylcarbonylamino $C_{1-6}$ alkyl,
$C_{1-8}$ alkylaminocarbonylamino,
aminocarbonylamino,
aminocarbonylamino $C_{1-6}$ alkyl,
$C_{1-8}$ alkylaminocarbonylamino $C_{1-6}$ alkyl,
aryl aminocarbonylamino $C_{1-6}$ alkyl,
aryl aminocarbonylamino,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
aminosulfonylamino,
$C_{1-8}$ alkylaminosulfonylamino,
$C_{1-8}$ alkylaminosulfonylamino $C_{1-6}$ alkyl,
aryl aminosulfonylamino $C_{1-6}$ alkyl,
aryl aminosulfonylamino,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$ alkyl,
aryl sulfonyl,
aryl sulfonyl $C_{1-6}$ alkyl,
aryl alkylsulfonyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
aryl carbonyl $C_{1-6}$ alkyl,
aryl carbonyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
aryl thiocarbonylanmino $C_{1-6}$ alkyl,
aryl thiocarbonylamino,
aryl $C_{1-6}$ alkylthiocarbonylamino,
aryl $C_{1-6}$ alkylthiocarbonylamino $C_{1-6}$ alkyl,
aminocarbonyl $C_{1-6}$ alkyl,
aminocarbonyl,
$C_{1-8}$ alkylaminocarbonyl,
$C_{1-8}$ alkylaminocarbonyl $C_{1-6}$ alkyl,
aryl aminocarbonyl $C_{1-6}$ alkyl,
aryl aminocarbonyl,
aryl $C_{1-8}$ alkylaminocarbonyl,
aryl $C_{1-8}$ alkylaminocarbonyl $C_{1-6}$ alkyl,
wherein alkyl groups and aryl groups are optionally unsubstituted or substituted with one or more substituents selected from $R^1$ and $R^2$; and $R^6$, $R^7$, and $R^9$ are independently
hydrogen,
$C_{1-8}$ alkyl,
aryl,
aryl $C_{1-8}$ alkyl,
hydroxy,
$C_{1-8}$ alkyloxy,
aryloxy,
aryl $C_{1-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy,
$C_{1-8}$ alkylaminocarbonylmethyleneoxy, or
$C_{1-8}$ dialkylaminocarbonylmethyleneoxy,
and wherein m and n are integers 0–6.

2. A method of claim 1 wherein the compound has the formula:

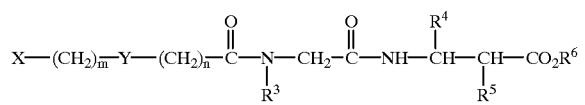

and pharmaceutically acceptable salts thereof, wherein X is

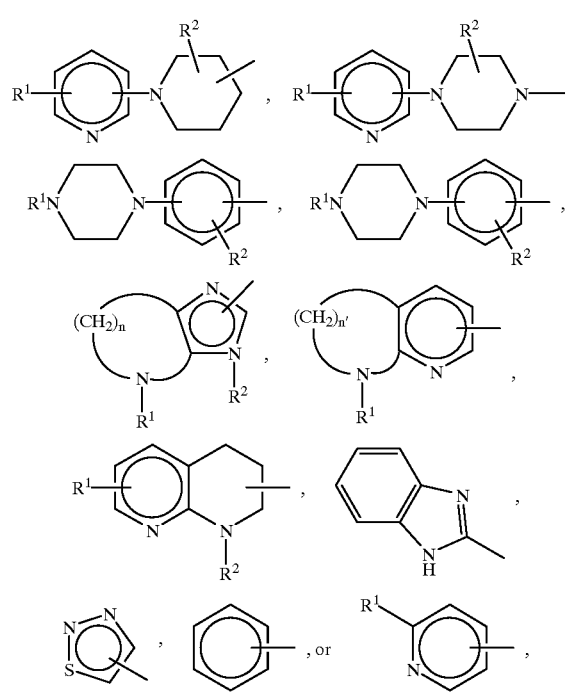

wherein n is 2–4, and n' is 2 or 3, and
wherein $R^1$ and $R^2$ are independently selected from the
  group
  consisting of
  hydrogen, F, Cl, Br, I,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-4}$ alkoxy,
  $C_{1-4}$ alkoxy $C_{1-6}$ alkyl,
  carboxy,
  carboxy $C_{1-6}$ alkyl,
  $C_{1-3}$ alkoxycarbonyl,
  $C_{1-3}$ alkoxycarbonyl $C_{1-6}$ alkyl,
  carboxy $C_{1-6}$ alkyloxy,
  hydroxy, and
  hydroxy $C_{1-6}$ alkyl.

3. A method of claim 2 wherein the compound has the formula

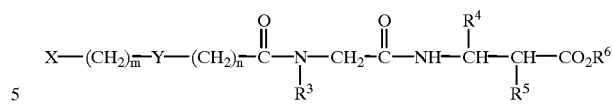

and pharmaceutically acceptable salts thereof, wherein X is

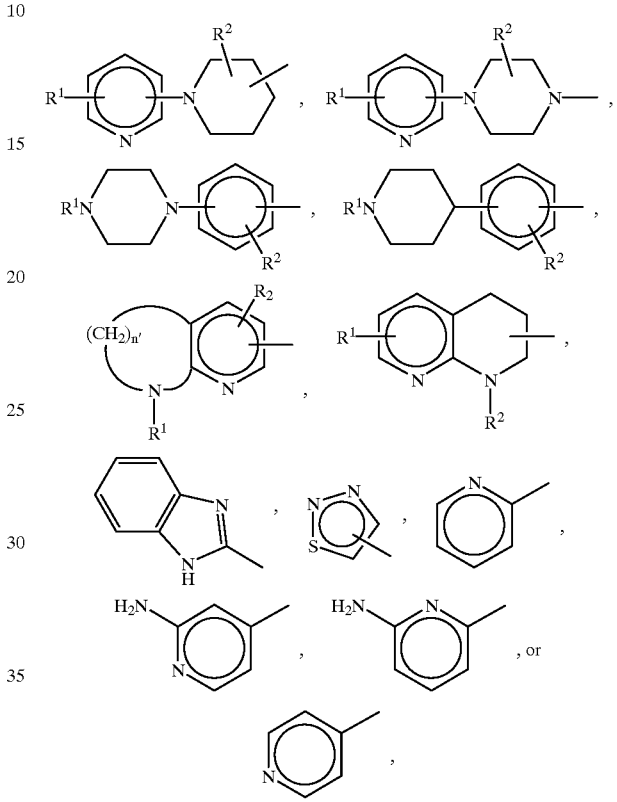

wherein n' is 2 or 3, and
Y is

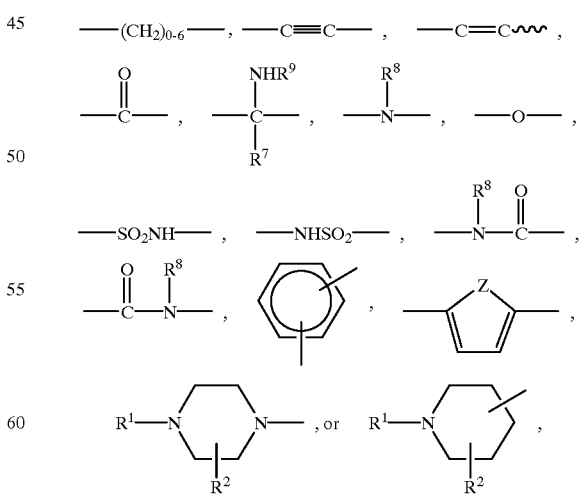

where Z is O, $NR^8$, or S; and $R^8$ is defined as $R^1$.

4. A method of claim 3 wherein the compound has the formula

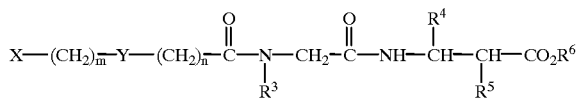

and pharmaceutically acceptable salts thereof, wherein
X is

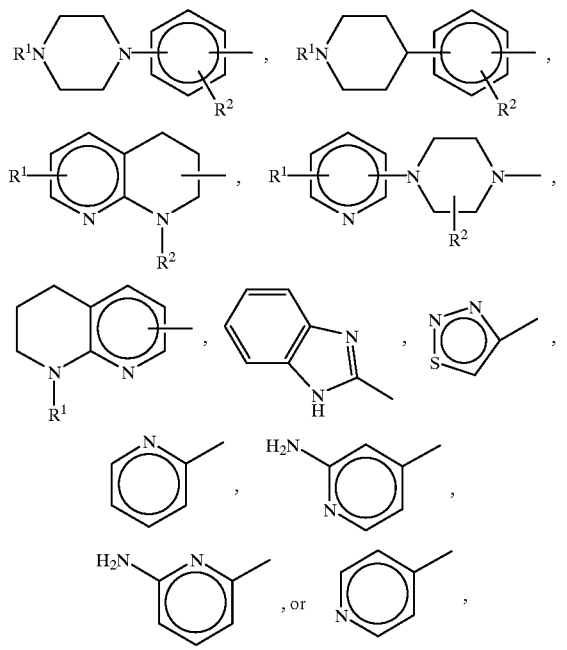

wherein $R^1$ and $R^2$ are independently selected from the group consisting of
hydrogen or
amino,
amino $C_{1-8}$ alkyl;
Y is

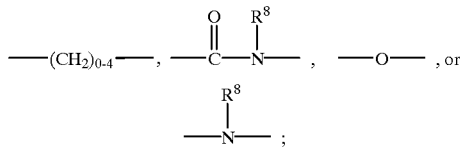

$R^8$ is hydrogen or aryl $C_{0-8}$ alkyl;
$R^3$ is
hydrogen,
a six membered monocyclic unsaturated, partially or fully saturated ring system, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy,
—$(CH_2)_n$-aryl, wherein n=1–4 and aryl is defined as a six membered monocyclic unsaturated or partially saturated ring system, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy,
$C_{3-8}$ cycloalkyl, or
$C_{1-6}$alkyl, either unsubstituted or substituted, with $C_{3-8}$ cycloalkyl;
$R^4$ is
hydrogen,
—$(CH_2)_n$-aryl, wherein n=0–4 and aryl is defined as a six membered monocyclic unsaturated or partially saturated ring or a nine or ten membered polycyclic ring system wherein at least one of the rings is unsaturated or partially saturated and each of the other rings is optionally unsaturated, partially saturated or fully saturated, said aryl group either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl$C_{0-5}$ alkyl, or hydroxycarbonyl$C_{1-5}$ alkoxy,
$C_{1-6}$alkyl, or
—$(CH_2)_{0-4}$ C≡CH;
$R^5$ is
hydrogen,
aryl sulfonylamino $C_{1-6}$ alkyl,
aryl sulfonylamino,
aryl $C_{1-6}$ alkylsulfonylamino,
aryl $C_{1-6}$ alkylsulfonylamino $C_{1-6}$ alkyl,
$C_{1-8}$ alkylsulfonylamino,
$C_{1-8}$ alkylsulfonylamino $C_{1-6}$ alkyl,
aryl sulfonylamino $C_{1-6}$ alkyl,
aryl sulfonylamino,
aryl $C_{1-6}$ alkylsulfonylamino,
aryl $C_{1-6}$ alkylsulfonylamino $C_{1-6}$ alkyl,
minosulfonylamino $C_{1-6}$ alkyl,
aminosulfonylamino,
$C_{1-8}$ alkylaminosulfonylamino,
$C_{1-8}$ alkylaminosulfonylamino $C_{1-6}$ alkyl,
aryl aminosulfonylamino $C_{1-6}$ alkyl,
aryl aminosulfonylamino,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$alkyl,
aryl sulfonyl $C_{1-6}$alkyl,
aryl sulfonyl,
aryl $C_{1-6}$ alkylsulfonyl,
aryl $C_{1-6}$ alkylsulfonyl $C_{1-6}$alkyl,
wherein alkyl groups and aryl groups may be unsubstituted or substituted with one or more substituents selected from $R^1$ or $R^2$; and
$R^6$ is
hydrogen,
$C_{1-8}$ alkyl, or
aryl,
aryl $C_{1-8}$ alkyl.

5. A method of claim 4 wherein the compound has the formula

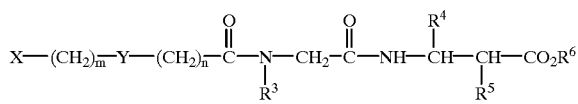

and pharmaceutically acceptable salts thereof, wherein

X is

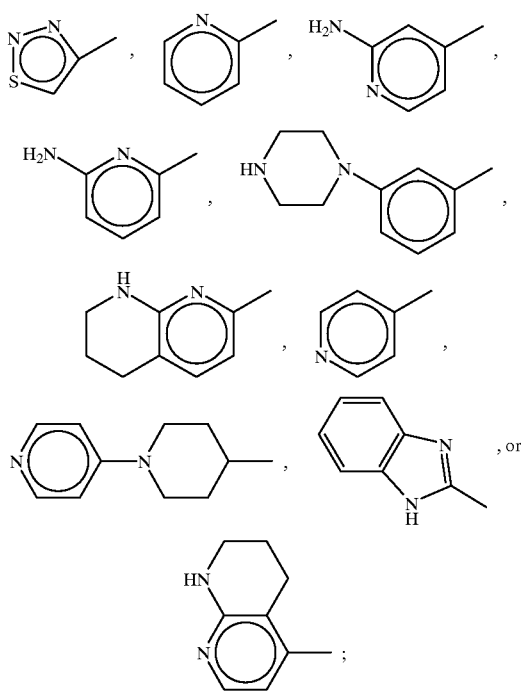

Y is

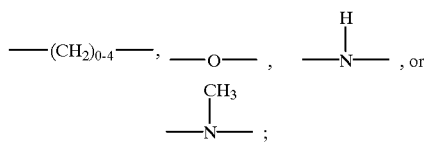

R³ is
hydrogen,
methyl,

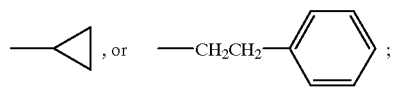

R⁴ is
hydrogen,
methyl,

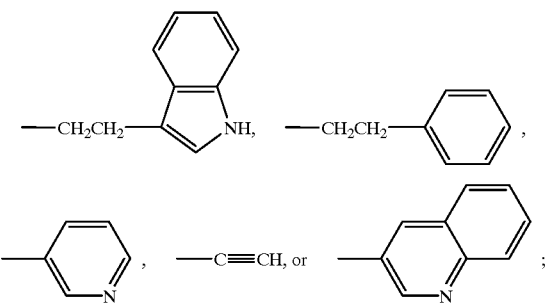

R⁵ is
hydrogen, or

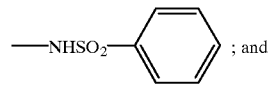; and

R⁶ is
hydrogen,
methyl,
ethyl, or
t-butyl.

6. A method of claim 5 wherein the compound is selected from the group consisting of
4-(2-Aminothiazol-4-yl)butanoyl-glycyl-2(S)-phenylsulfonamido-β-alanine t-butyl ester,
4-(2-Aminothiazol-4-yl)butanoyl-glycyl-2(S)-phenylsulfonamido-β-alanine,
4-(2-Aminothiazol-4-yl)butanoyl-glycyl-3(R)-(2-phenethyl)-β-alanine methyl ester,
4-(2-Aminothiazol-4-yl)butanoyl-glycyl-3(R)-(2-phenethyl)-β-alanine,
5-(2-Pyridylamino)pentanoylglycyl-2(S)-phenylsulfonamido-β-alanine ethyl ester,
5-(2-Pyridylamino)pentanoylglycyl-2(S)-phenylsulfonamido-β-alanine,
4-(2-Amino-pyridin-6-yl)butanoyl-sarcosine-3(R)-[(2-indol-3-yl)ethyl]-β-alanine ethyl ester,
4-(2-Aminopyridin-6-yl)butanoyl-sarcosine-3(R)-[(2-indol-3-yl)ethyl]-β-alanine,
4-(2-Aminopyridin-6-yl)butanoyl-glycyl-2(S)-phenylsulfonamido-β-alanine t-butyl ester,
4-(2-Aminopyridin-6-yl)butanoyl-glycyl-2(S)-phenylsulfonamido-β-alanine,
4-(Pyridin-4-yl)butanoyl-sarcosine-3(R)-[2-(indol-3-yl)ethyl]-β-alanine ethyl ester,
4-(Pyridin-4-yl)butanoyl-sarcosine-3(R)-[2-(indol-3-yl)ethyl]-β-alanine,
4-(2-Bocamino-pyridin-6-yl)butanoyl-N-cyclopropylglycyl-3(R)-(2-phenethyl)-β-alanine ethyl ester,
4-(2-Amino-pyridin-6-yl)butanoyl-N-cyclopropylglycyl-3(R)-(2-phenethyl)-β-alanine ethyl ester,
4-(2-Amino-pyridin-6-yl)butanoyl-N-cyclopropylglycyl-3(R)-(2-phenethyl)-β-alanine,
4-(2-Boc-amino-pyridin-6-yl)butanoyl-N-cyclopropylglycyl-3(R)-[(2-indol-3-yl)ethyl]-β-alanine,
4-(2-Amino-pyridin-6-yl)butanoyl-N-cyclopropylglycyl-3(R)-[(2-indol-3-yl)ethyl]-β-alanine,
4-(2-Bocamino-pyridin-6-yl)butanoyl-N-cyclopropylglycyl-3(R)-methyl-β-alanine ethyl ester,
4-(2-Amino-pyridin-6-yl)butanoyl-N-cyclopropylglycyl-3(R)-methyl-β-alanine ethyl ester,
4-(2-Amino-pyridin-6-yl)butanoyl-N-cyclopropylglycyl-3(R)-methyl-β-alanine,
4-(Pyzidin-4-yl)butanoyl-N-(2-phenylethyl)glycyl-3(R)-(2-phenethyl)-β-alanine ethyl ester,
4-(Pyridin-4-yl)butanoyl-N-(2-phenyl)glycyl-3(R)-(2-phenethyl)-β-alanine,
b  4-(2-BOC-Aminopyridin-4-yl)butanoyl-N-(2-phenethyl)glycyl-3(R)-methyl-β-alanine,
4-(2-Aminopyridin-4-yl)butanoyl-N-(2-phenethyl)glycyl-3(R)-methyl-β-alanine,
4-(Pyridyloxy)butyrate-N-(2-phenethyl)glycyl-3(R)-2-phenethyl-β-alanine ethyl ester,
4-(Pyridyloxy)butyrate-N-(2-phenethyl)glycyl-3(R)-2-phenethyl-β-alanine, 3-[(N-Methyl)-N-(4-pyridyl)]aminopropionyl-sarcosine-3(R)-(2-phenethyl)-β-alanine ethyl ester,
3-[(N-Methyl)-N-(4-pyridyl)]aminopropionyl-sarcosine-3(R)-(2-phienethyl)-β-alanine,
N—{N'-3-(4-t-Butoxycarbonyl-1-piperizinyl)benzoyl)glycyl}-3(R)-methyl-β-alanine benzyl ester,
N—[N'-[3-(1-Piperazinyl)benzoyl]glycyl]-3(R)-methyl-β-alanine,
N—[N'-[3-(4-t-Butoxycarbonyl-1-piperazinyl)benzoyl]glycyl]-3(R)-(2-phenethyl)-β-alanine methyl ester,
N—[N'-[3-(1-Piperazinyl)benzoyl]glycyl]3(R)-(2-phenethyl)-β-alanine,
N—[N'-[3-(4-t-Butoxycarbonyl-1-piperazinyl)benzoyl]-N'-(2-phenethyl)glycyl]-3(R)-(2-phenethyl)-β-alanine methyl ester,
N—[N'-[3-(1-Piperazinyl)benzoyl]-N'-(2-phenethyl)glycyl]-3(R)-(2-phenethyl)-β-alanine,
4-(1,2,3,4-Tetrahydro-1,8-naphithyridin-7-yl)butanol-glycyl-β-alanine t-butyl ester,
4-(1,2,3,4-Tetrahydro-1,8-naphthyridin-7-yl)butanoyl-glycyl-β-alanine,
4-(1,2,3,4-Tetrahydro-1,8-naphthyridin-7-yl)butanoyl-glycyl-3(S)-pyridin-3-yl-β-alanine ethyl ester,
4-(1,2,3,4-Tetrahydro-1,8-naphthyridin-7-yl)butanoyl-glycyl-3(S)pyrdin-3-yl-β-alanine,
Ethyl N-pyridin-4-ylisonipecotyl-N-cyclopropylglycine-3(S)-ethynyl-β-alanine,
N-Pyridin-ylisonipecotyl-N-cyclopropylglycine-3(S)-ethynyl-β-alanine,
Ethyl N-pyridin-4-ylnipecotyl-N-cyclopropylglycine-3(S)-ethynyl-β-alanine,
N-Pyridin-4-ylnipecotyl-N-cydlopropylglycine-3(S)-ethynyl-β-alanine,
4-(1,2,3,4-Tetrahydlro-1,8-naphthyriclin-5-yl)butanoyl-N-(cyclo-propyl)gly-3(S)ethynyl-β-alanine ethyl ester,
4-(1,2,3,4-Tetrahydlro-1,8-naphthyriclin-5-yl)butanoyl-N-(cyclo-propyl)glycyl-3(S)-ethynyl-β-alanine, and
3-{2-[5-(1H-Benzoimidazol-2-yl-amino)-pentanoylamino]-acetylamino}-3(S)-pyridin-3-yl-propionic acid,
and pharmaceutically acceptable salts thereof.

7. A method of claim 6 wherein the salt is selected from the group consisting of
4-(2-Aminothiazol-4-yl)butanoyl-glycyl-3(R)-(2-phenethyl)-β-alanine trifluoroacetate salt,
5-(2-Pyridylamino)pentanoylglycyl-2(S)-phenylsulfonamido-β-alanine trifluoroacetate salt,
N—[N'-[3-(1-Piperazinyl)benzoyl]glycyl]-3(R)-methyl-β-alanine trifluoroacetic acid salt,
N—[N'-[3-(1-Piperazinyl)benzoyl]glycyl]-3(R)-(2-phenethyl)-β-alanine trifluoroacetic acid salt,
N—[N'-[3-(1-Piperazinyl)benzoyl]-N'-(2-phenethyl)glycyl]-3(R)-(2-phenethyl)-β-alanine trifluoroacetic acid salt, and
4-(2-Amino-pyridin-6-yl)butanoyl-N-cyclopropylglycyl-3(R)-(2-phenethyl)-β-alanine ethyl ester hydrochloride.

8. The method of claim 1 wherein the condition is diabetic retinopathy.

9. A composition comprising a carrier suitable for topical ophthamological administration and between about 0.01–5% w/v of a compound of the formula:

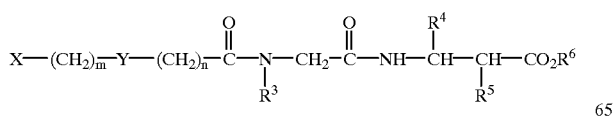

and pharmaceutically acceptable salts thereof, wherein

X is
a 5- or 6-membered monocyclic aromatic ring system containing 0, 1, 2, 3 or 4 heteroatoms selected from N, O and S and either unsubstituted or substituted with $R^1$ or $R^2$, or
a 9- to 10-membered polycyclic ring system, wherein one or more of the rings is aromatic, containing 0, 1, 2, 3 or 4 heteroatoms selected from N, O or S and either unsubstituted or substituted with $R^1$ or $R^2$,
wherein $R^1$ and $R^2$ are independently selected from the group consisting of
hydrogen, F, Cl, Br, I,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-4}$ alkoxy,
$C_{1-4}$ alkoxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy $C_{1-6}$ alkyloxy,
hydroxy, and
hydroxy $C_{1-6}$ alkyl;

Y is

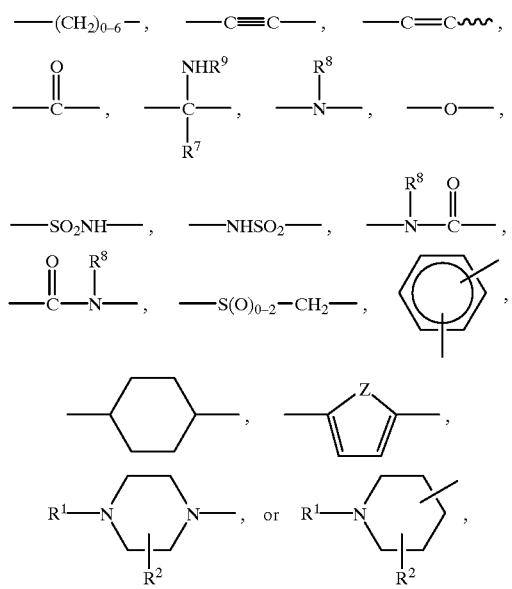

where Z is O, $NR^8$, or S; and $R^8$ is defined as $R^1$ above;
$R^3$ and $R^4$ are independently
hydrogen,
a five or six membered mono or nine or ten membered polycyclic unsaturated, partially or fully saturated ring system containing 0, 1, 2, 3, or 4 heteroatoms selected from nitrogen, oxygen and sulfuir, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, —(CH$_2$)$_n$-aryl, wherein n=1–4 and aryl is defined as a five or six membered unsaturated or partially saturated monocyclic ring system, or nine or ten membered polycyclic ring system wherein at least one of the rings is unsaturated or partially saturated and each of the other rings is optionally unsaturated, partially saturated or fully saturated, said aryl group containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl, hydroxycarbonyl$C_{1-5}$ alkyl, or hydroxycarbonyl$C_{1-5}$ alkoxy, halogen,
hydroxyl,
$C_{1-5}$alkylcarbonylamino,
aryl$C_{1-5}$ alkoxy,
$C_{1-5}$ alkoxycarbonyl,
aminocarbonyl,
$C_{1-5}$ alkylaminocarbonyl,
$C_{1-5}$ alkylcarbonyloxy,
$C_{3-8}$ cycloalkyl,
oxo,
amino,
$C_{1-3}$ alkylamino,
amino$C_{1-3}$ alkyl,
arylaminocarbonyl,
aryl$C_{1-5}$alkylaminocarbonyl,
aminocarbonyl,
aminocarbonyl-$C_{1-4}$ alkyl,
hydroxycarbonyl,
hydroxycarbonyl $C_{1-5}$ alkyl,
$C_{1-6}$alkyl, either unsubstituted or substituted, with one or more groups selected from halogen, hydroxyl, $C_{1-5}$alkylcarbonylamino, arylCl$_5$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino$C_{1-3}$ alkyl, arylaminocarbonyl, aryl$C_{1-5}$alkylaminocarbonyl, aminocarbonyl, aminocarbonyl-$C_{1-4}$ alkyl, hydroxycarbonyl, or hydroxycarbonyl $C_{1-5}$ alkyl, provided that the carbon atom to which R$^3$ and R$^4$ are attached bears only one heteroatom,
—(CH$_2$)$_m$C≡CH,
—(CH$_2$)$_m$C≡C—$C_{1-6}$ alkyl,
—(CH$_2$)$_m$C≡C—$C_{3-7}$cycloalkyl,
—(CH$_2$)$_m$C≡C— aryl,
—(CH$_2$)$_m$C≡C—$C_{1-6}$ alkyl aryl,
—(CH$_2$)$_m$CH═CH$_2$,
—(CH$_2$)$_m$CH═CH $C_{1-6}$ alkyl,
—(CH$_2$)$_m$CH═CH—$C_{3-7}$cycloalkyl,
—(CH$_2$)$_m$CH═CH aryl,
—(CH$_2$)$_m$CH═CH $C_{1-6}$ alkyl aryl,
—(CH$_2$)$_m$SO$_2$$C_{1-6}$ alkyl, or
—(CH$_2$)$_m$SO$_2$$C_{1-6}$ alkylaryl;

R$^5$ is
hydrogen,
fluorine,
$C_{1-8}$ alkyl,
hydroxyl,
hydroxy $C_{1-6}$ alkyl,
carboxy,
carboxy $C_{1-6}$ alkyl,
$C_{1-6}$ alkyloxy,
$C_{3-8}$ cycloalkyl,
aryl $C_{1-6}$ alkyloxy,
aryl,
aryl $C_{1-6}$ alkyl,
$C_{1-6}$ alkylcarbonyloxy,
amino,
$C_{1-6}$ alkylamino,
amino $C_{1-6}$ alkyl,
$C_{1-6}$ alkylamino $C_{1-6}$ alkyl,
aryl amino,
aryl amino $C_{1-6}$ alkyl,
aryl $C_{1-6}$ alkylamino,
aryl $C_{1-6}$ alkylamino $C_{1-6}$ alkyl,
aryl carbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
aryl sulfonylamino $C_{1-6}$ alkyl,
aryl sulfonylamino,
aryl $C_{1-6}$ alkylsulfonylamino,
aryl $C_{1-6}$ alkylsulfonylamino $C_{1-6}$ alkyl,
$C_{1-8}$ alkyloxycarbonylamino,
$C_{1-8}$ alkyloxycarbonylamino $C_{1-8}$ alkyl,
aryl $C_{1-8}$ alkyloxycarbonylamino,
aryl oxycarbonylamino,
aryl oxycarbonylamino $C_{1-8}$ alkyl,
aryl $C_{1-8}$ alkyloxycarbonylamino $C_{1-8}$ alkyl,
$C_{1-8}$ alkylcarbonylamino,
$C_{1-8}$ alkylcarbonylamino $C_{1-6}$ alkyl,
aryl carbonylamino $C_{1-6}$ alkyl,
aryl carbonylamino,
aryl $C_{1-6}$ alkylcarbonylamino,
aryl $C_{1-6}$ alkylcarbonylamino $C_{1-6}$ alkyl,
$C_{1-8}$ alkylaminocarbonylamino,
aminocarbonylamino,
aminocarbonylamino $C_{1-6}$ alkyl,
$C_{1-8}$ alkylaminocarbonylamino $C_{1-6}$ alkyl,
aryl aminocarbonylamino $C_{1-6}$ alkyl,
aryl aminocarbonylamino,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
aminosulfonylamino,
$C_{1-8}$ alkylaminosulfonylamino,
$C_{1-8}$ alkylaminosulfonylamino $C_{1-6}$ alkyl,
aryl aminosulfonylamino $C_{1-6}$ alkyl,
aryl aminosulfonylamino,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$alkyl,
aryl sulfonyl,
aryl sulfonyl $C_{1-6}$alkyl,
aryl alkylsulfonyl,
aryl $C_{1-6}$ alkylsulfonyl,
aryl $C_{1-6}$ alkylsulfonyl $C_{1-6}$alkyl,
$C_{1-6}$ alkylcarbonyl,
$C_{1-6}$ alkylcarbonyl $C_{1-6}$ alkyl,
aryl carbonyl $C_{1-6}$alkyl, aryl carbonyl,
aryl $C_{1-6}$ alkylcarbonyl,
aryl $C_{1-6}$ alkylcarbonyl $C_{1-6}$alkyl,
$C_{1-6}$ alkylthiocarbonylamino,
$C_{1-6}$ alkylthiocarbonylamino $C_{1-6}$ alkyl,
aryl thiocarbonylamino $C_{1-6}$ alkyl,
aryl thiocarbonylamino,
aryl $C_{1-6}$ alkylthiocarbonylamino,
aryl $C_{1-6}$ alkylthiocarbonylamino $C_{1-6}$ alkyl,
aminocarbonyl $C_{1-6}$ alkyl,
aminocarbonyl,
$C_{1-8}$ alkylaminocarbonyl,
$C_{1-8}$ alkylaminocarbonyl $C_{1-6}$ alkyl,
aryl aminocarbonyl $C_{1-6}$ alkyl,
aryl aminocarbonyl,
aryl $C_{1-8}$ alkylaminocarbonyl,
aryl $C_{1-8}$ alkylaminocarbonyl $C_{1-6}$ alkyl,
wherein alkyl groups and aryl groups are optionally unsubstituted or substituted with one or more substituents selected from $R^1$ and $R^2$; and $R^6$, $R^7$, and $R^9$ are independently
hydrogen,
$C_{1-8}$ alkyl,
aryl,
aryl $C_{1-8}$ alkyl,
hydroxy,
$C_{1-8}$ alkyloxy,
aryloxy,
aryl $C_{1-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy,
$C_{1-8}$ alkylaminocarbonylmethyleneoxy, or
$C_{1-8}$ dialkylaminocarbonylmethyleneoxy,
and wherein m and n are integers 0–6.

10. A method for inhibiting diabetic retinopathy in a patient comprising topically applying to the patient's eye a therapeutically effective amount of the composition of claim 9.

* * * * *